US012594352B2

(12) United States Patent
Sanfilippo et al.

(10) Patent No.: US 12,594,352 B2
(45) Date of Patent: Apr. 7, 2026

(54) PASTEURIZATION UNIT AND METHODS OF USING THE SAME

(71) Applicant: SANFILIPPO TECH, LLC., Schaumburg, IL (US)

(72) Inventors: James J. Sanfilippo, Schaumburg, IL (US); John Sanfilippo, Schaumburg, IL (US)

(73) Assignee: SANFILIPPO TECH, LLC., Schaumburg, IL (US)

( * ) Notice: Subject to any disclaimer, the term of this patent is extended or adjusted under 35 U.S.C. 154(b) by 81 days.

(21) Appl. No.: 18/683,378

(22) PCT Filed: Aug. 16, 2022

(86) PCT No.: PCT/US2022/040522
§ 371 (c)(1),
(2) Date: Feb. 13, 2024

(87) PCT Pub. No.: WO2023/023103
PCT Pub. Date: Feb. 23, 2023

(65) Prior Publication Data
US 2024/0366819 A1 Nov. 7, 2024

Related U.S. Application Data

(60) Provisional application No. 63/262,683, filed on Oct. 18, 2021, provisional application No. 63/233,625, filed on Aug. 16, 2021.

(51) Int. Cl.
*A61L 2/07* (2006.01)
*A61L 2/26* (2006.01)
(Continued)

(52) U.S. Cl.
CPC .................... *A61L 2/07* (2013.01); *A61L 2/26* (2013.01); *B65B 37/04* (2013.01); *B65B 55/02* (2013.01);
(Continued)

(58) Field of Classification Search
CPC .......... A61L 2/07; A61L 2/26; A61L 2202/11; A61L 2202/121; A61L 2202/122; A61L 2202/15; A61L 2202/16; B65B 55/02; B65B 55/027; B65B 55/10; B65B 55/12; B65B 55/18
(Continued)

(56) References Cited

U.S. PATENT DOCUMENTS

| | | | | |
|---|---|---|---|---|
| 3,204,629 A | * | 9/1965 | Newton, Jr. ............ | F24H 1/107 122/448.1 |
| 3,778,521 A | * | 12/1973 | Fisher et al. ........ | B01F 33/8052 426/508 |

(Continued)

FOREIGN PATENT DOCUMENTS

| | | |
|---|---|---|
| CN | 112 204 693 A | 1/2021 |
| WO | WO-2019/133952 A2 | 7/2019 |

OTHER PUBLICATIONS

International Search Report and Written Opinion for Application No. PCT/US2022/040522, dated Jan. 23, 2023.

*Primary Examiner* — Sameh Tawfik
(74) *Attorney, Agent, or Firm* — MARSHALL, GERSTEIN & BORUN LLP

(57) ABSTRACT

A pasteurization unit and process for pasteurization of products such as cannabis and hemp.

15 Claims, 47 Drawing Sheets

(51) Int. Cl.
    *B65B 37/04*         (2006.01)
    *B65B 55/02*         (2006.01)

(52) U.S. Cl.
    CPC ...... *A61L 2202/11* (2013.01); *A61L 2202/121*
        (2013.01); *A61L 2202/122* (2013.01); *A61L*
        *2202/15* (2013.01); *A61L 2202/16* (2013.01)

(58) Field of Classification Search
    USPC .......................................................... 53/127
    See application file for complete search history.

(56)            References Cited

U.S. PATENT DOCUMENTS

| | | | | |
|---|---|---|---|---|
| 4,125,063 | A * | 11/1978 | Jelks | A23N 17/001 |
| | | | | 99/534 |
| 4,396,582 | A * | 8/1983 | Kodera | A61L 2/18 |
| | | | | 53/167 |
| 4,734,268 | A * | 3/1988 | Redding | B65B 55/027 |
| | | | | 53/167 |
| 4,833,793 | A * | 5/1989 | White | A23K 30/00 |
| | | | | 34/178 |
| 4,957,043 | A * | 9/1990 | Silvestrini | A23N 1/02 |
| | | | | 99/473 |
| 5,960,703 | A * | 10/1999 | Jara | A47J 27/16 |
| | | | | 99/443 C |
| 11,234,444 | B1 | 2/2022 | Gunawardena et al. | |
| 2005/0103213 | A1* | 5/2005 | Dumm | A23B 11/1303 |
| | | | | 99/483 |
| 2009/0223080 | A1* | 9/2009 | McCarthy | A61J 1/10 |
| | | | | 34/92 |
| 2011/0183058 | A1* | 7/2011 | Fujiwara | A23B 2/405 |
| | | | | 426/511 |
| 2014/0348988 | A1* | 11/2014 | Braun | A23B 2/708 |
| | | | | 426/511 |
| 2015/0010679 | A1 | 1/2015 | Strong et al. | |
| 2016/0073674 | A1 | 3/2016 | Adam | |
| 2020/0154692 | A1* | 5/2020 | Newman | B05B 7/2494 |
| 2020/0178593 | A1 | 6/2020 | Van Hattem et al. | |
| 2021/0052753 | A1 | 2/2021 | Novotny | |
| 2023/0056299 | A1* | 2/2023 | Sanfilippo | B65B 37/04 |
| 2023/0157337 | A1* | 5/2023 | Ella | A23L 27/10 |
| | | | | 426/240 |
| 2024/0139357 | A1* | 5/2024 | Geurtsen | C09D 5/022 |
| 2025/0025590 | A1* | 1/2025 | Dolan | A61B 90/70 |
| 2025/0100903 | A1* | 3/2025 | Ochi | C02F 1/325 |

* cited by examiner

Figure 2A                                        Figure 2B

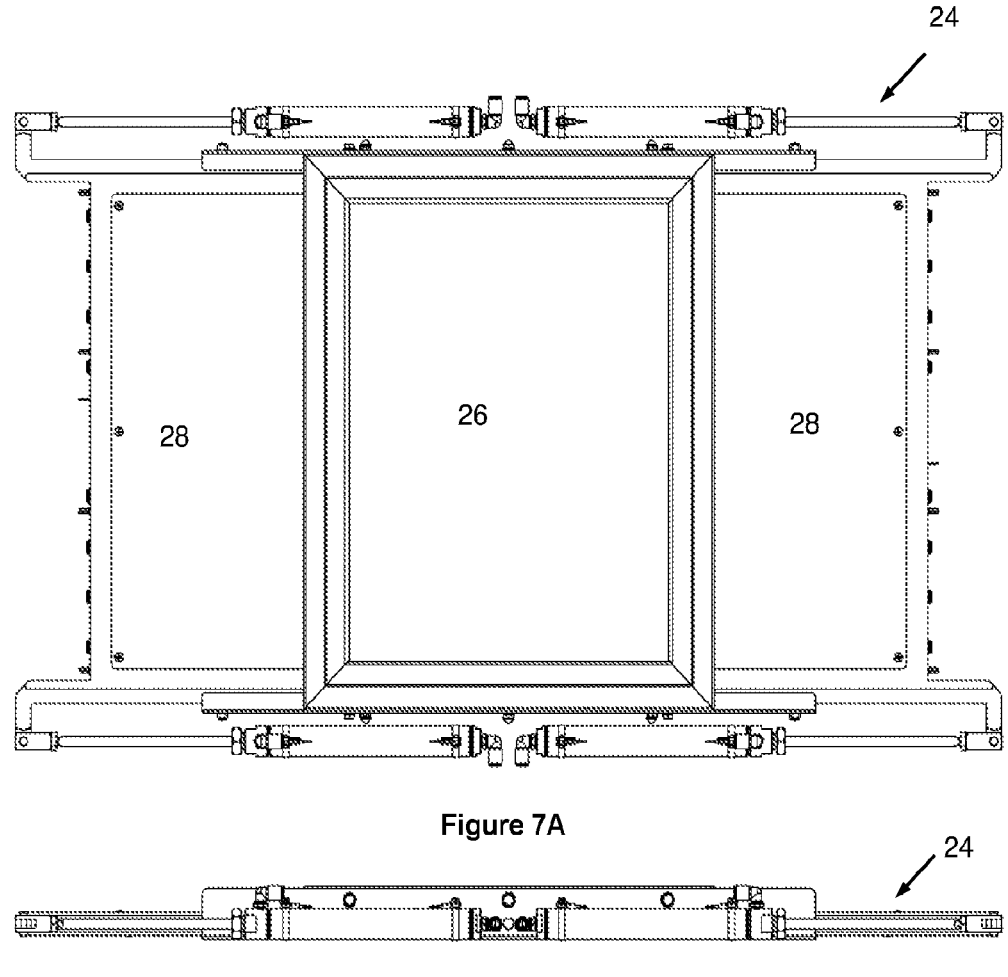
Figure 7A
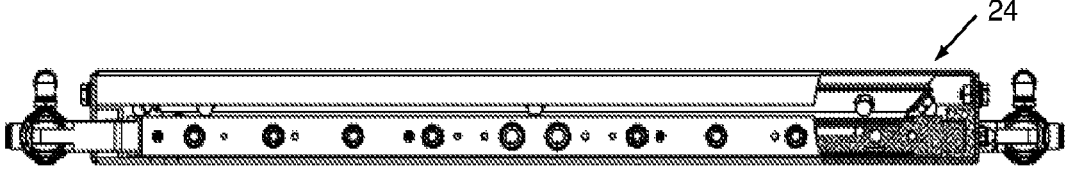
Figure 7B
Figure 7C

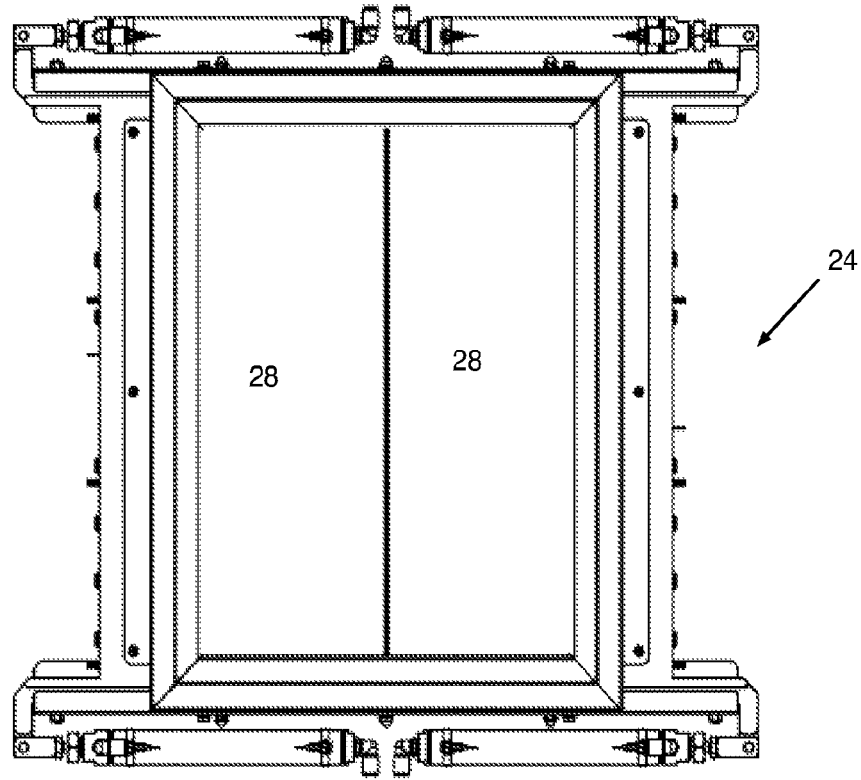
Figure 8C
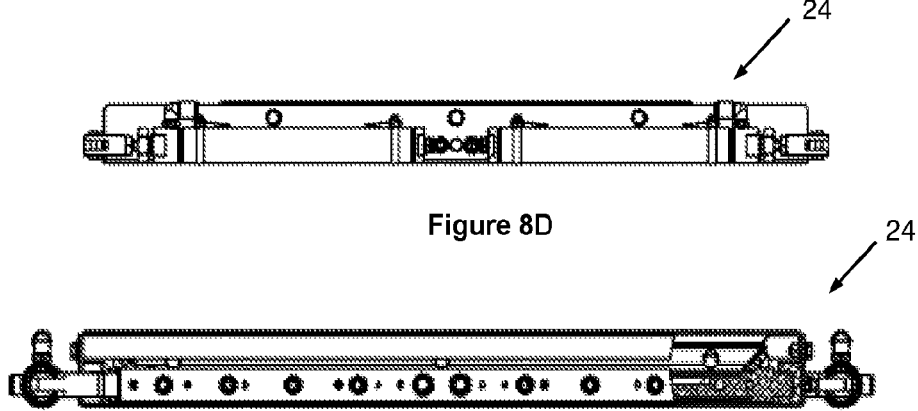
Figure 8D
Figure 8E

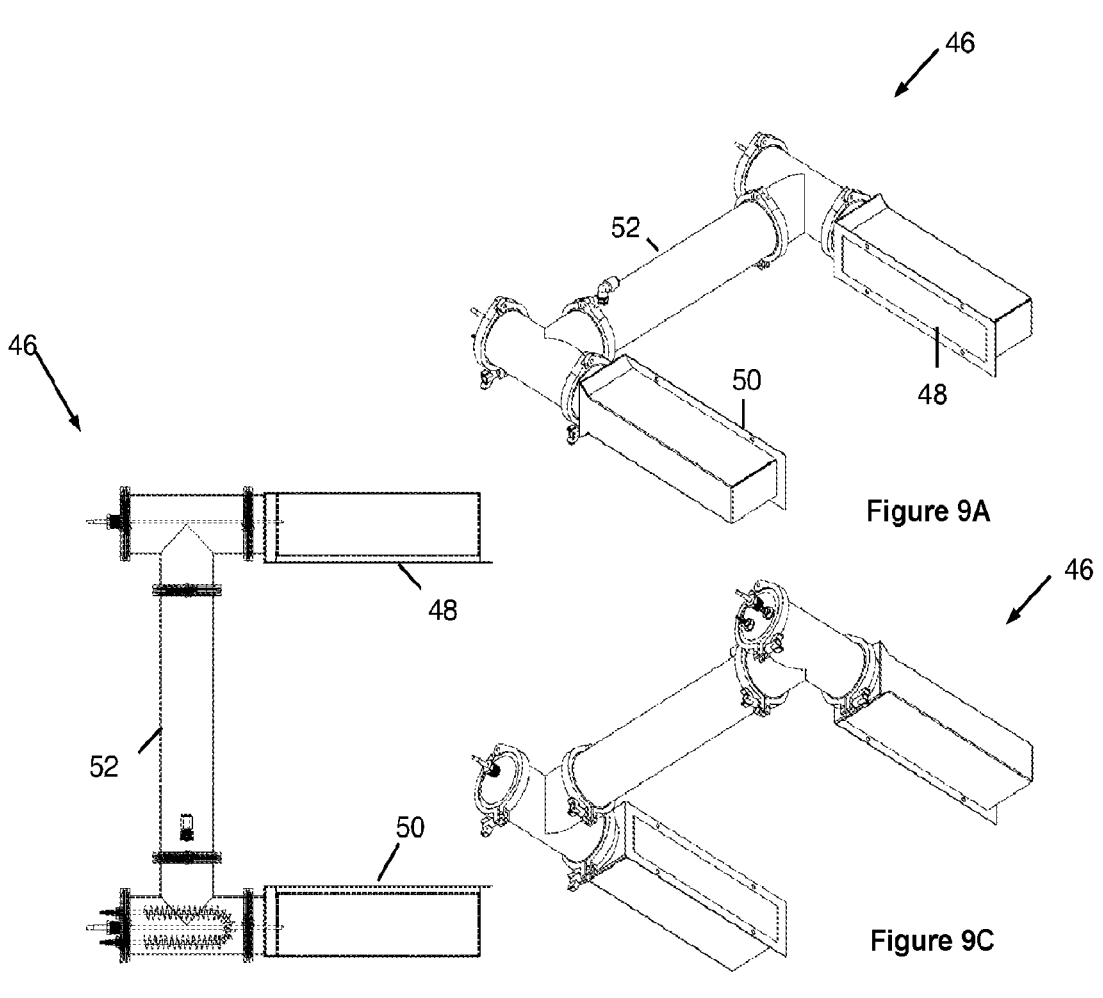
Figure 9A
Figure 9B
Figure 9C
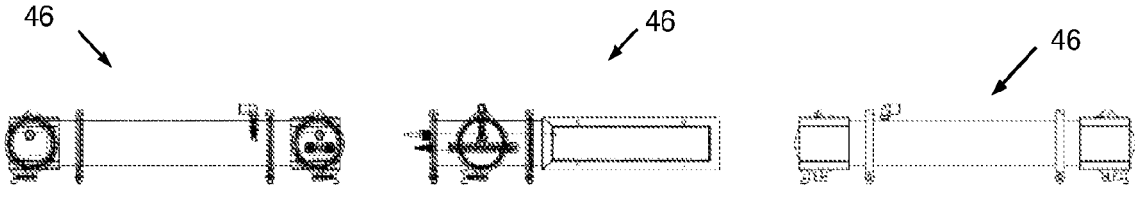
Figure 9D
Figure9E
Figure 9F

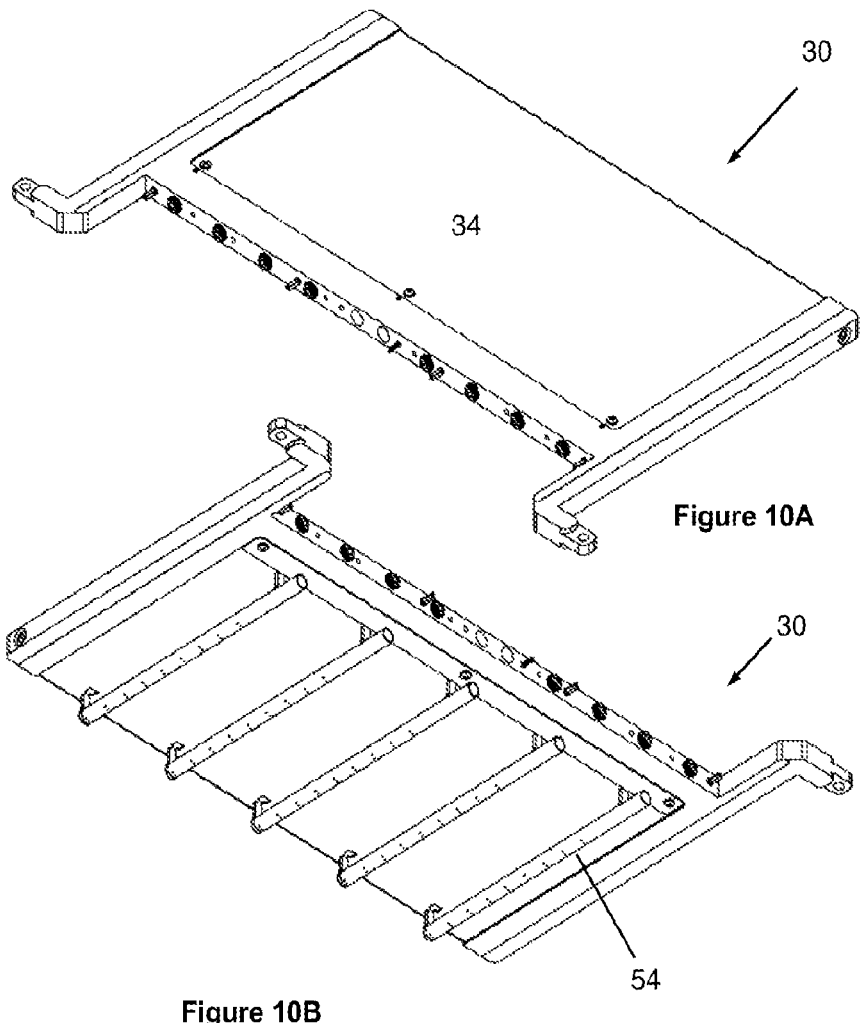
Figure 10A
Figure 10B
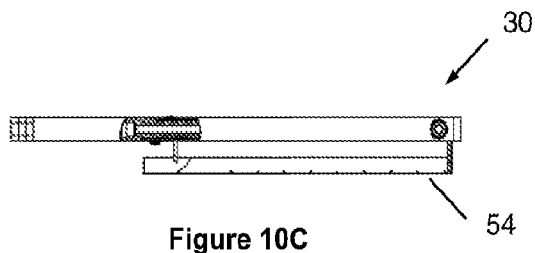
Figure 10C

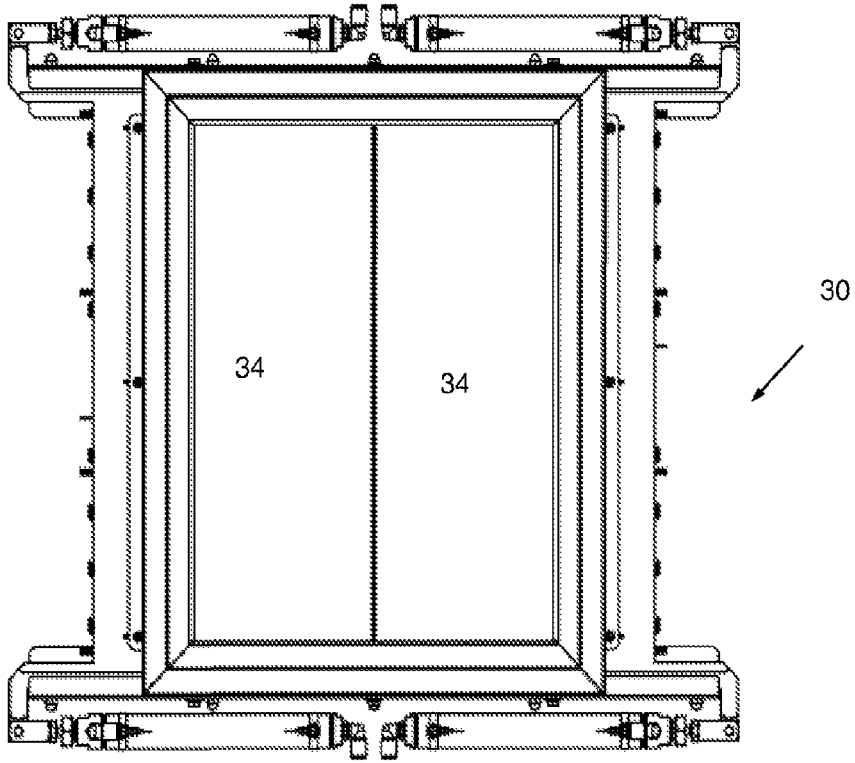
Figure 12C
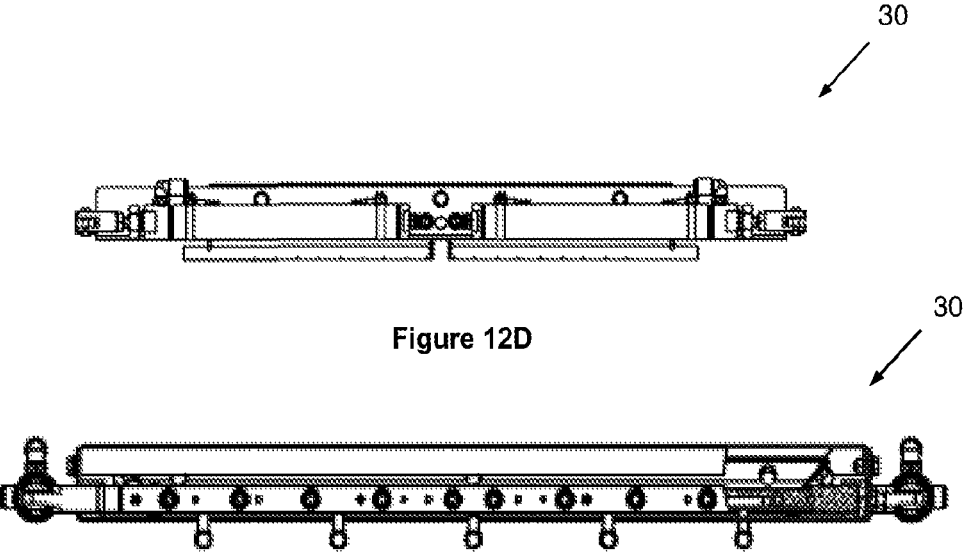
Figure 12D
Figure 12E

36

40          40

36

36

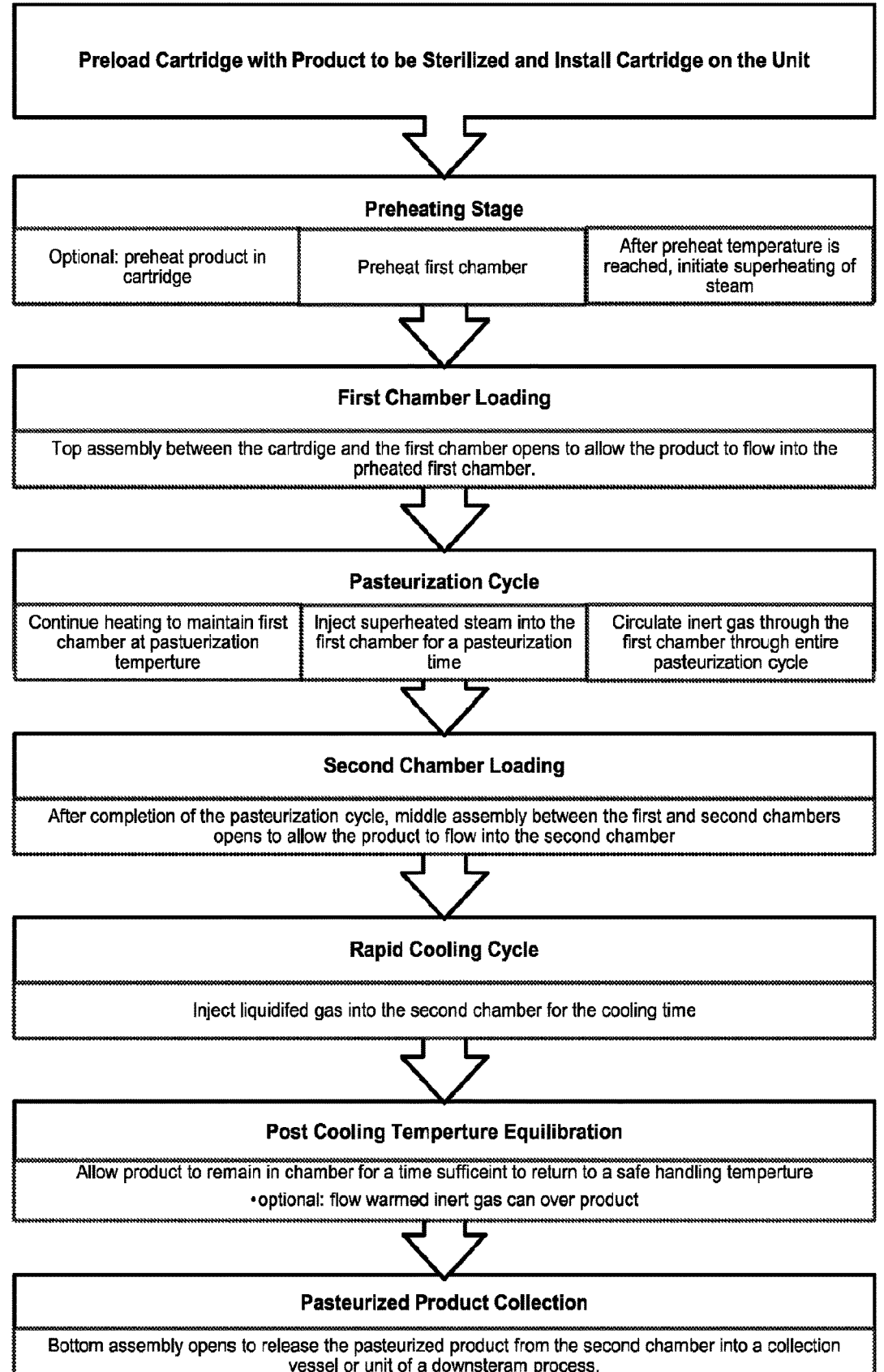

Preload Cartridge with Product to be Sterilized and Install Cartridge on the Unit

Preheating Stage

| Optional: preheat product in cartridge | Preheat first chamber | After preheat temperature is reached, initiate superheating of steam |
| --- | --- | --- |

First Chamber Loading

Top assembly between the cartrdige and the first chamber opens to allow the product to flow into the prheated first chamber.

Pasteurization Cycle

| Continue heating to maintain first chamber at pastuerization temperture | Inject superheated steam into the first chamber for a pasteurization time | Circulate inert gas through the first chamber through entire pasteurization cycle |
| --- | --- | --- |

Second Chamber Loading

After completion of the pasteurization cycle, middle assembly between the first and second chambers opens to allow the product to flow into the second chamber

Rapid Cooling Cycle

Inject liquidifed gas into the second chamber for the cooling time

Post Cooling Temperture Equilibration

Allow product to remain in chamber for a time sufficeint to return to a safe handling temperture
•optional: flow warmed inert gas can over product

Pasteurized Product Collection

Bottom assembly opens to release the pasteurized product from the second chamber into a collection vessel or unit of a downsteram process.

Figure 18

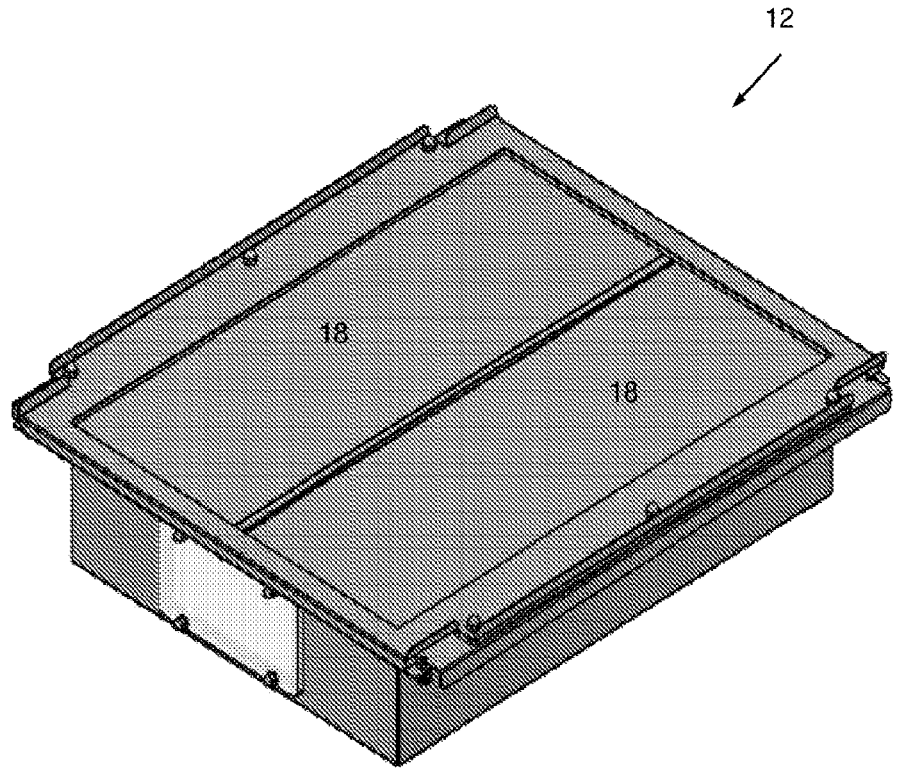
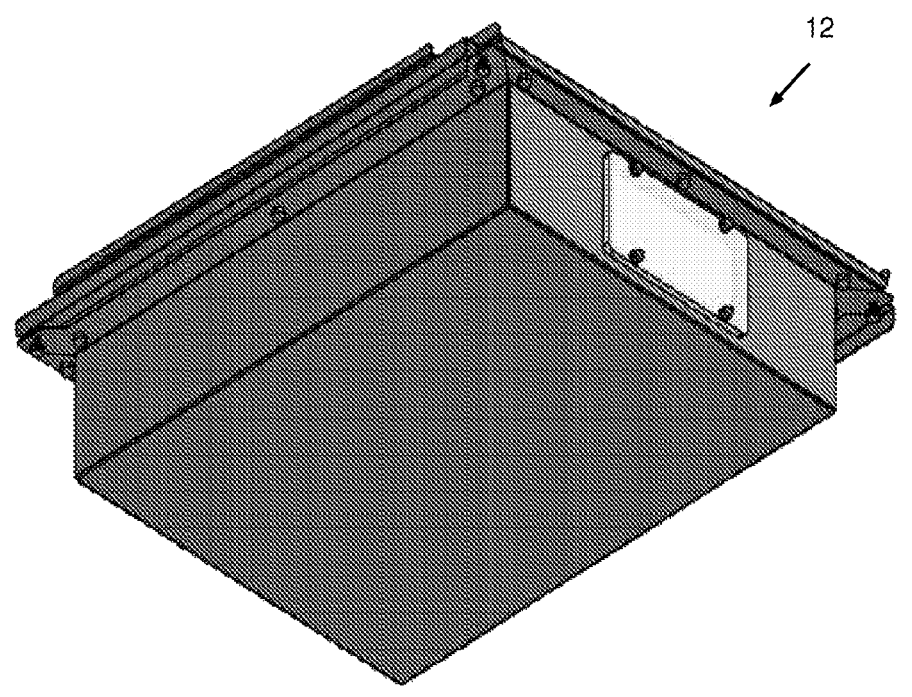
Figure 21

CryoPasteurization - Thermal Death Curves at 165'F - Enhanced Quality Window
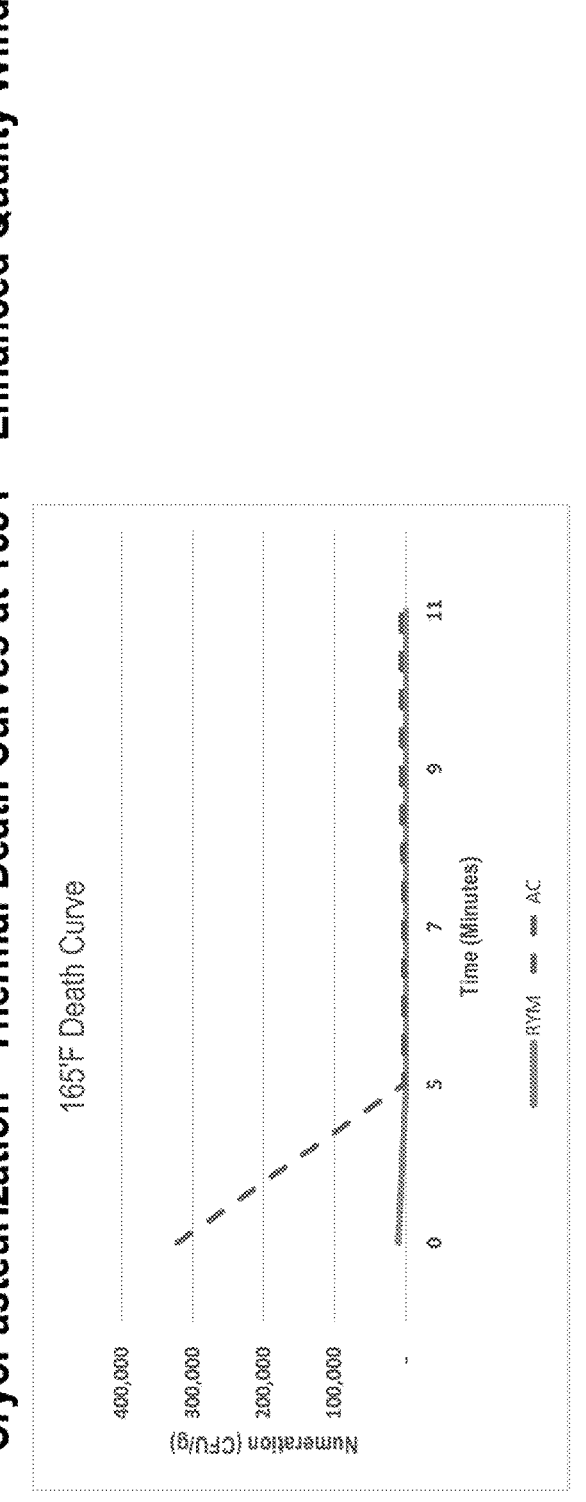
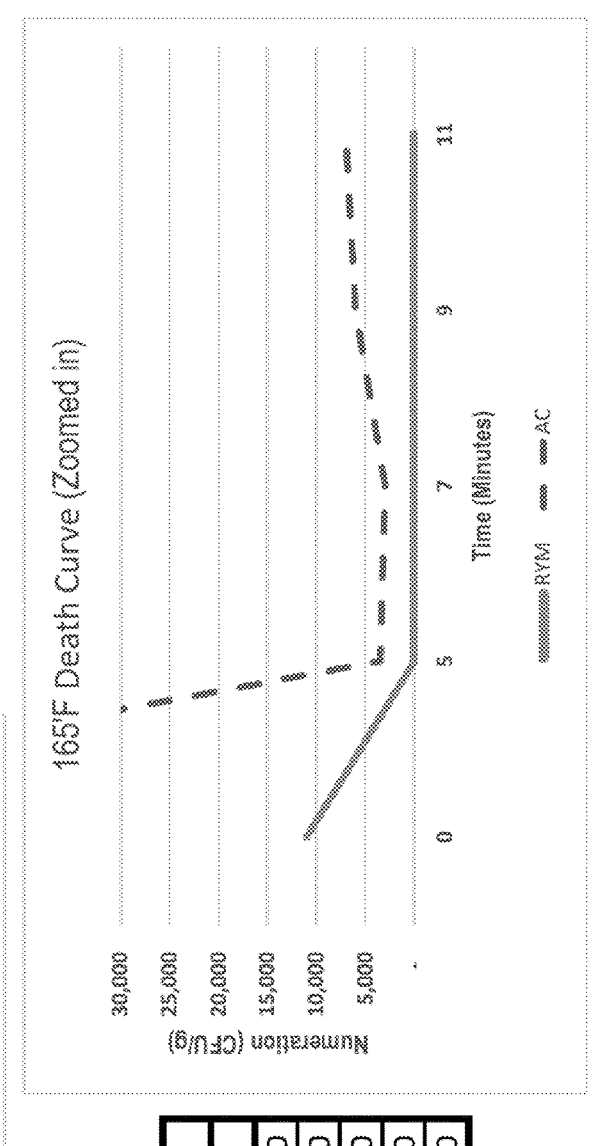
| Data at 165'F Chamber Temp | | |
| --- | --- | --- |
| Time (Minutes) | RYM | AC |
| 0 | 11,000 | 322,000 |
| 5 | 0 | 3,500 |
| 7 | 0 | 3,000 |
| 9 | 0 | 6,000 |
| 11 | 0 | 7,000 |
Figure 22

Openings in Transition Chute

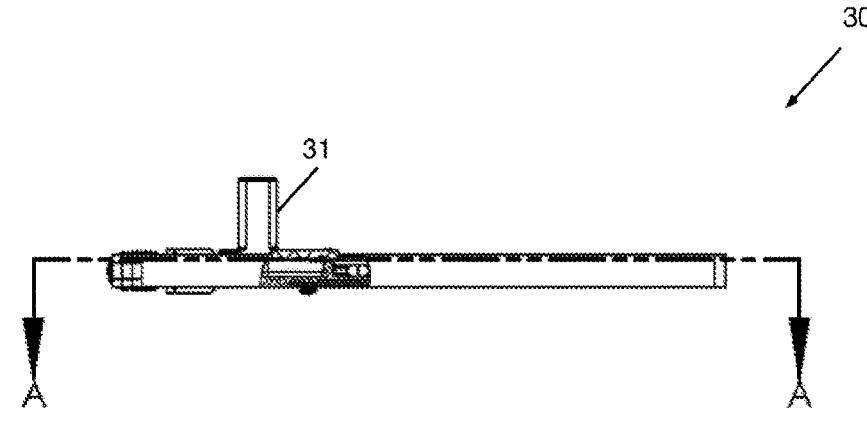
Figure 25C
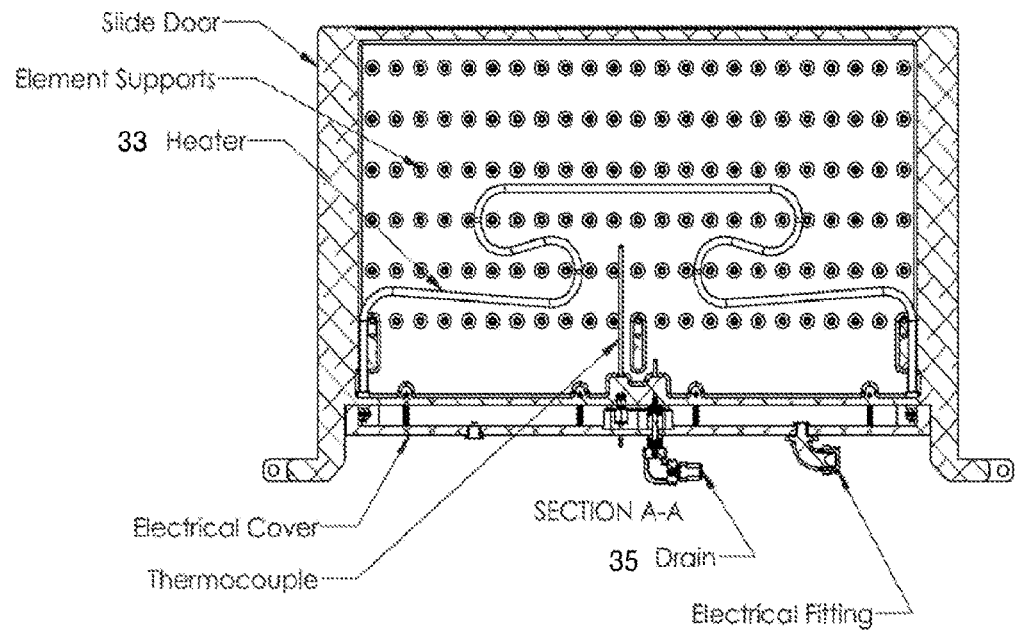
Figure 25D
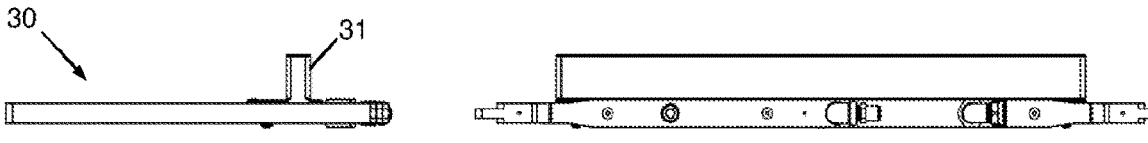
Figure 25E                                             Figure 25F

10

PASTEURIZATION UNIT AND METHODS OF USING THE SAME

BACKGROUND

Field of the Disclosure

The disclosure relates to pasteurization units and methods of using the same, and more particularly to pasteurization units for pasteurizing cannabis and/or hemp products and methods of pasteurizing cannabis and/or hemp products using the same.

Brief Description of Related Technology

Product pasteurization is important and widely used in a variety of industries, such as the food and pharmaceutical industries. Various methods of pasteurization have been developed depending on the product to be pasteurized. Recent regulations have made pasteurization a focus in the cannabis industry. Cannabis and hemp products are flowable products and can be particularly sensitive to external stimulus, such as heat or chemical exposure, resulting in discoloration or other damage to the product. Damage can include adverse effects on the flavoring of the product, such as destruction or modification of terpenes in or added to cannabis products, and/or reduction of the effectiveness, such as changes in the THC levels. This sensitivity makes many conventional pasteurization techniques used, for example, in the food and beverage industry, unsuitable for cannabis and hemp.

Cannabis, by its nature as a plant product can also have inherent levels of contaminants. Additionally, the environment in which the cannabis is processed having high airborne levels of contaminants making it difficult to maintain a pasteurized product even after pasteurization. Contaminants can include mold spores, bacteria and viruses.

Conventional methods for pasteurizing cannabis products include vacuum pasteurization relying upon the generation of sub-atmospheric pressures within a chamber that includes a gaseous or aerosolized pasteurization reagent. One such system is described in International Patent Application Publication No. WO 2019/133952. Such systems require that the product be contained within a pasteurization package, such as a Tyvek pouch to protect the product from the pasteurization environment, including the sterilizing reagents present in the chamber. The generation of vacuum can require significant time and energy costs, as well, requiring longer pasteurization times to achieve effectiveness. Longer pasteurization and prolonged exposure of the product to the pasteurization reagents can increase the potential for damage to the product.

SUMMARY

A pasteurization unit for pasteurizing a product can include a first chamber having an interior volume defined by a plurality of walls and having a product inlet for introduction of product into the interior volume and a product outlet for release of the product from the first chamber; a vapor generator in fluid communication with the first chamber for introduction of vapor into the first chamber for pasteurization of the product; the product inlet and the product outlet being sealable during pasteurization; a second chamber having an interior volume defined by a plurality of walls and comprising a product outlet and a product inlet, the second chamber being arranged to receive product from the first chamber for cooling the product; and cryogenic fluid inlets in fluid communication with a cryogenic fluid source, the cryogenic fluid inlets being arranged to direct cryogenic fluid into the interior volume of the second chamber to cool the product as it enters and/or once in the interior volume of the second chamber.

The pasteurization unit can further include a middle assembly arranged between the first and second chamber, the middle assembly having actuatable doors that are configured to expose the product outlet of the first chamber and the product inlet of the second chamber when open and close over the product outlet of the first chamber and the product inlet of the second chamber when closed.

The pasteurization unit can further include a circulation unit arranged in fluid communication with the vapor generator, the circulation unit comprising an inlet for receiving vapor from the vapor generator and an outlet in fluid communication with the first chamber for flowing vapor into the first chamber. The circulation unit comprises a blower arranged in a channel for directing flow of vapor into the first chamber. The pasteurization unit can further include a middle assembly arranged between the first and second chamber, the middle assembly having actuatable doors that are configured to expose the product outlet of the first chamber and the product inlet of the second chamber when open and close over the product outlet of the first chamber and the product inlet of the second chamber when closed, wherein each door comprises an inlet plenum extending from the door into the first chamber, and the circulation unit outlet is in fluid communication with an inlet plenum such that flow of vapor is directed into the first chamber from the vapor generator through the circulation and through the inlet plenum. The circulation unit can include a heater arranged in the channel. The first chamber can include a gas outlet for release vapor from the first chamber, and wherein the circulation unit is in fluid communication with the gas outlet and comprises a filter arranged at the outlet such that vapor flows through the filter before entering the circulation unit.

The pasteurization unit can further include a top assembly arranged upstream of the first chamber, the top assembly comprising actuatable doors for opening and closing over the product inlet of the first chamber.

The pasteurization unit of can further include a bottom assembly arrange downstream of the second chamber, the bottom assembly comprising actuatable doors for opening and closing over the product outlet of the second chamber.

The pasteurization unit can include top, middle, and bottom assemblies.

The cryogenic fluid inlets can be arranged in the second chamber.

The pasteurization unit can further include a cartridge for loading the product into the first chamber, the product adapted to be removably received upstream of the first chamber for introduction of the product from the chamber into the internal volume of the first chamber through the first chamber product inlet.

The pasteurization unit can further include inert gas inlets arranged to flow inert gas into the first chamber and/or the second chamber. The vapor generator can be in fluid communication with an inert gas source and adapted to flow vapor and inert gas into the first chamber.

The pasteurization unit can include a circulation unit arranged in fluid communication with an inert gas source, the circulation unit comprising an inlet for receiving inert gas from the inert gas source and an outlet in fluid communication with the second chamber for flowing vapor into the second chamber. The circulation unit comprises a channel through which the inert gas flows. The circulation unit can include a blower arranged within the channel.

A process for pasteurizing cannabis using the pasteurization unit of the disclosure can include introducing the product into the first chamber; flowing vapor from the vapor generator into the first chamber at a rate to maintain a pasteurization temperature for a pasteurization time; releasing the product from the first chamber through the first chamber product outlet and introducing the product into the second chamber through the second chamber product inlet; flowing cryogenic fluid into the second chamber to cool the product; holding the product in the second chamber for a hold time after cooling to bring the product to room temperature; and releasing the product from the second chamber through the second chamber product outlet.

The pasteurization temperature can be about 65° C. to about 75° C.

The pasteurization time can be about 1 min to about 10 min.

The process can further include preheating the first chamber before introducing the product into the first chamber.

Flowing vapor from the vapor generator comprises flowing a mixture of vapor and inert gas. The inert gas can be nitrogen.

The cryogenic fluid can be liquid nitrogen.

BRIEF DESCRIPTION OF THE DRAWINGS

FIGS. 7A-7E are various views of a top door assembly in accordance with the disclosure, showing the assembly in an open position.

FIG. 8A-8E are various views of the top door assembly of FIG. 7 showing the assembly in the closed position.

FIGS. 9A-9F are various view of a circulation unit 46 in accordance with the disclosure.

FIGS. 10A-10F are various views of a single panel of the middle door assembly in accordance with the disclosure.

FIGS. 12A-12E are various views of the middle door assembly of FIG. 11, showing the assembly in the closed position.

FIG. 15A-15F are various views of a pasteurization unit in accordance with the disclosure.

FIG. 18 is a process flow chart for a method of pasteurization in accordance with the disclosure.

FIG. 21 is perspective views of the cartridge 12 of FIG. 20 showing the cartridge 12 in the closed position.

FIG. 22 is a graph showing thermal death curves measuring for rapid yeast and mold count (RYM) and aerobic count (AC) using a process of the disclosure.

FIGS. 25A to 25F are schematic illustrations of various views of a middle door assembly for use in units of the disclosure.

DETAILED DESCRIPTION

Figure 1:
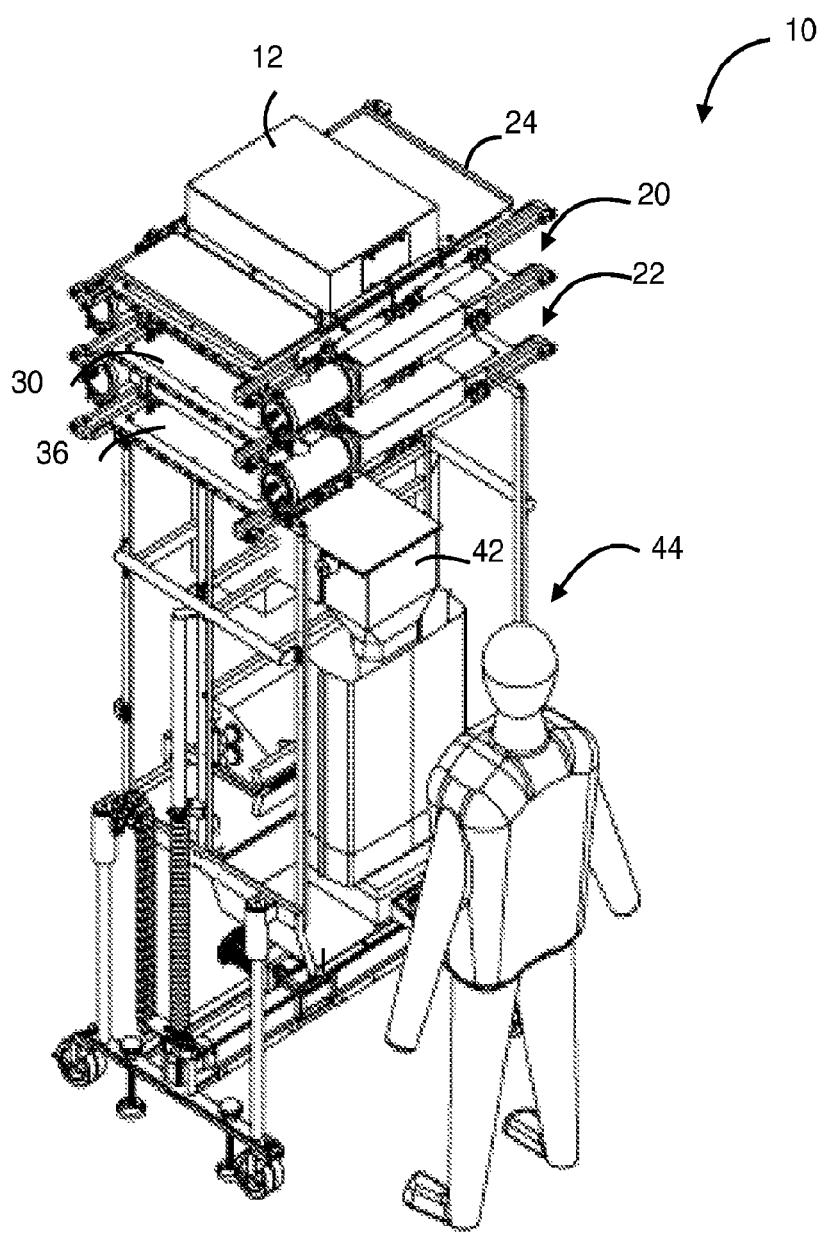
FIG. 1 is perspective view of a system in accordance with the disclosure.

It has advantageously been found that the pasteurization unit and methods of pasteurizing products of the disclosure can safely and effectively pasteurize flowable products and particularly those products that are sensitive to heat and/or chemical exposure. In particular, the pasteurization unit and methods of the disclosure can be advantageous for pasteurization of cannabis and hemp products. Cannabis and hemp products have interstitial spaces within the buds, which can trap spores, making it difficult to effectively pasteurize the products. The unit and methods of the disclosure can advantageously heat the core of the buds to a temperature sufficient to pasteurize contaminants present in these interstitial spaces through the combined use of a heated chamber and heated vapor, such as water vapor, as well a flow of inert gas to reduce or eliminate oxygen in and around the product during and after pasteurization. Using low oxygen environments and/or use of high humidity (including vapor) can help to preserve and/or minimize damage to terpenes and cannabinoids during pasteurization. The vapor can also allow for control over the relative humidity during pasteurization. This can be advantageous for sensitive products, such as cannabis and hemp, which can be damaged by over drying during a pasteurization process. The unit and methods of the disclosure further utilize a rapid cooling of the pasteurized product after the pasteurization cycle to quickly remove heat from the product and reduce the exposure time to heat, which could be damaging to products, such as cannabis and hemp. The pasteurization unit and methods of the disclosure therefore can be gentler on the product, particularly cannabis and hemp products, which can be particularly sensitive to external stimuli by not only maintaining suitable heating levels, but reducing the time at which buds are exposed to the heat and limiting he time residual heat remains in the buds after the pasteurization cycle. The pasteurization units and methods of the disclosure can also allow for pasteurization of the product in loose form, without having to first contain the product in a pouch.

Pasteurization units of the disclosure can generally include a product loading area for introducing product into a first chamber 20 for pasteurization. The product loading area can be a hopper that is in communication with the first chamber 20. The product loading area can be an area for receiving a product cartridge 12 as detailed below. Such product cartridge 12 can be loaded separate from the pasteurization unit and then attached to the pasteurization unit to allow for introduction of the product within the cartridge 12 into the first chamber 20. The pasteurization unit can then include a second chamber 22 downstream of the first chamber 20, such that product can flow into the second chamber 22 for cooling. Alternatively, the first chamber 20 can be used for both pasteurization and cooling. Product can be removed from the pasteurization unit after cooling through a product outlet. The product outlet can be in communication with a product receiving tray or a hopper can be provided for transferring product from the pasteurization unit to an inline packaging unit.

While arrangements are generally discussed herein as a vertical alignment of chambers and assemblies, such that the product passes through the first chamber to the second chamber along a vertical transport path, horizontal arrangements are also contemplated herein. Combinations of horizontal and vertical transport paths can also be contemplated herein. For example, a horizontal transport path can be achieved using a conveyor system in which a chamber is transferred between different zones for pasteurization and cooling. The chamber can be adapted, for example, to connect to assemblies in each zone to provide for the introduction of vapor or cryogenic fluid. Use of conveyors and indexers for transport of the product to the pasteurization unit or between the first and second chambers are also contemplated herein. For example, the product can be transported to the product inlet of the first chamber using an indexer system.

Figures 15A, 15B, 15C, 15D:
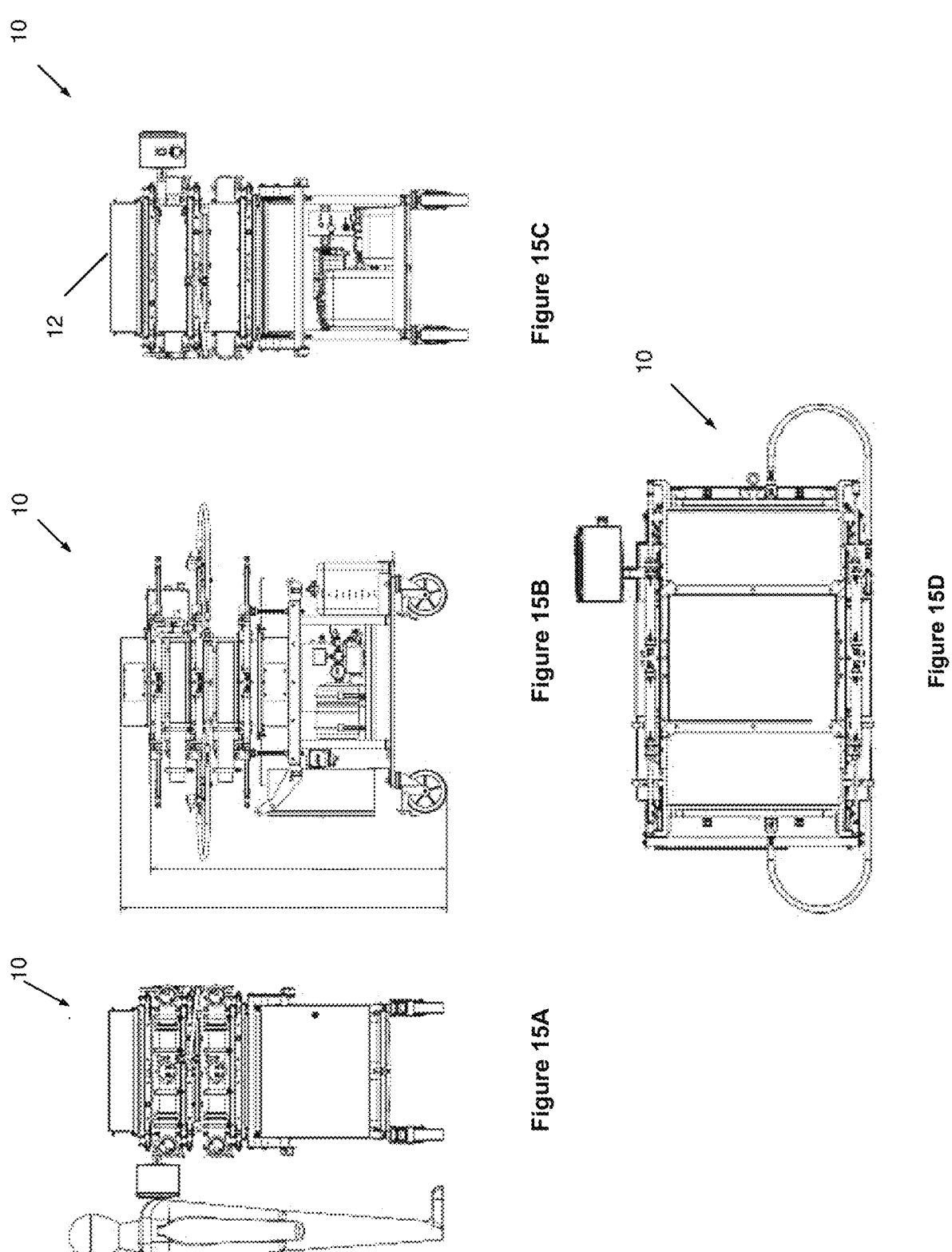
Figure 26A:
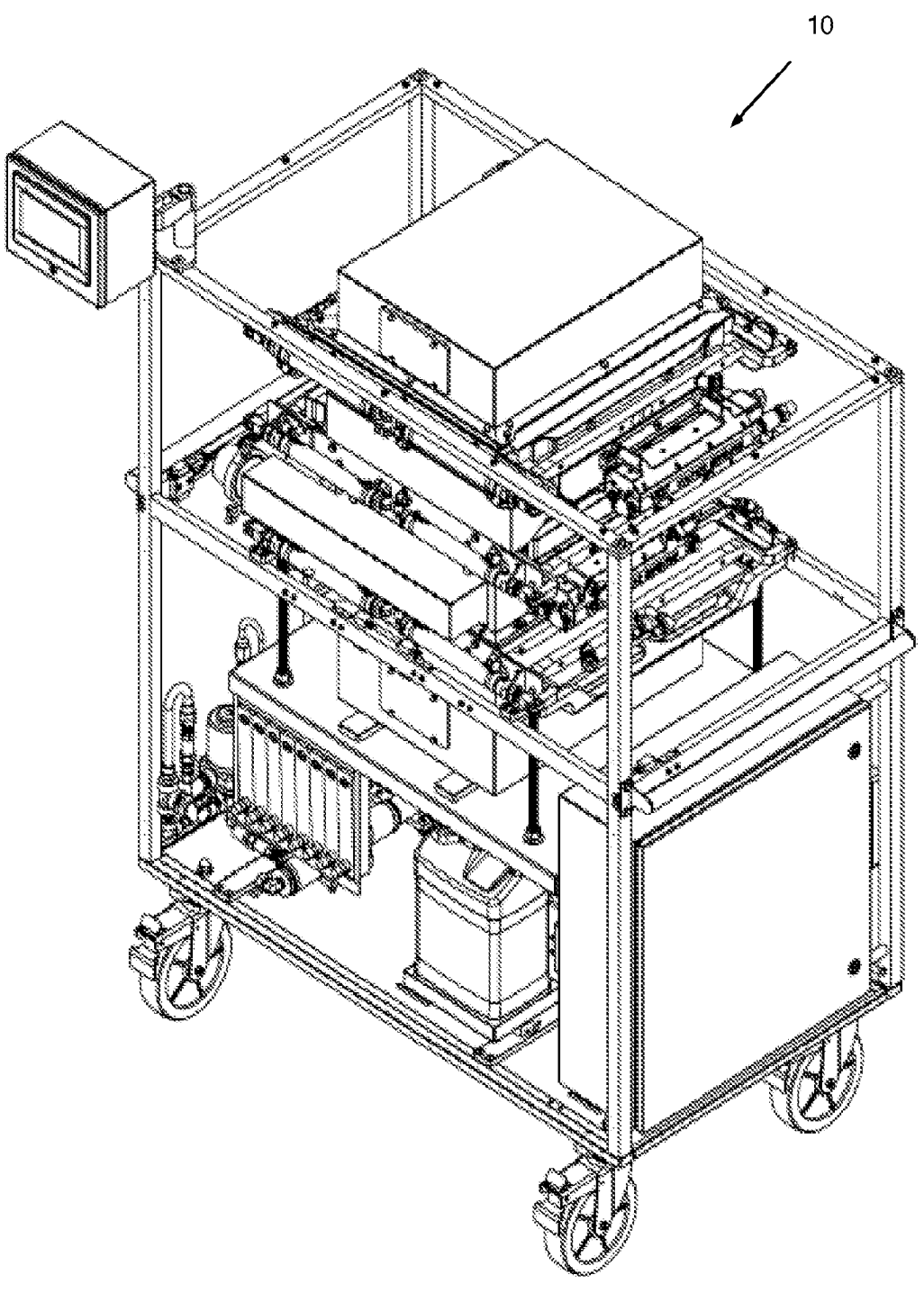
FIGS. 26A and 26B are schematic illustrations of various views of a pasteurization unit in accordance with the disclosure.
Figure 26B:
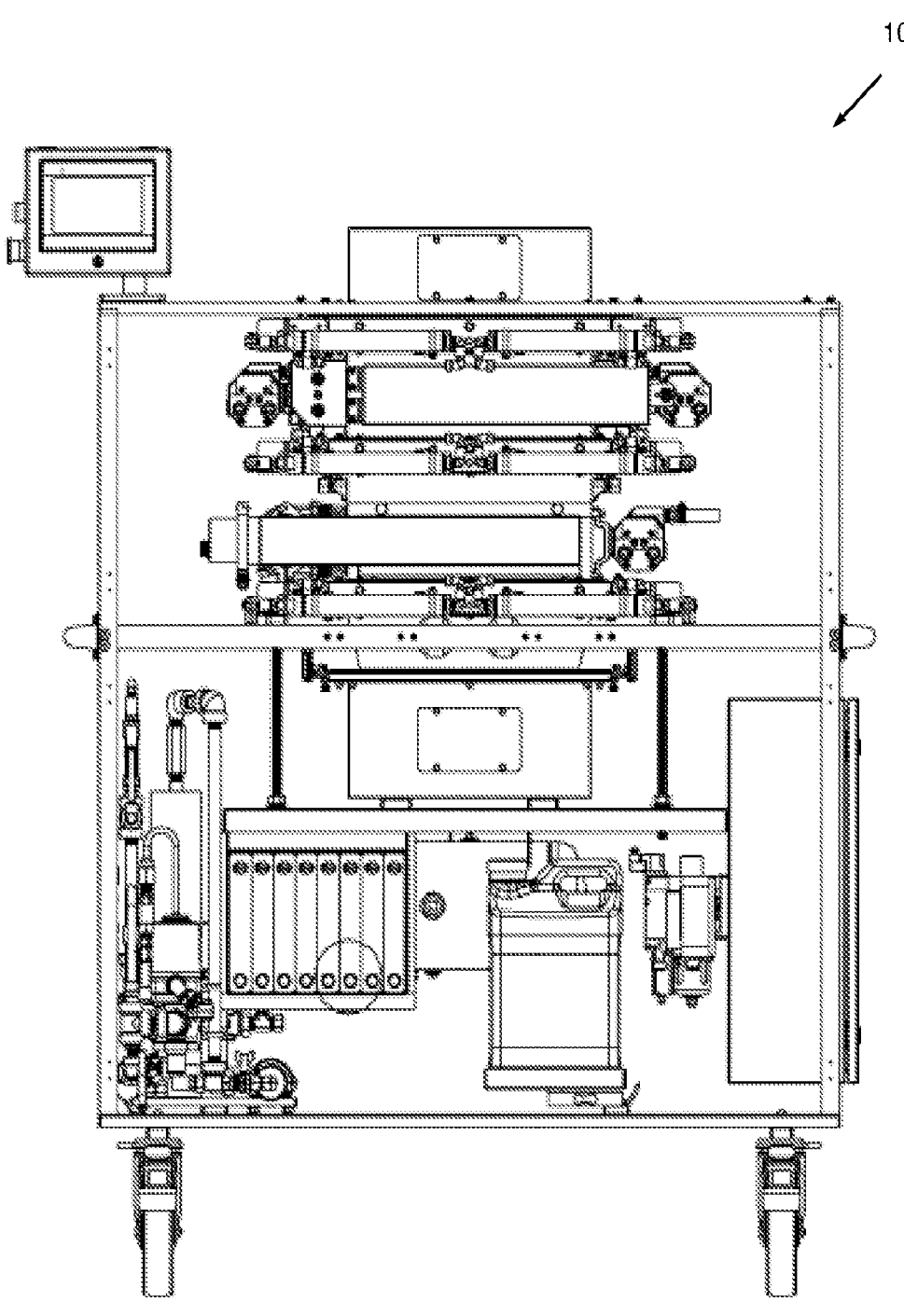
Figure 27A:
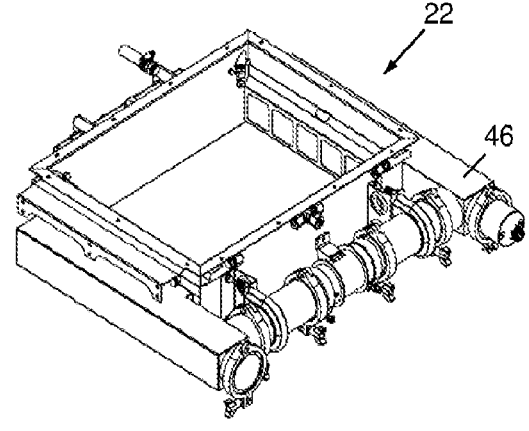
FIGS. 27A to 27D are schematic illustrations of various views of a second chamber in accordance with the disclosure.
Figure 27B:
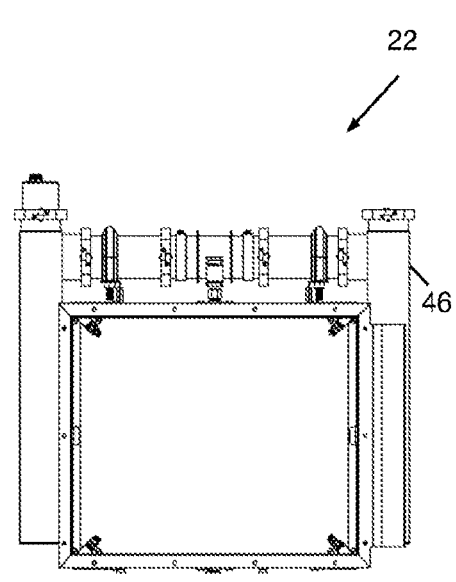
Figure 27C:
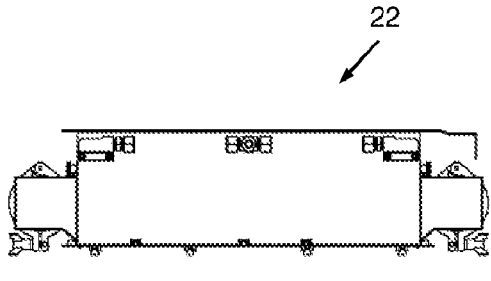
Figure 27D:
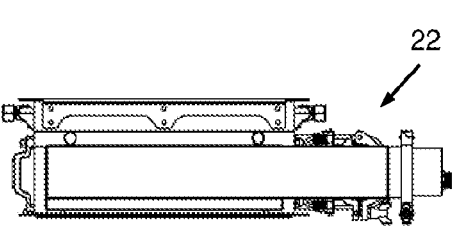

FIG. 1 illustrates a pasteurization unit of the disclosure in-line with a packaging unit. FIG. 15 illustrates a pasteurization unit of the disclosure without a packaging unit. The pasteurization unit of FIG. 15 illustrates a vapor generating system arranged below the pasteurization unit and in fluid communication with the chamber for pasteurization. While FIG. 15 illustrates the vapor generating system on a lower level of a cart beneath the pasteurization unit arranged on top of the cart, other arrangements are also contemplated herein. For example, the vapor generating system can be on the same supporting surface as the pasteurization unit or arranged above the pasteurization unit or on a surface entirely separate from the pasteurization unit, but fluidly connected thereto. FIG. 26 illustrates a pasteurization unit with vapor generating systems arranged in line with the pasteurization chamber. For example, the vapor generating systems can be attached to the pasteurization chamber. Other arrangements with vapor generating systems can also be used. Any number of vapor generators can be included in the vapor generating system. For example, FIG. 24 illustrates an embodiment in which two vapor engines are arranged in the pasteurization chamber. Pasteurization units of the disclosure can include water containers for providing a water source for the vapor generator. Alternatively or additionally, the pasteurization units of the disclosure can include connections for receiving water sources or being fluidly coupled with a water source or container. Pasteurization units of the disclosure can include a cryogenic fluid storage container or can be fluidly coupled to a cryogenic fluid container. For example, the pasteurization unit can include a solid state cryogenic system that can supply pure nitrogen gas to the vapor generator and/or the first chamber 20. The solid state cryogenic system can also be a source of cryogenic fluid to be supplied to the second chamber 22 during cooling.

Figure 2:
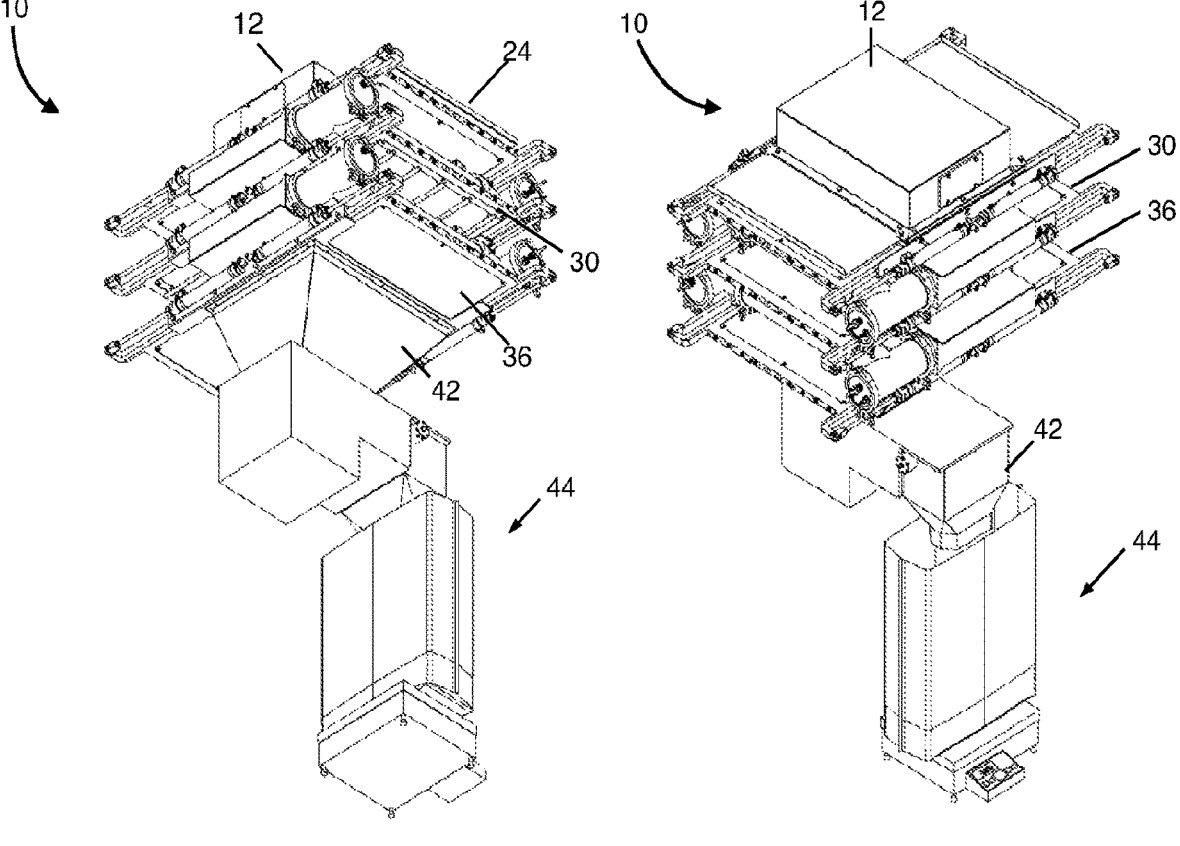
FIG. 2A is a front perspective view of a pasteurization unit and vibratory feeding and bagging system in accordance with the disclosure.
FIG. 2B is a rear perspective view of a pasteurization unit and vibratory feeding and bagging system in accordance with the disclosure.
Figure 3:
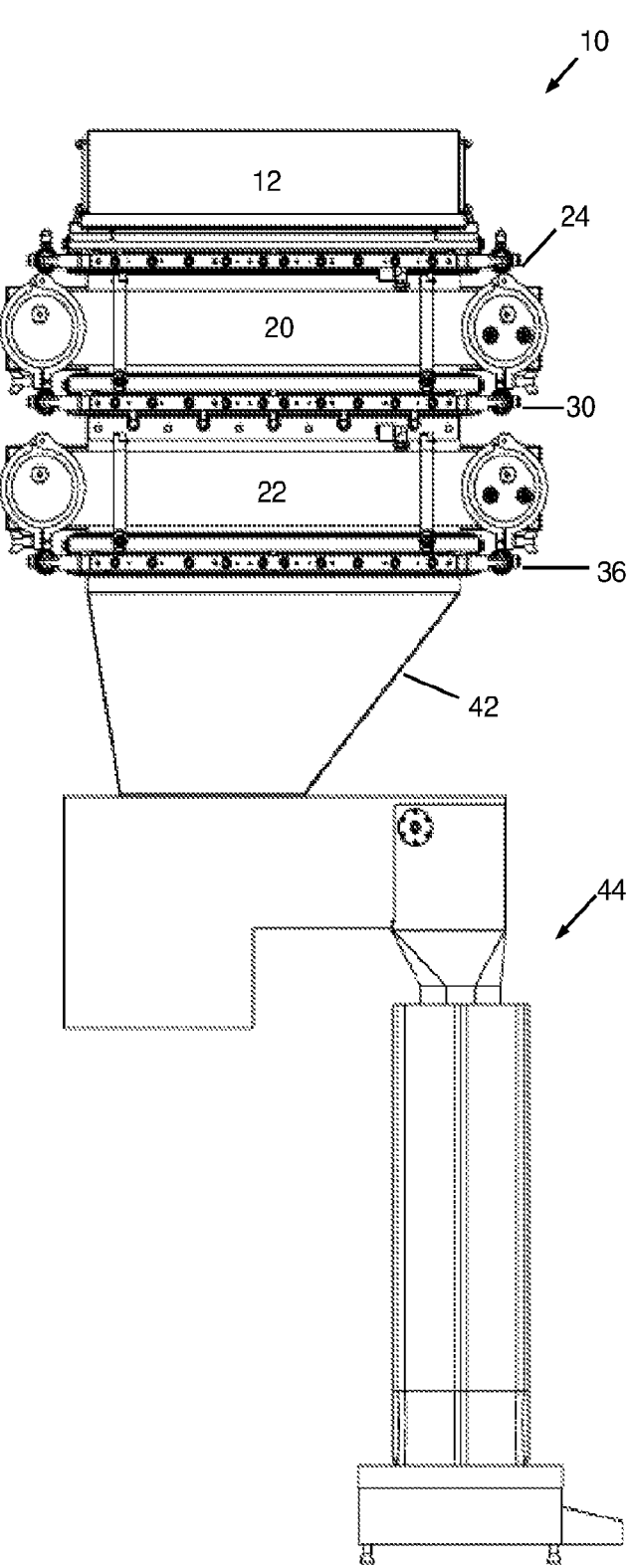
FIG. 3 is a side view of a pasteurization unit and vibratory feeding bagging system in accordance with the disclosure.
Figure 4:
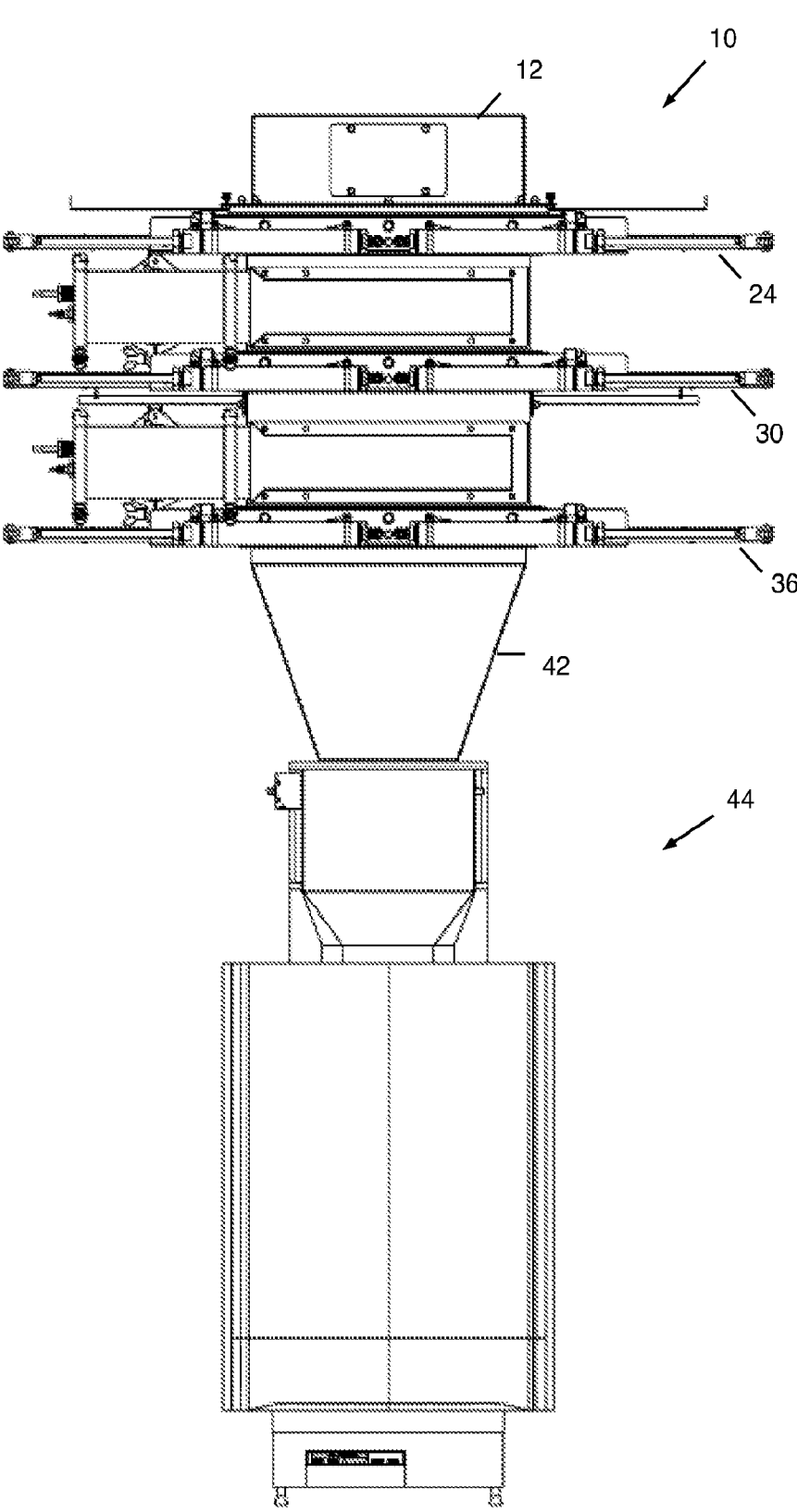
FIG. 4 is a front view of a pasteurization unit and vibratory feeding bagging system in accordance with the disclosure.
Figure 5:
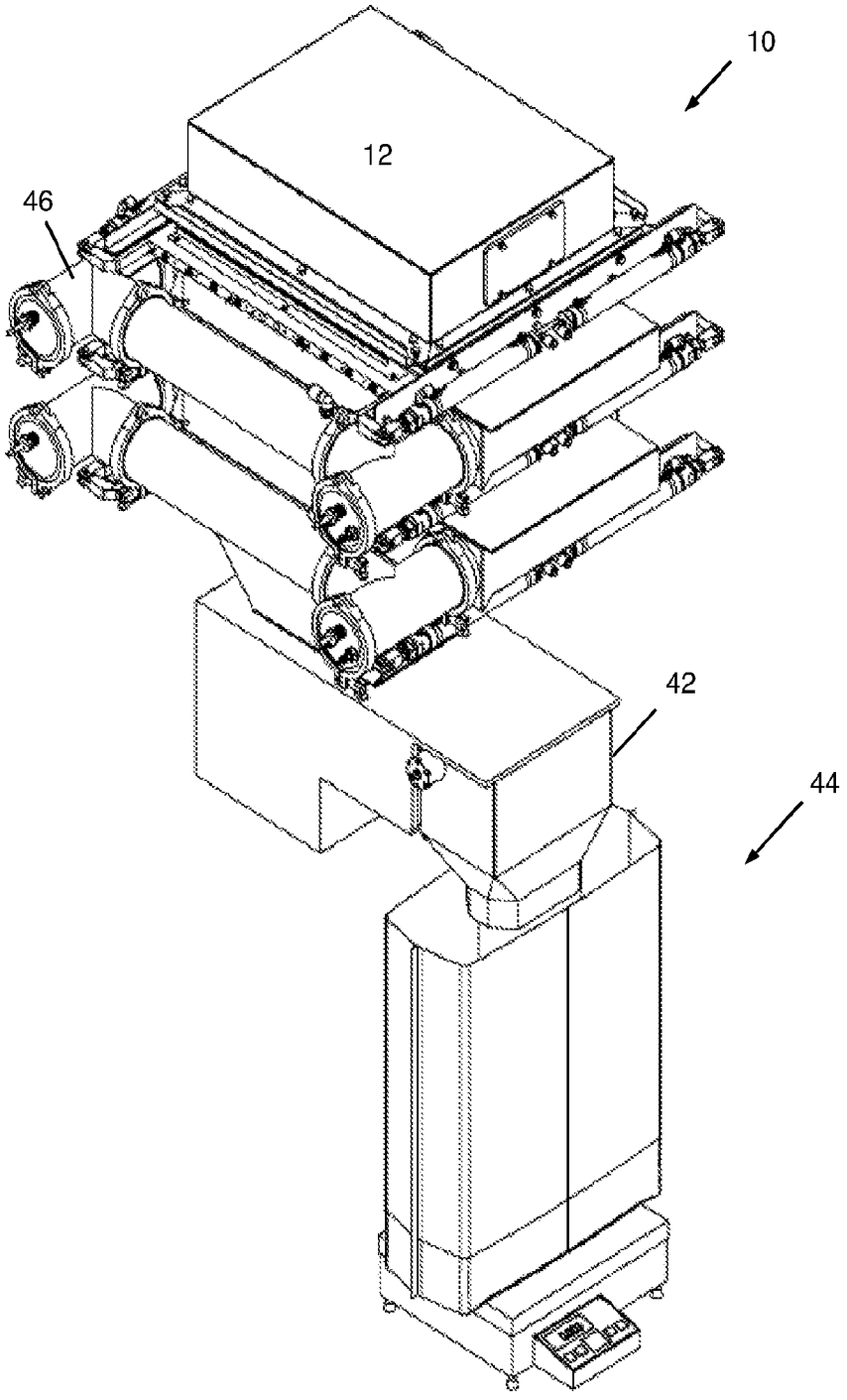
FIG. 5 is a side perspective view of a pasteurization unit and vibratory feeding bagging system in accordance with the disclosure.
Figure 6:
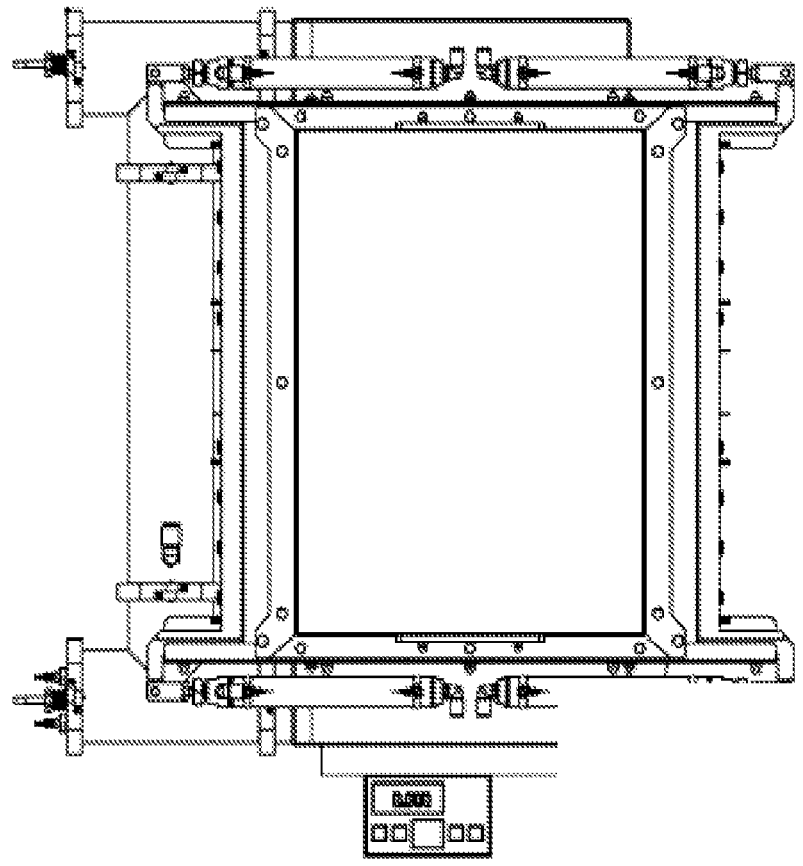
FIG. 6 is a top view of a pasteurization unit and vibratory feeding bagging system in accordance with the disclosure.
Figure 20:
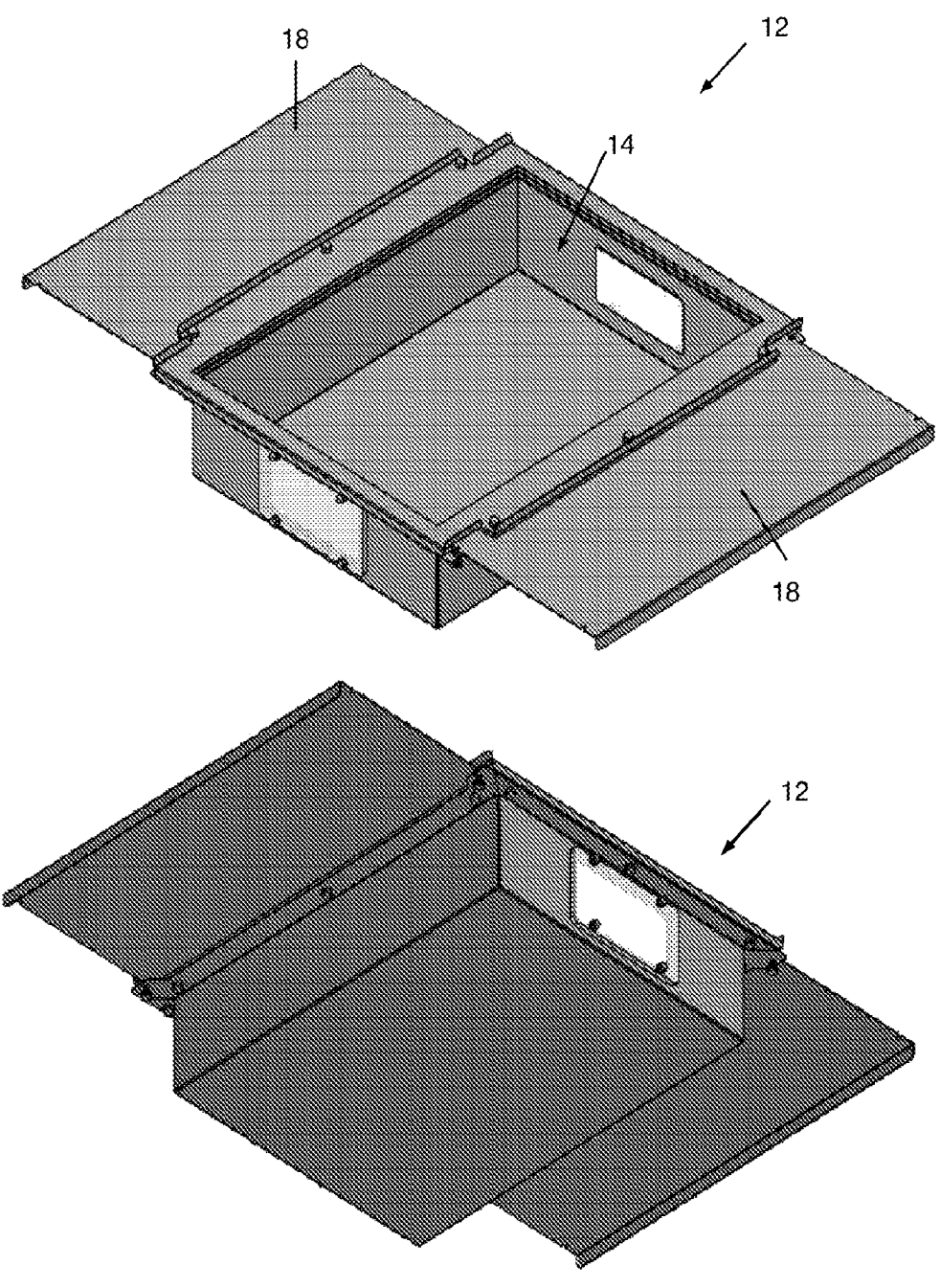
FIG. 20 is perspective views of a cartridge 12 for use with a pasteurization unit of the disclosure, showing the cartridge 12 in the open position.
Figure 23A:
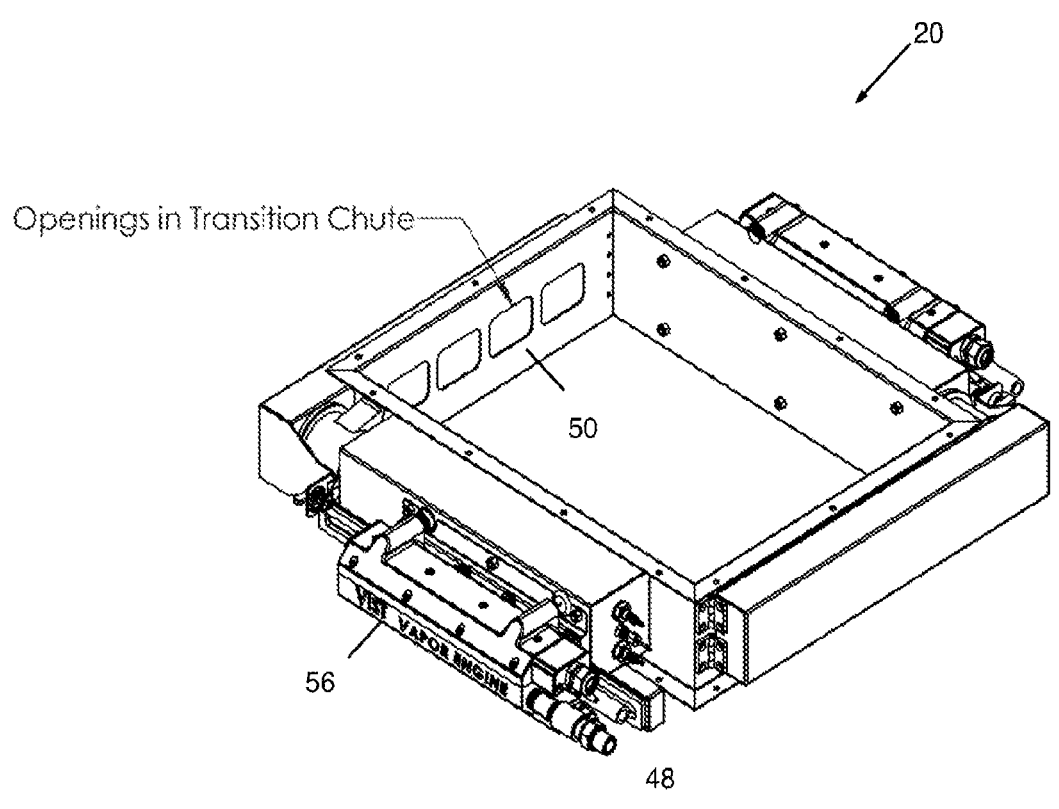
FIGS. 23A to 23F are schematic illustrations of various views of a first chamber in accordance with the disclosure, showing filter covers in the closed position.
Figure 23B:
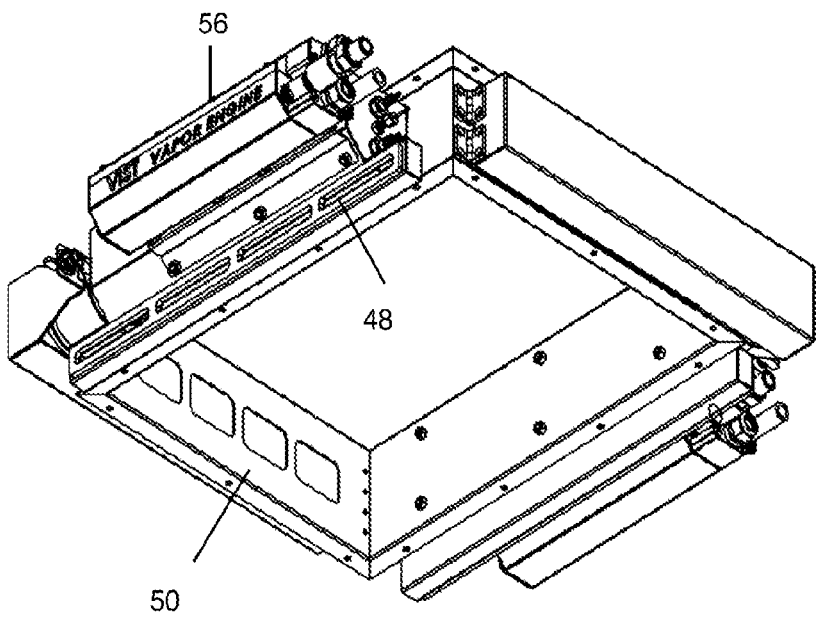
Figure 23C:
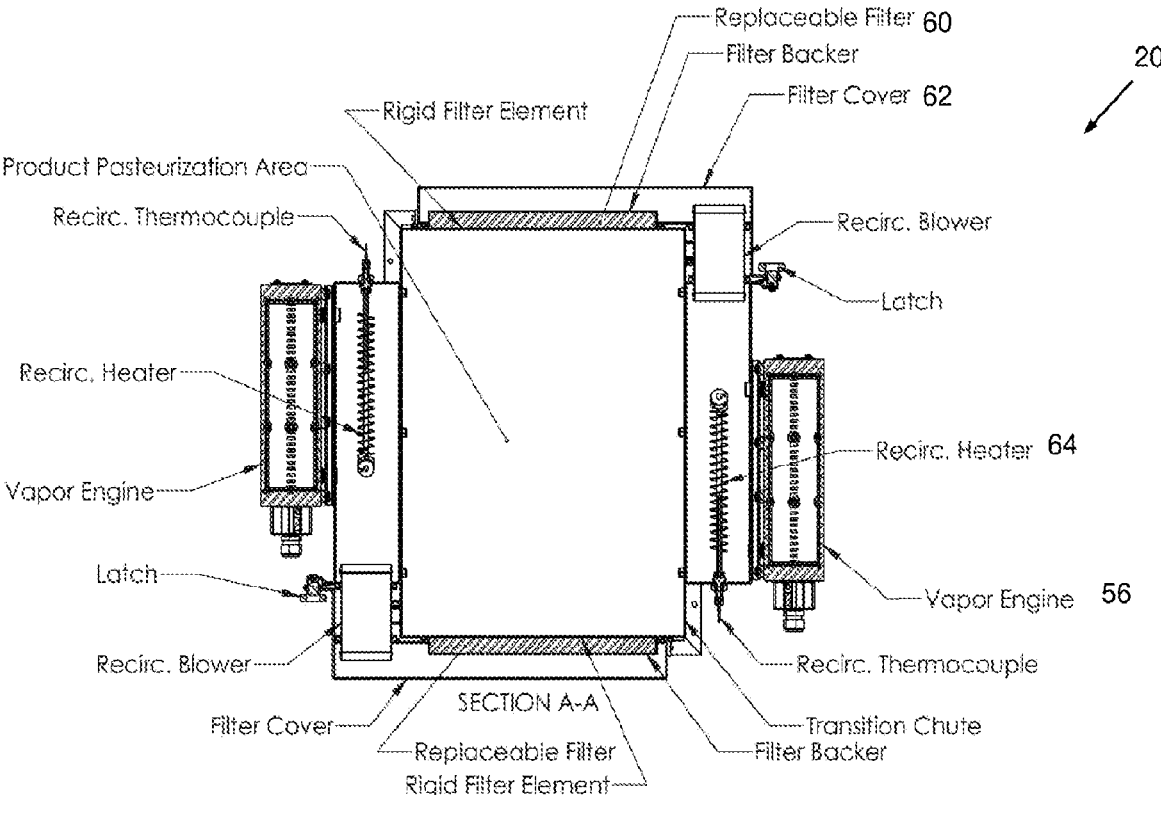
Figure 23D:
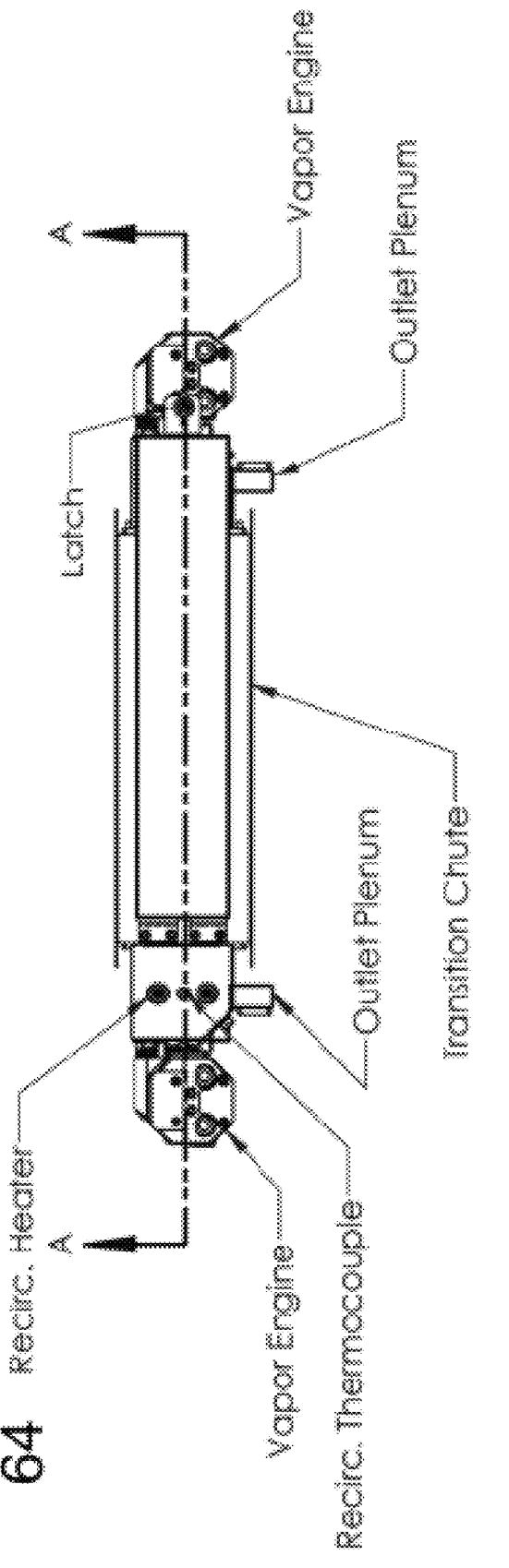
Figure 23E:
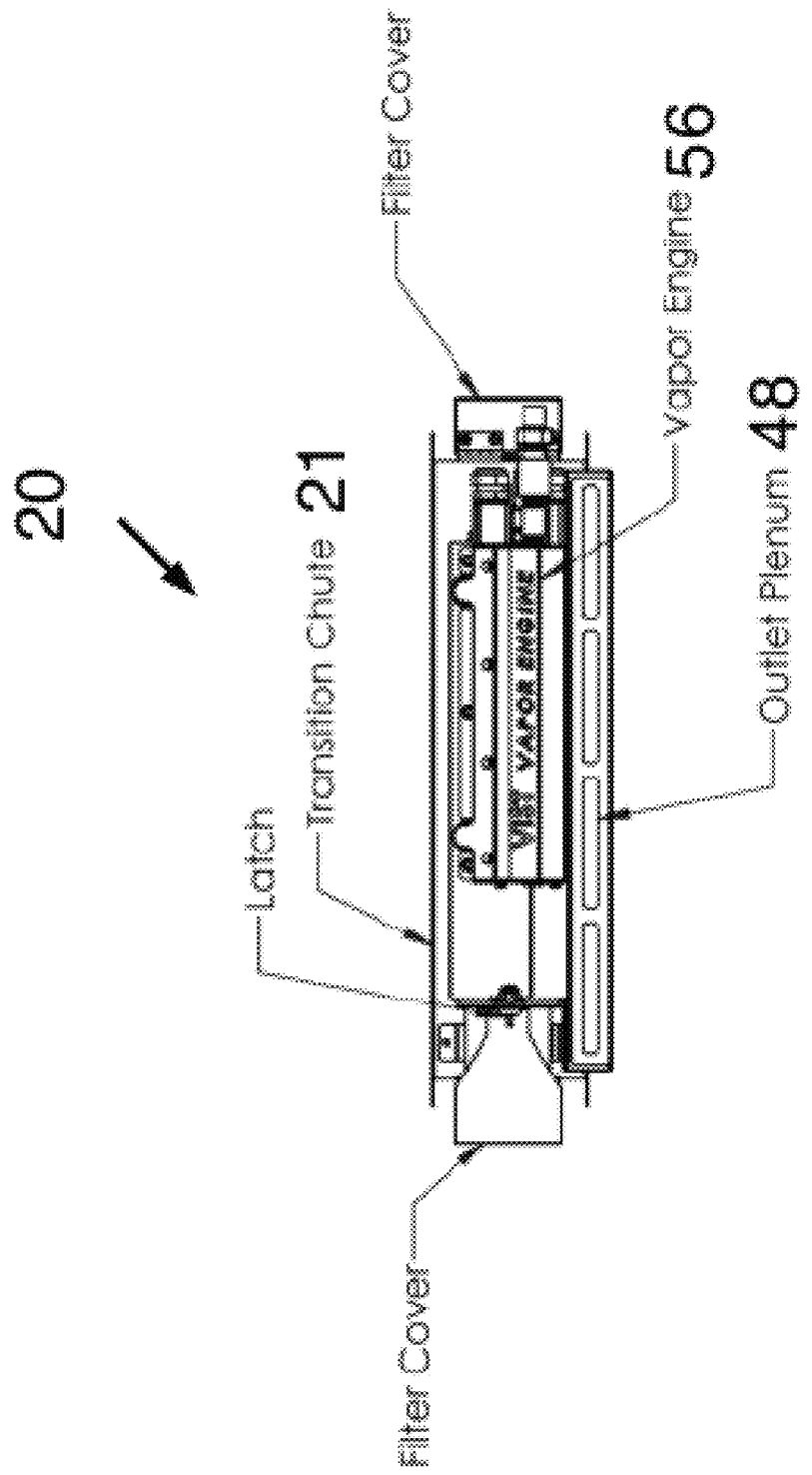
Figure 23F:
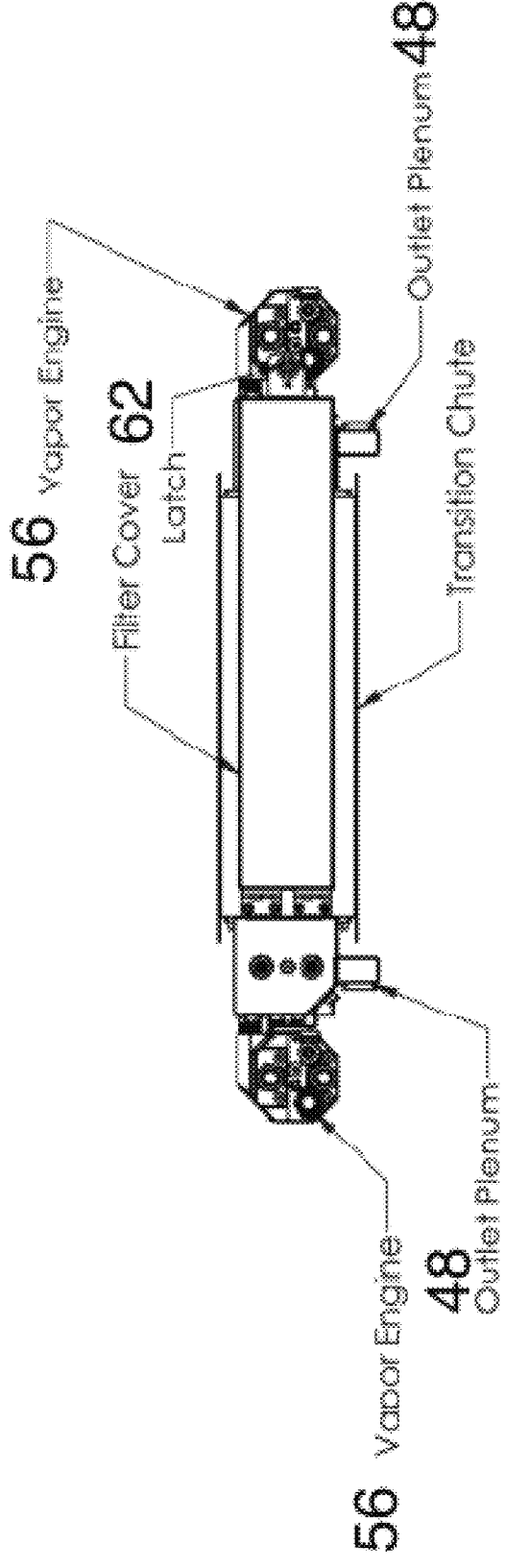
Figure 24A:
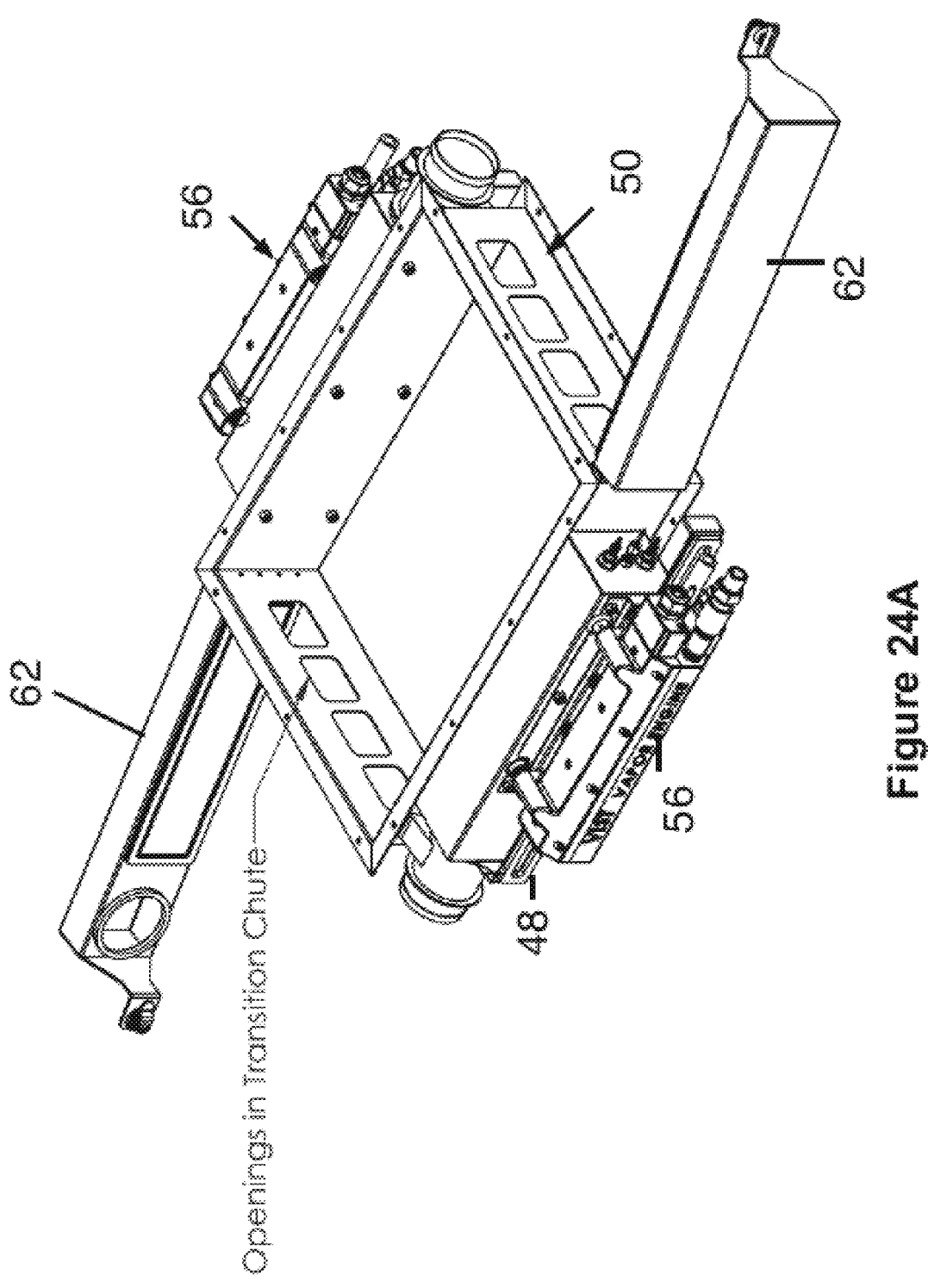
FIGS. 24A to 24E are schematic illustrations of various views of a first chamber in accordance with the disclosure, showing filter covers in the open position.
Figure 24B:
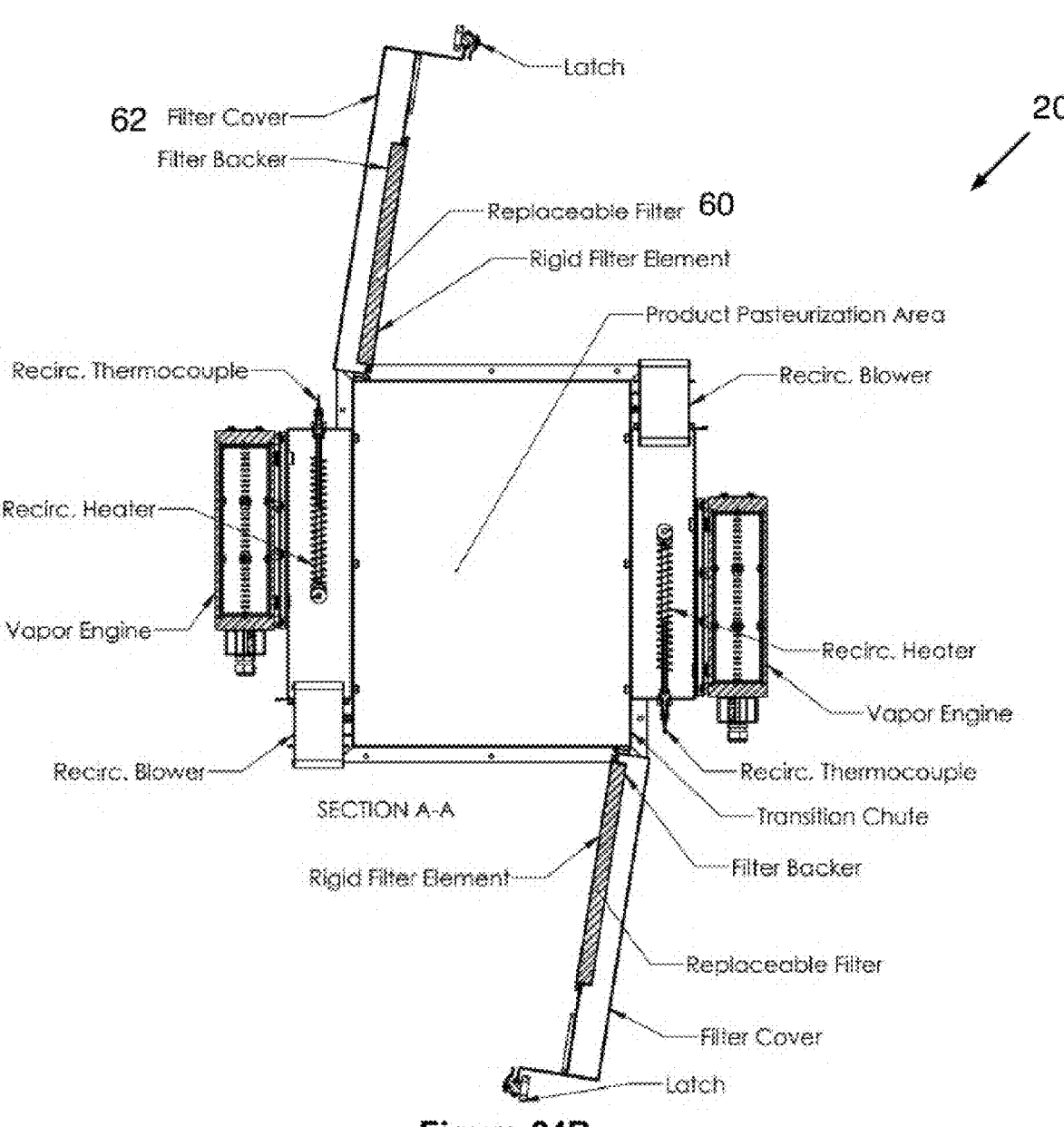
Figure 24C:
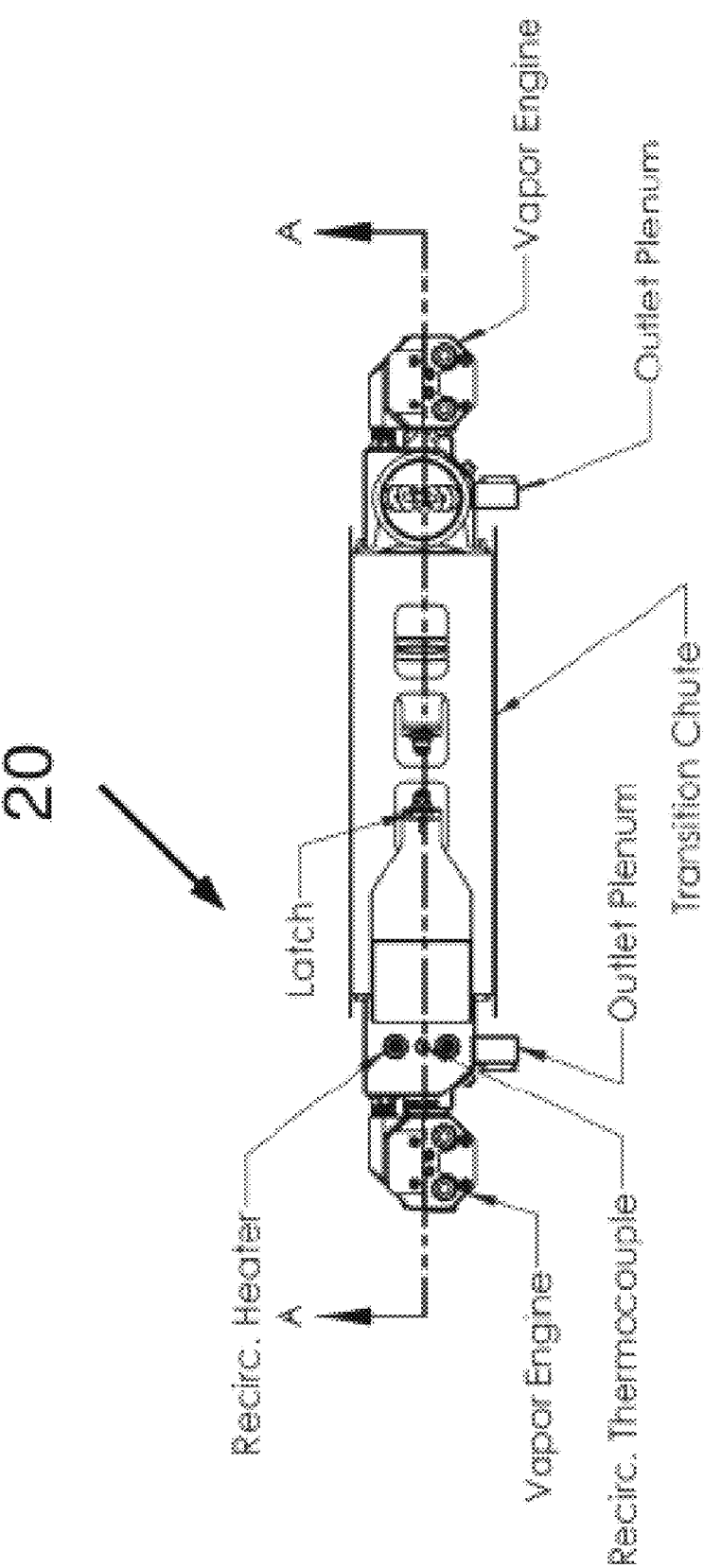
Figure 24D:
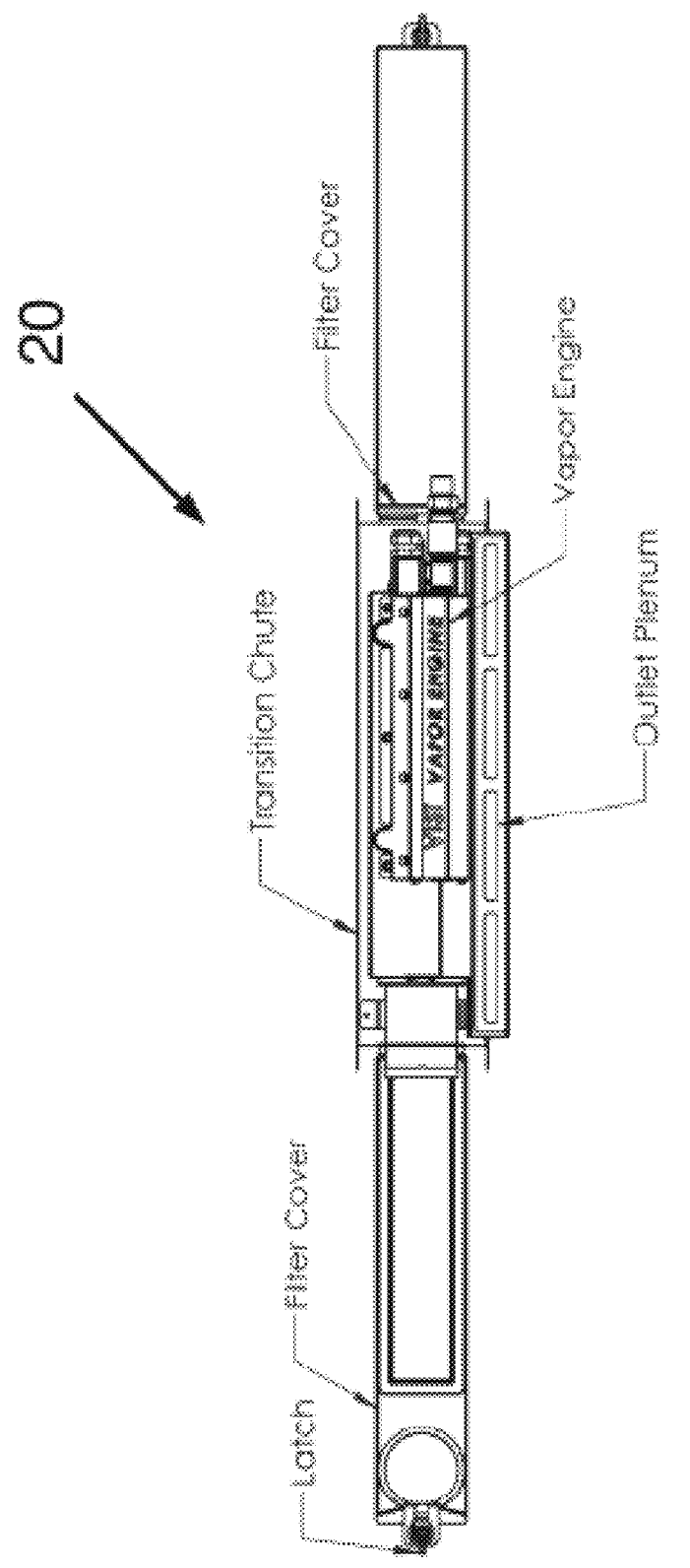
Figure 24E:
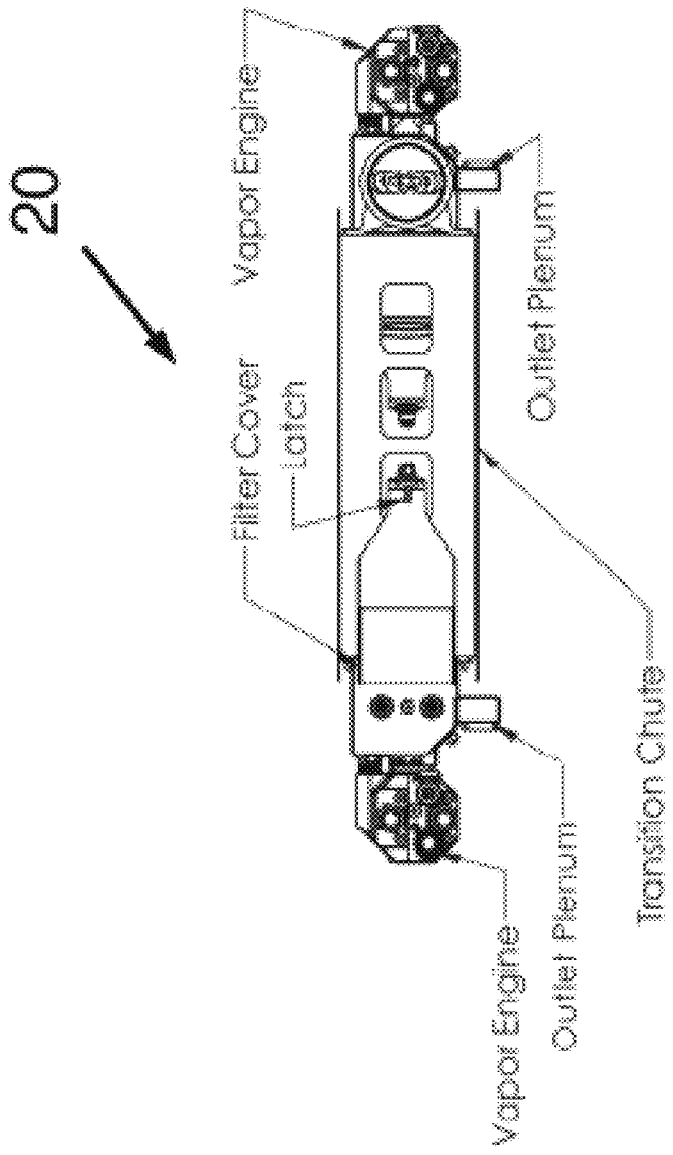

Referring to FIGS. 1 and 2, the pasteurization unit 10 can include a cartridge 12 into which the product to be pasteurized can be loaded. Other arrangements, such as a tray, hopper, or other loading apparatus can be utilized as an alternative to the cartridge 12. The input of unpasteurized product into the pasteurization unit, however provided, is generally referred to herein as the pasteurization input. The cartridge 12 can be detachable from the unit to allow for filling of the cartridge 12 away from the unit. This can make filling easier and can also allow for multiple cartridges 12 to be filled and waiting for pasteurization. This can result in a more efficient process, for example, by allowing of filling of a cartridge 12 while another cartridge 12 of product is processed on the unit. In arrangements in which the cartridge 12 is detachable from the unit, the unit can include rails or other mating structure that correspond to rails or other mating structure on the cartridge 12 to allow the cartridge 12 to be fixed onto the pasteurization unit through the mating structures. As described in detail below, the pasteurization unit can include a top assembly 24. The top assembly 24 can include the necessary rails or other mating structures and can allow for the cartridge 12 to be properly positioned so that product can flow from the cartridge 12 into the first chamber 20 when the opening in the top assembly 24 is exposed. Referring to FIGS. 20 and 21, the cartridge 12 can be provided with a door or moveable panel that covers an opening in the cartridge 12 and is movable to an open position in which the opening is exposed. The cartridge 12 can be filled through this opening and the opening can be closed over during transport, storage, and/or installation of the cartridge 12 onto the unit. Alternatively, the cartridge 12 can include oppositely disposed openings to allow for product to be loaded through a first opening and then introduced into the pasteurization unit through a second opening. The first opening can be covered by a hinged door, for example, to allow for easy access to the cartridge 12 interior for loading the product. The cartridge 12 can then be loaded on the pasteurization unit with the second opening facing and in communication with an opening in the first chamber 20 so product can be released from the cartridge 12 into the first chamber 20. The cartridge 12 can include one or more actuators or a manual or automatic system for opening and closing the panel over the opening when needed. Once installed on the pasteurization unit, the cartridge 12 doors can be opened while the top assembly 24 remains closed. The product would then rest against the top assembly 24 and be free to enter the first chamber 20, as detailed below, once the top assembly 24 is opened. The top assembly 24 can be provided with actuatable doors to control the exposure of the interior volume of the first chamber 20 for receiving the product from the cartridge 12. The cartridge 12 doors and the top assembly 24 can be connected or otherwise controlled to allow for opening of the cartridge 12 doors and top assembly 24 in a coordinated and automatic manner. For example, the cartridge 12 doors and the top assembly 24 can be controlled to be opened and closed substantially simultaneously.

The cartridge 12 is arranged at the upstream most end of the unit and is in fluid communication with the first chamber 20. In embodiments, the pasteurization unit can include separate chambers, first and second chambers 20, 22, for the heating and cooling processes, respectively. In other embodiments, the pasteurization unit can include a single chamber in which the heating and cooling is performed. In pasteurization units having only a single chamber, reference will be made herein to a heating/cooling chamber.

The chamber or chambers of the pasteurization unit each have an internal volume defined by a plurality of walls and product inlets and outlets for introducing and removing product from the internal volume. A single opening, for example, can serve as the product inlet an outlet. Alternatively, separately defined openings for the product inlet and product outlet can be provided. The first chamber 20 or each chamber can be provided with a product inlet, which is in fluid communication with an opening in the cartridge 12 (when present), and a product outlet. In embodiments of the pasteurization unit having two chambers, the product outlet of the first chamber 20 is in fluid communication with a second chamber 22 disposed downstream thereof. In embodiments of the pasteurization unit having only a single chamber, the product outlet of the chamber can be for removal of the product from the pasteurization unit and/or can be in fluid communication with a downstream packaging system or unit. The chamber or each chamber can be provided with a top wall having an opening thereby providing the product inlet 21 and a bottom wall having an opening therein to provide the product outlet 23. In some arrangements, the can be provided without top and bottom walls, such that open top and bottom regions of the first chamber 20 provides the openings for the product inlet 21 and product outlet 23 respectively.

As detailed below, in any of the arrangements having at least first and second chambers 22, the top assembly 24 can serve to seal over the first chamber 20 product inlet and the middle assembly 30 can serve to seal over the first chamber 20 product outlet. The top and middle assemblies can be controlled to open to allow flow of the product from the pasteurization unit inlet into the first chamber 20 and out of the first chamber 20, respectively. The product inlet and outlet can be provided in other ones of the walls of the first chamber 20 or through omission of other ones of the walls of the first chamber 20 other than the top and bottom walls. In such arrangements, the top and middle assemblies can remain disposed between the cartridge 12 or other pasteurization input and the first chamber 20 and the first chamber 20 and the second chamber 22, respectively.

In any of the arrangements having a single chamber, the middle assembly 30 can be omitted and the top and bottom assemblies can serve to seal over the product inlet and product outlets, respectively. The product inlet and outlet can be provided in other ones of the walls of the first chamber 20 or through omission of other ones of the walls of the chamber other than the top and bottom walls. In such arrangements, the top and bottom assemblies can remain disposed between the cartridge 12 or other pasteurization input and the first chamber 20 and the first chamber 20 and the second chamber 22, respectively.

The first chamber 20 or combined heating/cooling chamber is equipped with one or more heating units for conduction and/or convection and/or microwave heating, an inert gas input, and a vapor input. The vapor can be, for example, water vapor and/or steam. For example, the first chamber 20 or heating/cooling chamber can be heated using conduction and convection heating. Conduction or convection heating can be achieved, for example, using heating elements disposed on exterior surfaces of the chamber, arranged such that they transfer heat to the interior walls of the chamber. Alternatively, as detailed below, the top assembly 24 and/or the middle assembly 30 (when present) can be provided with the heating elements. In embodiments having the single chamber, the top assembly 24 and/or the bottom assembly 36 can be provided with heating elements. The first chamber 20 or heating/cooling chamber can further include one or more outputs for venting the vapor and/or the inert gas. For example, the first chamber 20 or heating/cooling chamber can include an output for the inert gas to allow the inert gas to be flowed through and recycled back into the chamber after it is re-filtered. The inert gas removed from the chamber can be passed through a filter arranged in fluid communication with the inert gas output, which can then flow the filtered inert gas back to an input of the first chamber 20. The filter can be, for example, a HEPA filter. The first chamber 20 or combined heating/cooling chamber can alternatively not rely upon recycled inert gas flow and can simply vent the gas as needed from the first chamber 20. For combined heating/cooling chamber embodiments, one or more cryogenic fluid inlets are arranged to direct a flow of cryogenic fluid into the chamber. The cryogenic fluid inlets such as described herein for the second chamber can similarly be used in a combined heating/cooling chamber.

In embodiments using separate heating and cooling chambers, the second chamber 22 is arranged downstream of the first chamber 20 and in fluid communication with the first chamber 20. The second chamber 22 has an internal volume defined by a plurality of walls. The second chamber 22 can be provided with a product inlet 25, which is in fluid communication with product outlet 23 of the first chamber 20, and a product outlet 27 through which product exits the pasteurization unit. The product inlets and outlets 25, 27 are sealable during cooling. The second chamber 22 can be provided with a top wall having an opening thereby providing the product inlet and a bottom wall having an opening therein to provide the product outlet. In some arrangements, the second chamber 22 can be provided without top and bottom walls, such that open top and bottom regions of the second chamber 22 provides the openings for the product inlet and product outlet respectively. As detailed below, in any of the arrangements of the second chamber 22, the middle assembly 30 can serve to seal over the second chamber 22 product inlet, as well as the first chamber 20 product outlet to isolate the first chamber 20 internal volume from the second chamber 22 internal volume during operation of either the first chamber 20 or the second chamber 22. The middle assembly 30 can be controlled to open to expose the product outlet of the first chamber 20 and the product inlet of the second chamber 22 to allow flow of the product from the first chamber 20 to the second chamber 22. A bottom assembly 36 can be provided downstream of the second chamber 22 product outlet to controllably seal over the product outlet. The bottom assembly 36 can be controlled to open to expose the product outlet of the second chamber 22 to allow the product to flow out of the pasteurization unit. The product inlet and outlet can be provided in other ones of the walls of the second chamber 22 or through omission of other ones of the walls of the second chamber 22 other than the top and bottom walls. In such arrangements, the middle and bottom assemblies can remain disposed between the first chamber 20 outlet and the second chamber 22 product inlet and at the second product outlet, respectively.

The second chamber 22 can include one or more inputs for receiving a cryogenic fluid. For example, the cryogenic fluid can be liquid nitrogen or other liquefied gas for rapid cooling. Additionally or alternatively, the middle assembly 30 and/or the bottom assembly 36 can be provided with the inputs 54 for receiving cryogenic fluid or otherwise providing the rapid cooling elements. The second chamber 22 can further include one or more vents or outlets. In some arrangements, the second chamber 22 can also include an inert gas input and output with or without the potential to filter and recycle the inert gas back into the second chamber 22.

In arrangements in which a single heating/cooling chamber is used, the chamber can include one or more inputs for receiving cryogenic fluid for rapid cooling. Additionally or alternatively, the top and/or bottom assembly 36 can be provided with the inputs for receiving cryogenic fluid or otherwise provide the rapid cooling elements. The inert gas inputs and outputs of the chamber can be optionally used during cooling to filter and optionally recycle the inert gas through the chamber.

In alternative arrangements, the second chamber 22 can be a blast freezer or can include equipment for blast freezing within the second chamber 22 and/or the middle assembly 30 and/or the bottom assembly 36. In arrangements having a single chamber, the heating/cooling chamber can be provided with equipment for blast freezing as an alternative.

A gate, door, or other closable opening is arranged between the cartridge 12 and the first chamber 20 to allow product to flow from the cartridge 12 into the first chamber 20, between the first and second chamber 22s to allow pasteurized product follow to the second chamber 22 for rapid cooling, and at the bottom of the second chamber 22 to allow product to flow out of the pasteurization unit. The product can flow out of the pasteurization unit into a clean and/or sterile container and/or downstream system, such as a packaging system.

Figures 7D, 7E:
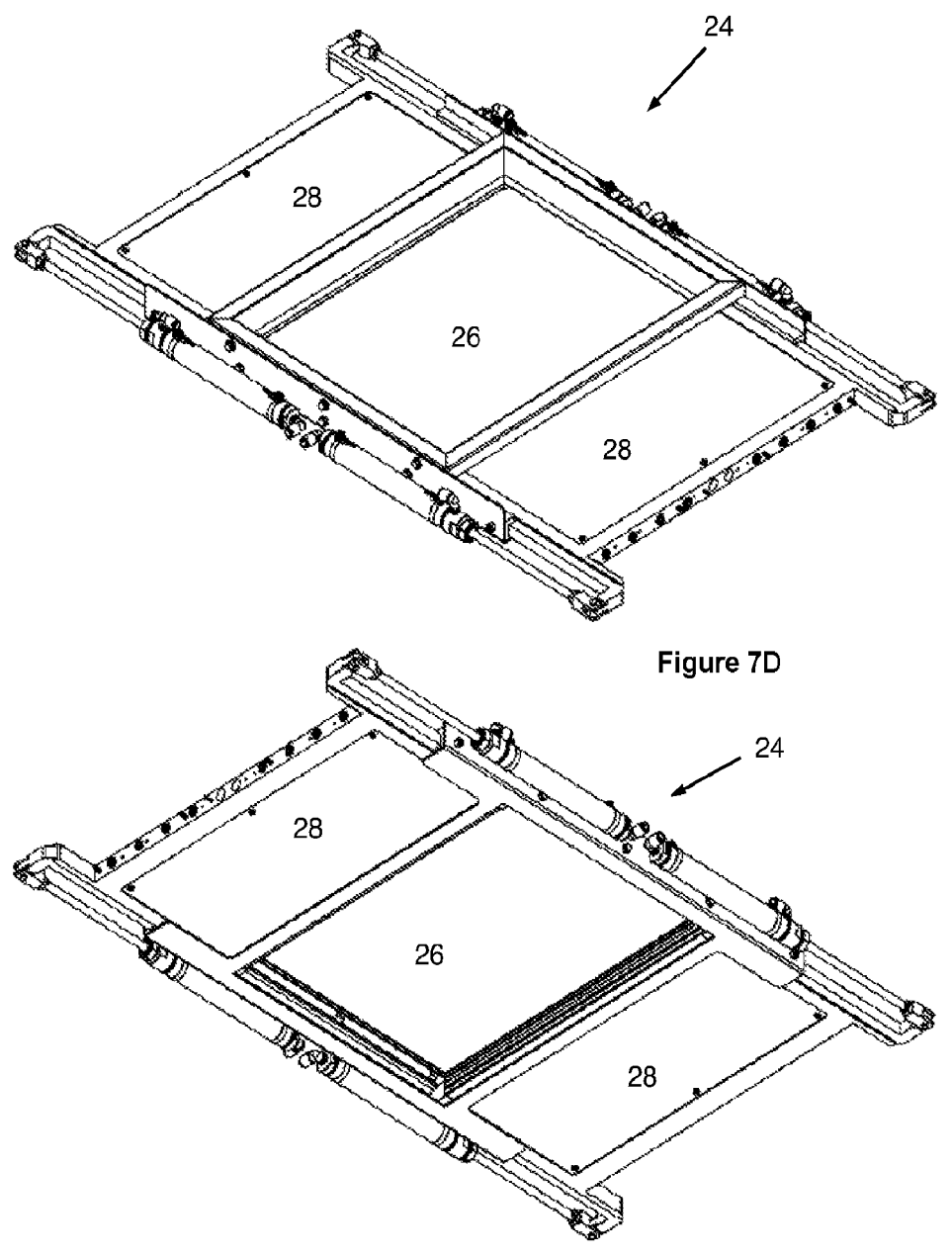
Figure 8A:
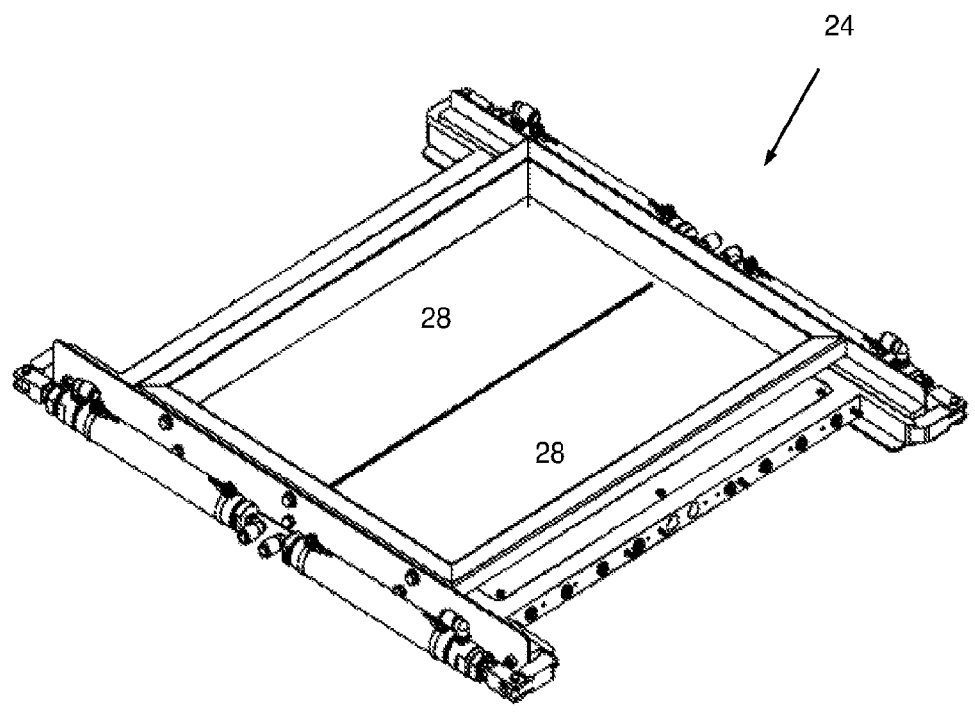
Figure 8B:
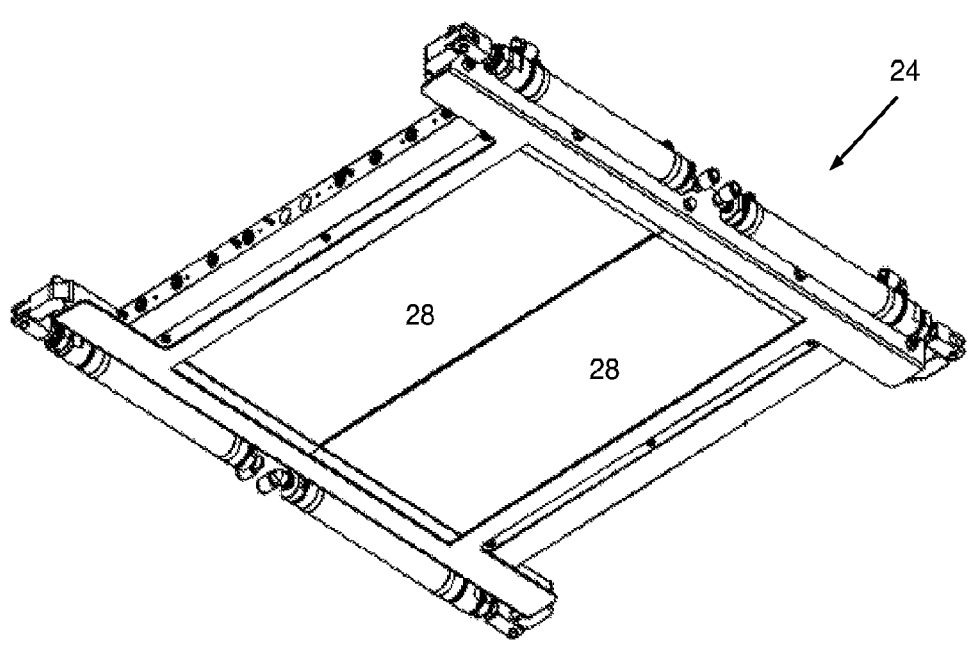

Referring to FIGS. 7 and 8, for example, the unit can include a top assembly 24 that includes an opening 26 and a panel, gate, door or other such structure 28 that is movable between closed position, in which the first chamber 20 is sealed from the cartridge 12, and an open position in which the top assembly 24 opening 26 is exposed to allow product to flow from the cartridge 12 (once positioned on the unit) into the first chamber 20. The panel 28 can be provided as a single piece that actuates at least to one side to expose the opening 26. Alternatively, the panel can be provided as a two-piece element, with each piece sliding in opposite directions to expose the opening. The panel(s) 28 can be actuated by one or more actuators. Alternative configurations for the panel or a door are also contemplated herein. For example, a panel that hinges to move away from the top assembly 24 can be provided as an alternative to a sliding panel. The top assembly 24 can include one or more heaters and/or one or more inert gas elements such that heat and/or inert gas can be directed into the interior volume of the first chamber 20 from the top assembly 24. For example, the top assembly 24 can include heater(s) and inert gas element(s) to generate a thermal flow from top assembly 24 to thereby provide convection heating.

The heating/cooling chamber or first chamber 20 and/or the top assembly 24 and/or the middle assembly 30 can include heating element(s) arranged such that uniform or substantially uniform temperature is achieved across the first chamber 20, including at the walls of the first chamber 20. In arrangements having the single heating/cooling chamber, the bottom assembly 36 can include heating element(s)

arranged such that uniform or substantially uniform temperature is achieved across the chamber. For example, the heating/cooling chamber or first chamber 20 can be provided with one or more heating elements arranged at one or more walls of the heating/cooling chamber or first chamber 20. For example, heating elements can be disposed at the top and bottom of the heating/cooling chamber or first chamber 20. For example, a heating element can be disposed in the top assembly 24. Additionally or alternatively, heating elements can be arranged at and/or in one or more of the sidewalls. In still further embodiments, heating elements can be arranged on exterior surfaces of the heating/cooling or first chamber 20.

Referring to FIG. 9, the first chamber 20 can include a circulation unit 46. Such a circulation unit 46 could also be provided in a heating/cooling chamber for pasteurization units having a single chamber. The circulation unit 46 is in fluid communication with the vapor generator and/or inert gas source. The circulation unit can have, for example, an inlet for receiving vapor and/or inert gas from the vapor generator or have separate inlets for vapor and for inert gas. The circulation unit 46 includes a channel through which the vapor and/or inert gas is flowed and directed to a circulation unit 46 outlet 48. The circulation unit outlet 48 can be direct communication with the internal volume of the first chamber or can be in fluid communication with one or more inlets on the middle assembly as detailed below. The circulation unit can include a blower in the channel for directing flow of the vapor and/or inert gas through the channel and ultimately into the first chamber. The first chamber includes an outlet into which the inert gas and/or vapor is flowed after flowing through the first chamber 20 and circulation unit 45 can be in fluid communication with this gas outlet such that the vapor and/or inert gas removed from the first chamber 20 can be recycled through the circulation unit 46. The circulation unit 46 can be arranged such that flow input (from the circulation unit outlet) and the flow output (from the first chamber 20 gas outlet) are at opposed ends of the first chamber 20. For example, the input can be at the top of the chamber and the output at the bottom of the first chamber 20 or vice versa. Alternatively, the inputs and outputs can be arranged at opposed side walls. The first chamber 20 can include one or more circulation unit 46s. In some arrangement, the circulation unit 46 can be for inert gas and an include a pipe, tube, or other such structure that fluidly connects the input and output and a filter can be arranged in the pipe, tube, or other structure to filter the inert gas received from the output and recycle it back to the input for use again in the first chamber 20. The circulation unit 46 can further include a heater such that when inert gas is flowed from the circulation unit 46 into the first chamber 20, convection heat is also generated.

Figures 16A, 16B, 16C, 16D, 16E:
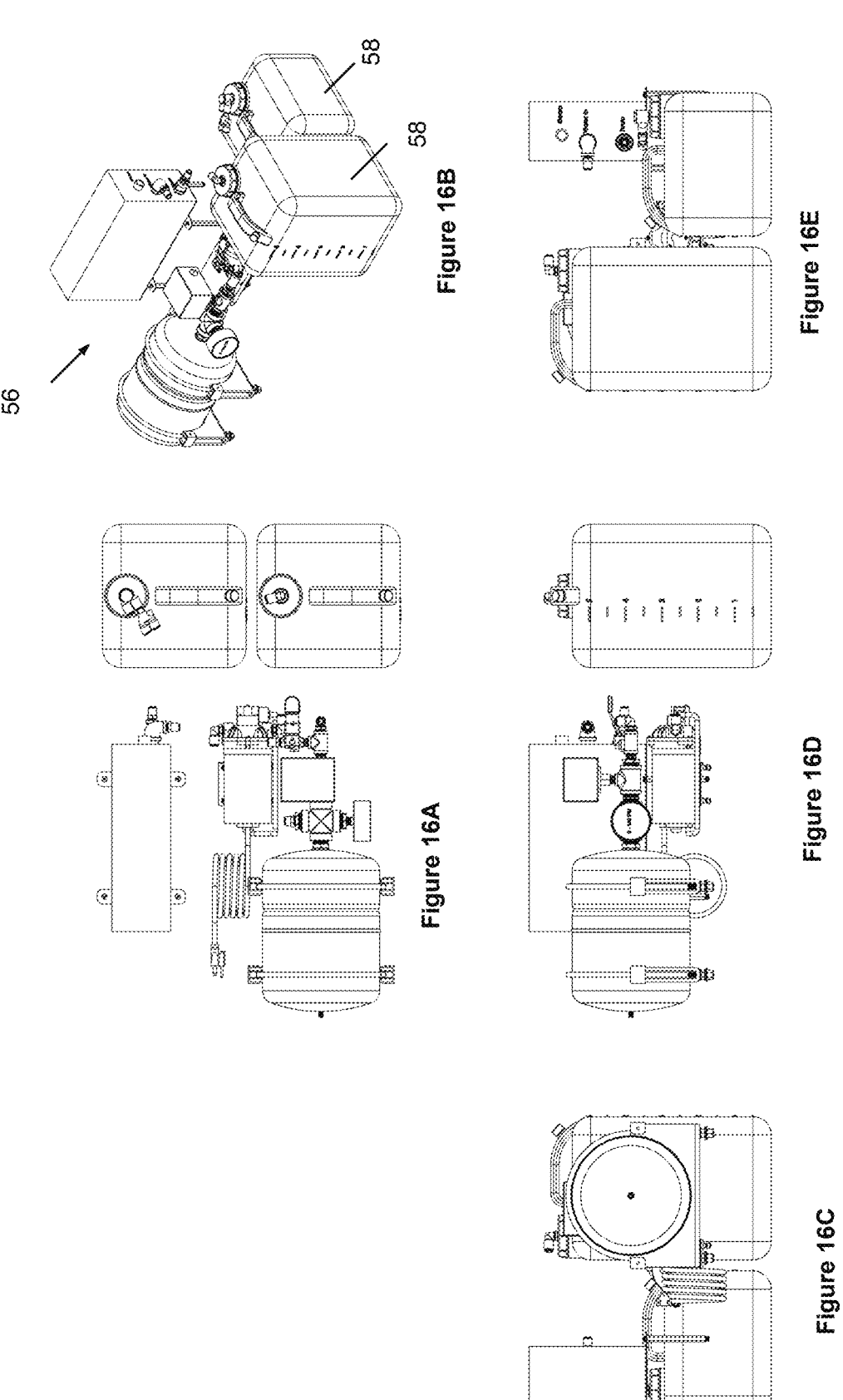
FIG. 16A-16G are various views of a vapor generator and water supply system for use with a pasteurization unit of the disclosure.
Figure 16G:
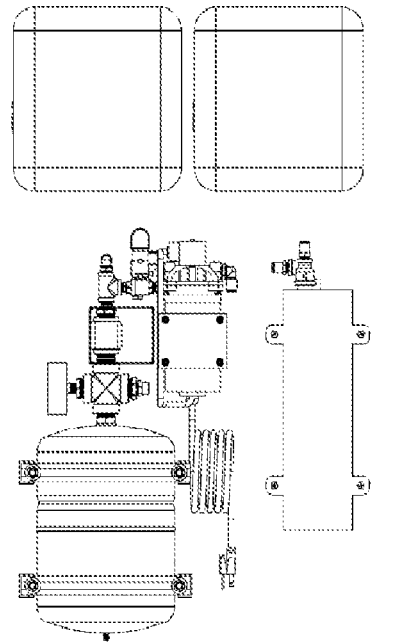
Figure 16F:
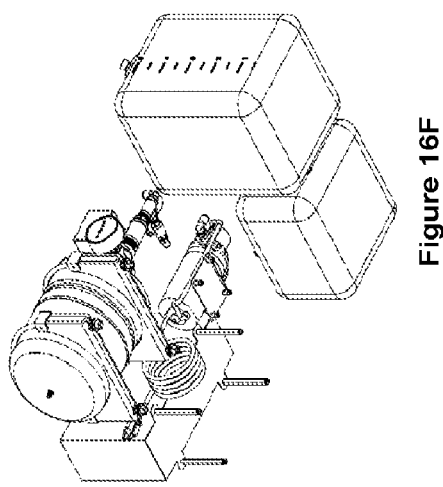

The first chamber 20 or heating/cooling chamber can further include an injection port for injection of the vapor into the first chamber 20 from a vapor injector arranged outside of the first chamber 20 or heating/cooling chamber. Additionally or alternatively, the injection port for the vapor can be provided in the top and/or middle assembly 30, and/or bottom assembly 36 (where a single heating/cooling chamber is used). The vapor injector or generator 56 can be separate from the pasteurization unit and fluidly coupled thereto. Alternatively, the vapor injector can be connected to the pasteurization unit. Any suitable apparatus for generating and injecting vapor can be used. FIG. 16 illustrates and example of a vapor generating system that can be used with the pasteurization units of the disclosure. The vapor generating system is fluidly couple to an inlet in the chamber and/or the door assembly to allow for the controlled flow of vapor into the chamber. In some arrangements the vapor can be introduced through the circulation unit 46. In other arrangements the vapor can be injected from one or more injection ports arranged in the first chamber 20 or heating/cooling chamber, the top assembly 24, and/or the middle assembly 30, and/or bottom assembly 36 (where a single heating/cooling chamber is used). For example, the injection ports can be arranged to provide a flow of vapor across the first chamber 20 or heating/cooling chamber from side wall to side and/or from top to bottom.

For example, referring to FIGS. 23 and 24, the first chamber 20 can include one or more vapor generators 56 arranged in fluid communication with a circulation unit 46 to circulate vapor through the chamber. The circulation unit 46 includes a channel 52 having an inlet 48 and one or more outlets 50 in fluid communication with the first chamber 20. The circulation unit 46 includes a blower for flowing inert gas and/or vapor through the channel and the first chamber 20. The circulation unit 46 can also include a heater.

The vapor can be mixed with an inert gas to control the humidity within the chamber. For example, the inert gas can be nitrogen. For example, the vapor can be mixed with the inert gas in the vapor generator or within the circulation unit 46. In the embodiment as illustrated in FIGS. 23 and 24, vapor from the vapor generator 56 is introduced into the circulation unit 46, which includes a blower 66 for flowing the vapor and/or inert gas into the first chamber 20. The circulation unit can directly flow the vapor and/or inert gas from the circulation unit 46 outlet into the first chamber 20. Alternatively, the circulation unit 20 can include an outlet plenum 48, with the blower directing the flow of vapor and/or inert gas out of the outlet plenum, which communicates with a plenum or other such structure on the middle assembly, such as shown FIG. 25, discussed in detail below. The vapor and/or inert gas exits the first chamber 20 through one or more outlets 50 provided in the chamber. The vapor exits the first chamber 20 and reenters the circulation unit 46 through filters arranged at the outlets. The collected vapor is cleaned of any contaminants, such as cellular material and other particulates, when passing through the filters and then reintroduced into the first chamber 20 through the circulation unit 46. The circulation unit 46 can include a heater for maintaining a constant temperature within the circulation unit 46.

The filters 60 in the circulation unit 46 can be, for example, HEPA filters. The circulation unit 46 can have an openable cover 62 to allow for access to the filter. The filter can then be replaceable. FIG. 24, for example, shows the filter assembly portion with the cover 62 open to allow for access to the filter elements 60. The filter 60 can include a rigid filter element and a replaceable filter element. Any known filter types and arrangements can be used.

In the embodiment shown in FIG. 23, two vapor generators and associated circulation units 46 are provided, with each providing flow into and out of opposed halves of the chamber. It is also contemplated herein to have a first chamber 20 with a single vapor generator and single circulation unit 46. Still further, it is contemplated herein that the vapor generator be in fluid communication with the circulation unit 46, but disposed away from the first chamber 20.

Figures 10D, 10E, 10F:
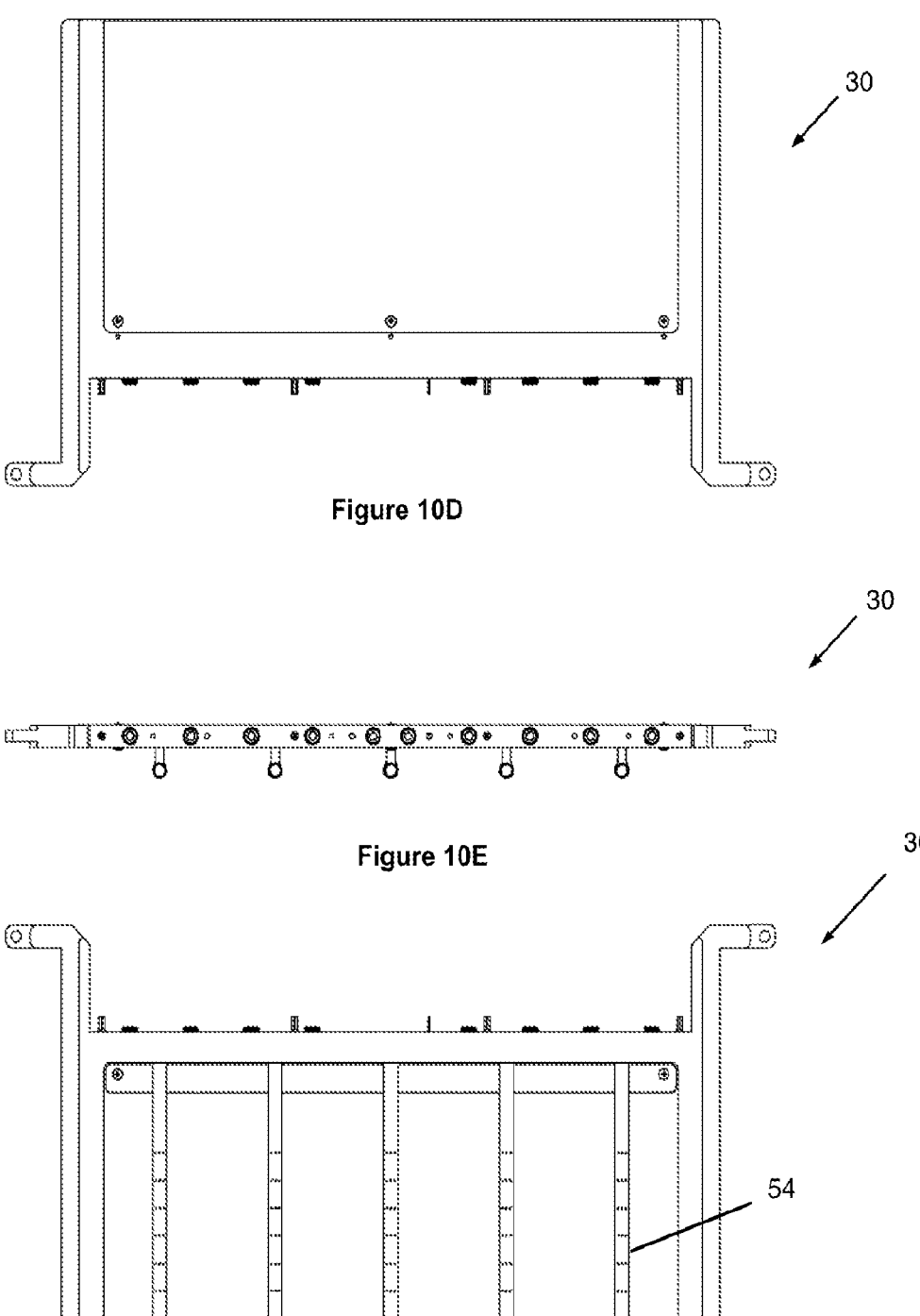
Figures 11A, 11B:
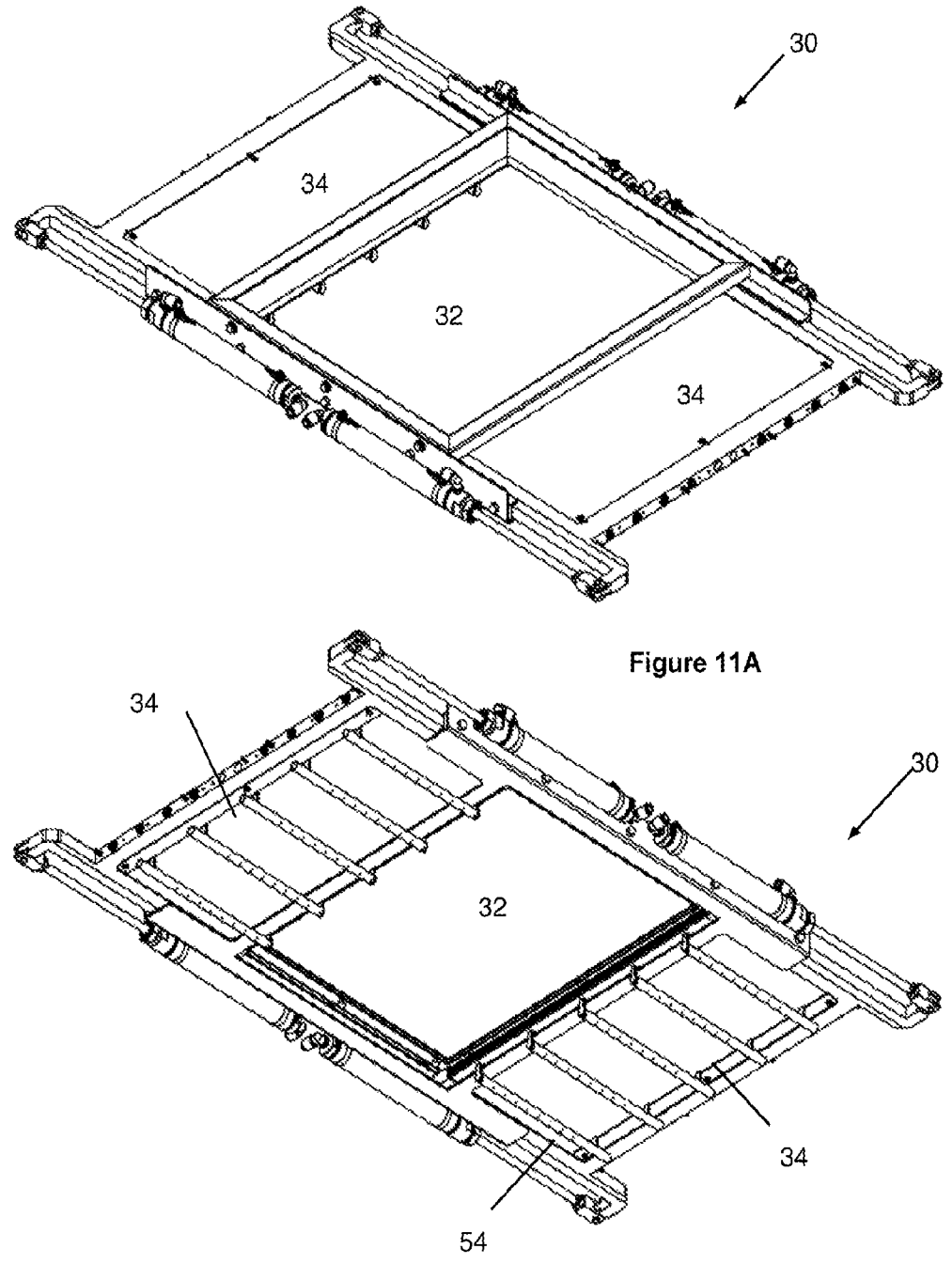
FIGS. 11A-11E are various view of a middle door assembly in accordance with the disclosure showing the assembly in the open position.
Figures 11C, 11D, 11E:
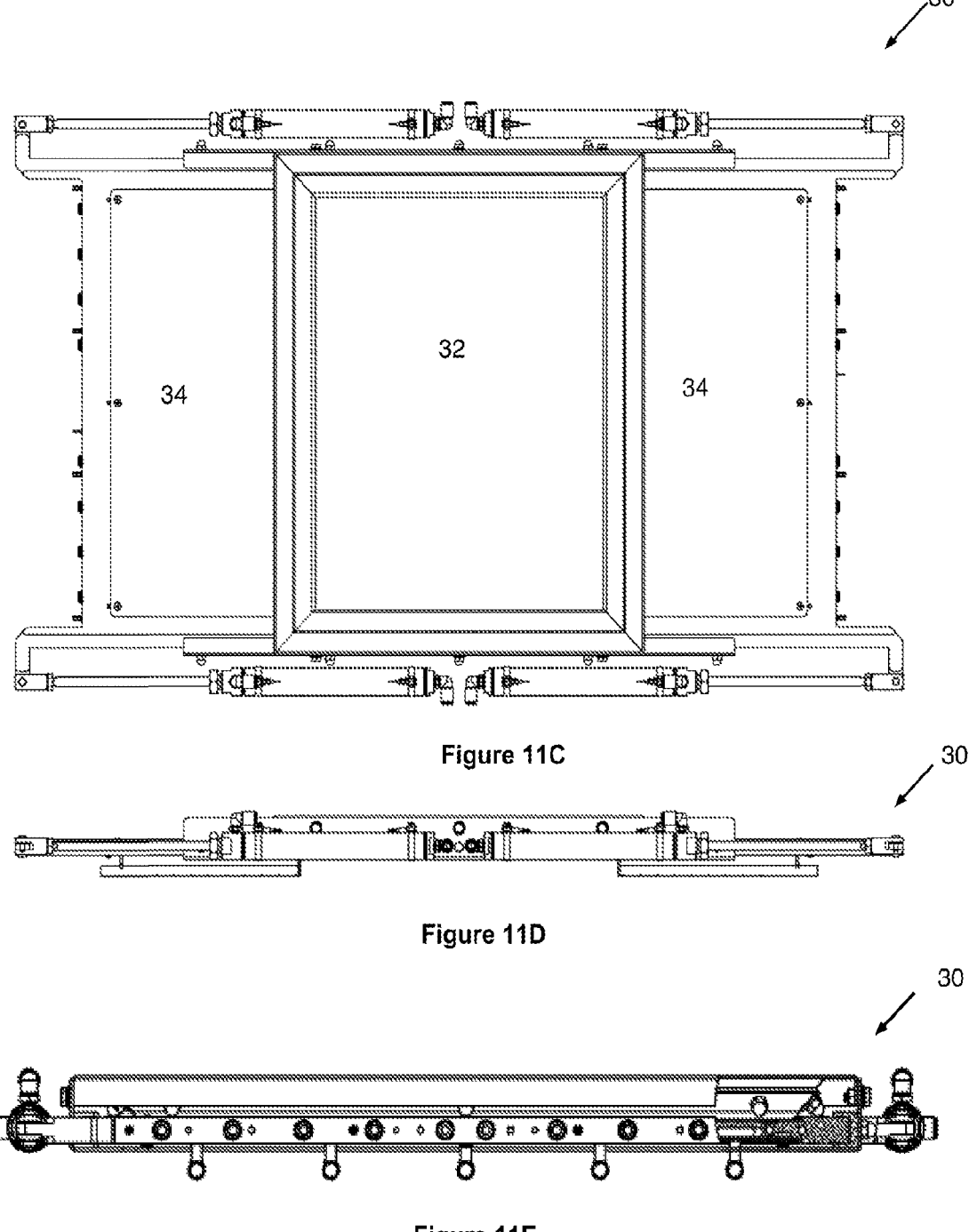
Figures 12A, 12B:
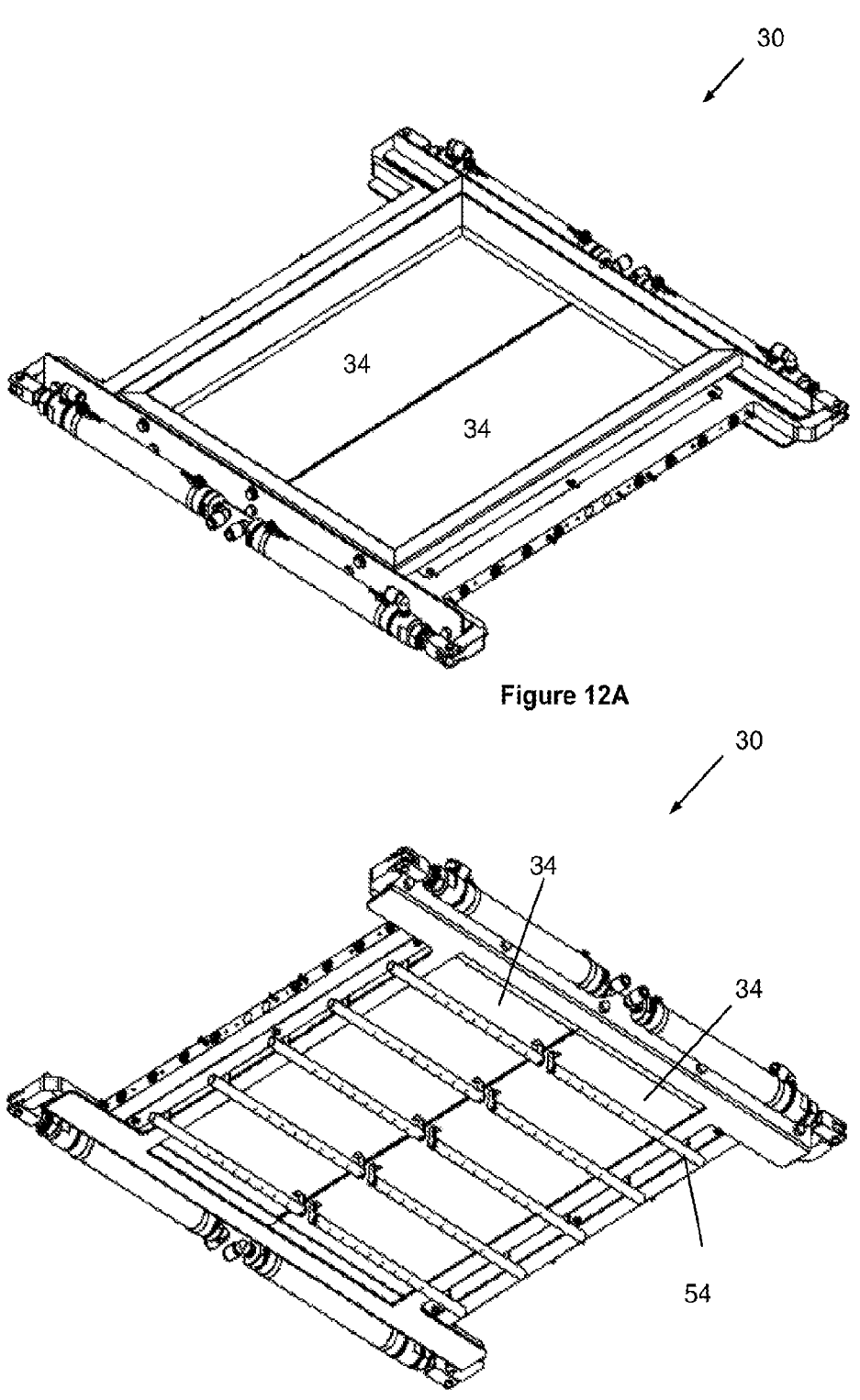

Referring to FIGS. 10 to 12, in pasteurization units having separate heating and cooling chambers, a middle assembly 30 is arranged between the first chamber 20 and the second chamber 22 and like the top assembly 24 includes an opening and one or more panels, gates, or doors that actuate between a closed position in which the first chamber 20 is sealed off from the second chamber 22 and an open position in which the opening is exposed and product from the first chamber 20 can flow into the second chamber 22.

Referring to FIG. 10, the middle assembly 30 on a surface facing the interior volume of the first chamber 20 can include one or more inputs for inert gas and/or a heating element. When the middle assembly 30 on this surface includes both a heating element and inputs for inert gas, a thermal flow can be generated from the middle assembly 30 to thereby provide convection heating within the first chamber 20.

Referring to FIGS. 11-12, the second chamber 22 or the middle assembly 30 can be provided with one or more inputs 54 allowing for a flow of cryogenic fluid into the second chamber 22. When included on the middle assembly 30, they are provided on a surface facing the interior volume of the second chamber 22. The liquid nitrogen can be flowed into the chamber at a single position or through multiple input 54 positions. For example, rails with liquid nitrogen inputs 54 can be provided on the middle assembly 30 such that they are facing into the second chamber 22. Inclusion of multiple rails and inputs can allow for a uniform and rapid flow of liquid nitrogen into the second chamber 22. Additionally or alternatively, spray nozzles can be present in the second chamber 22 and/or on the middle assembly 30 directed to an internal volume of the second chamber 22 for introduction of the liquid nitrogen or other liquefied gas.

Referring to FIG. 27A-27D, the second chamber can include a circulation unit. The circulation unit can allow for circulation of inert gas in the chamber. For example, warmed inert gas can be circulated though the second chamber 22 to warm up the product to room temperature after cryogenic cooling. The cryogenic fluid can be introduced into the second chamber 20, for example, through inlets 54 provided in the second chamber 20 as opposed to or in addition with one or more inlets provided in the middle assembly. As with the circulation units described above, the circulation unit on the second chamber can include a filter arranged at the outlet for filtering the inert gas exiting the chamber. The filtered inert gas can be recycled through the circulation chamber.

Figures 25A, 25B:
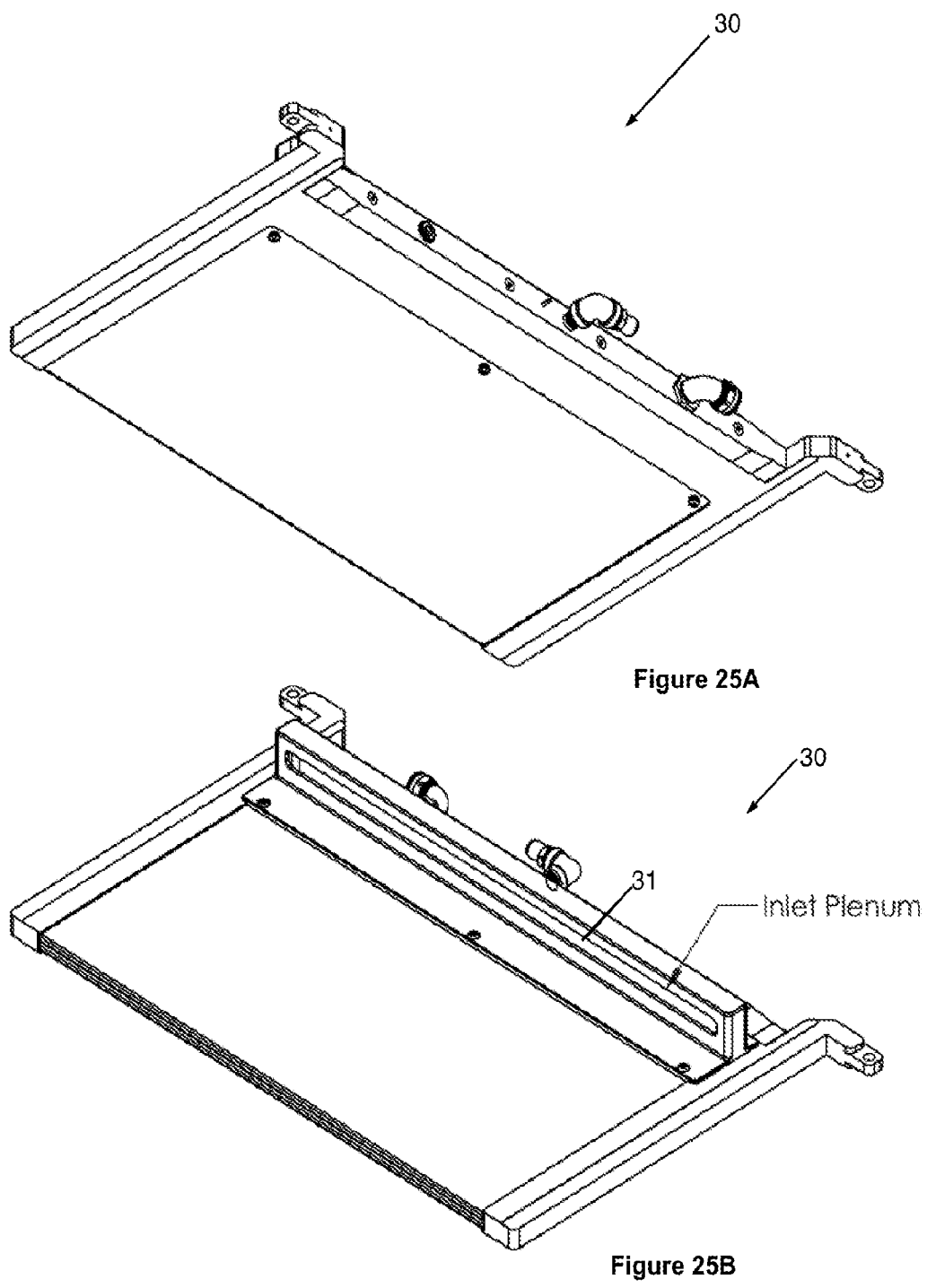

Referring to FIG. 25, a middle assembly 30 can include sliding doors 34 (only one shown in FIG. 25) that separate to expose the opening 38 into the second chamber 22. The middle assembly 30 doors can be actuated such that product flows into the second chamber 22 from the first chamber 20 in a controlled manner. For example, the doors can actuate to allow flow of product in a defined area such that product flows in a substantially single file line into the second chamber 22. The middle assembly 30 doors can include an inlet plenum 31 through which vapor and/or inert gas is flowed into the first chamber 20 from the circulation unit. For example, the inlet plenum 31 of the middle assembly 30 can communicate with the outlet plenum 48 of the circulation unit 46, such that when the doors of the middle assembly are closed, the inlet plenum 31 on the doors seals against the outlet plenum of the circulation unit and vapor and/or inert gas can be flowed from the circulation unit into the inlet plenum and into the first chamber. When the doors are open, the inlet plenum is disposed away from the circulation unit outlet and vapor and/or gas does not flow there-through. A bellows can be provided to seal over the inlet plenum 31 when the doors are in the open position. If a bellows is provided, the inlet plenum 31 could be used to flow vapor and/or inert gas in the region of the first chamber when the doors are opened.

The middle assembly doors 34 can include a first surface and an oppositely disposed second surface. The first surface can face into the first chamber 20, while the second surface faces into the second chamber 22. The inlet plenum 31 for inert gas flow can be arrange on or extend from the first surface. The middle assembly doors can be provided with one or more heaters 64, such that a bottom surface of the first chamber 20 is heated to maintain uniform temperature throughout the chamber for pasteurization.

The middle assembly can also include a drain 35 in fluid communication with the first chamber to allow for draining any liquid within the first chamber.

Any of the features described herein for a two chamber pasteurization unit can be incorporated into a single chamber pasteurization unit. For example, elements arranged on the middle assembly 30 as described above can be incorporated into one or both of the top and bottom assemblies of a single chamber pasteurization unit. Further, such elements could alternatively or additionally be incorporated into the heating/cooling chamber itself.

The second chamber 22 can also include a circulation unit 46, as described above. As detailed below, in use, inert gas can be flowed in the second chamber 22 to maintain a low or no oxygen environment. The circulation unit 46 can be used for such flow. Additionally, the circulation unit 46 can be used for circulation of warmed inert gas, which can be used for equilibrating the product back to a safe handling temperature after rapid cooling. For example, the circulation unit 46 can include a heater to heat the inert gas before it is introduced into the second chamber 22, thereby generated a convection heat within the second chamber 22 to aid in equilibrating the product back to a safe handling temperature after rapid cooling is complete. In embodiments having a single heating/cooling chamber, warmed inert gas can be circulated through the circulation unit 46 during both the heating and post cooling cycles.

Figures 13A, 13B:
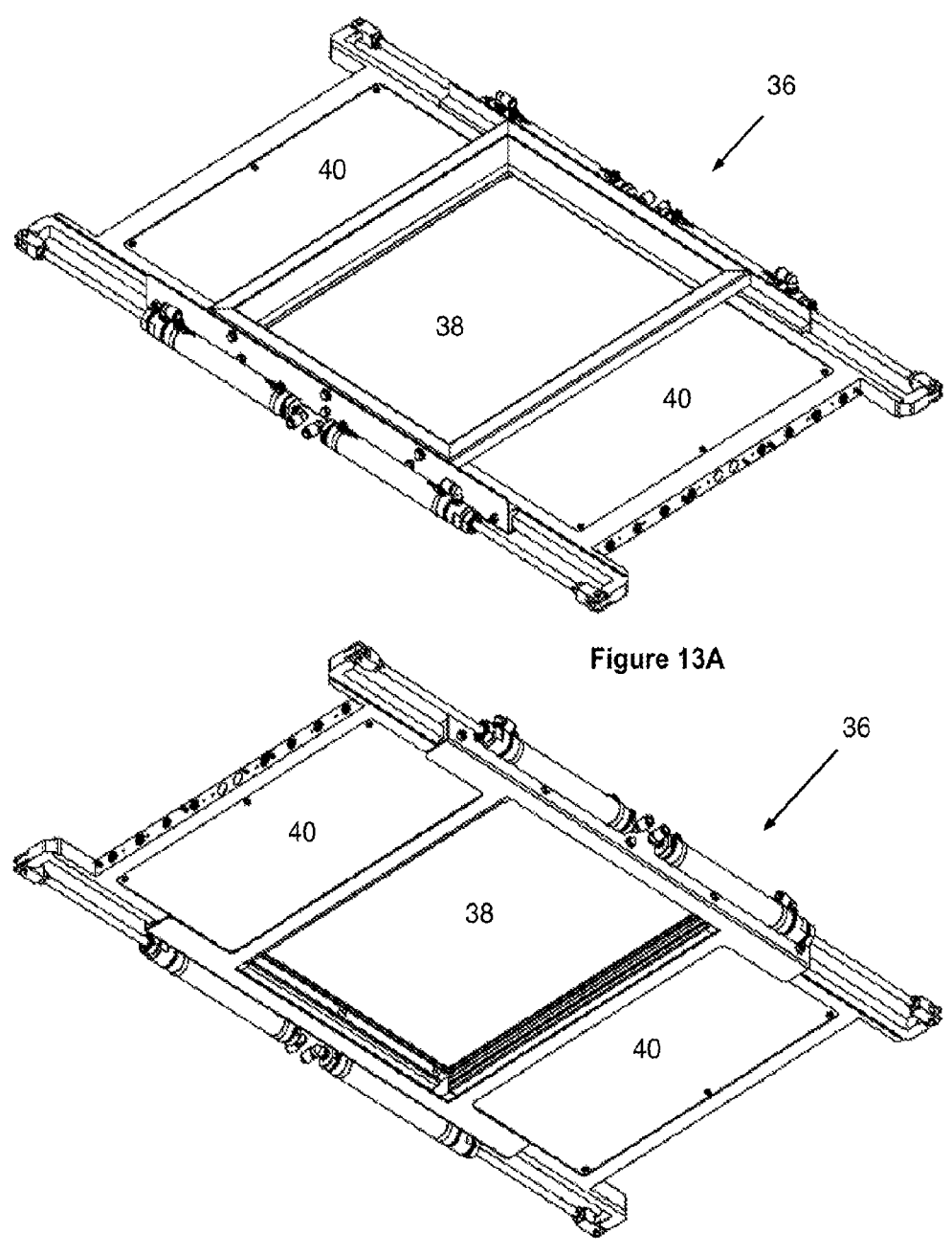
FIGS. 13A-13E are various views of a bottom door assembly in accordance with the disclosure, showing the assembly in the open position.
Figures 13C, 13D, 13E:
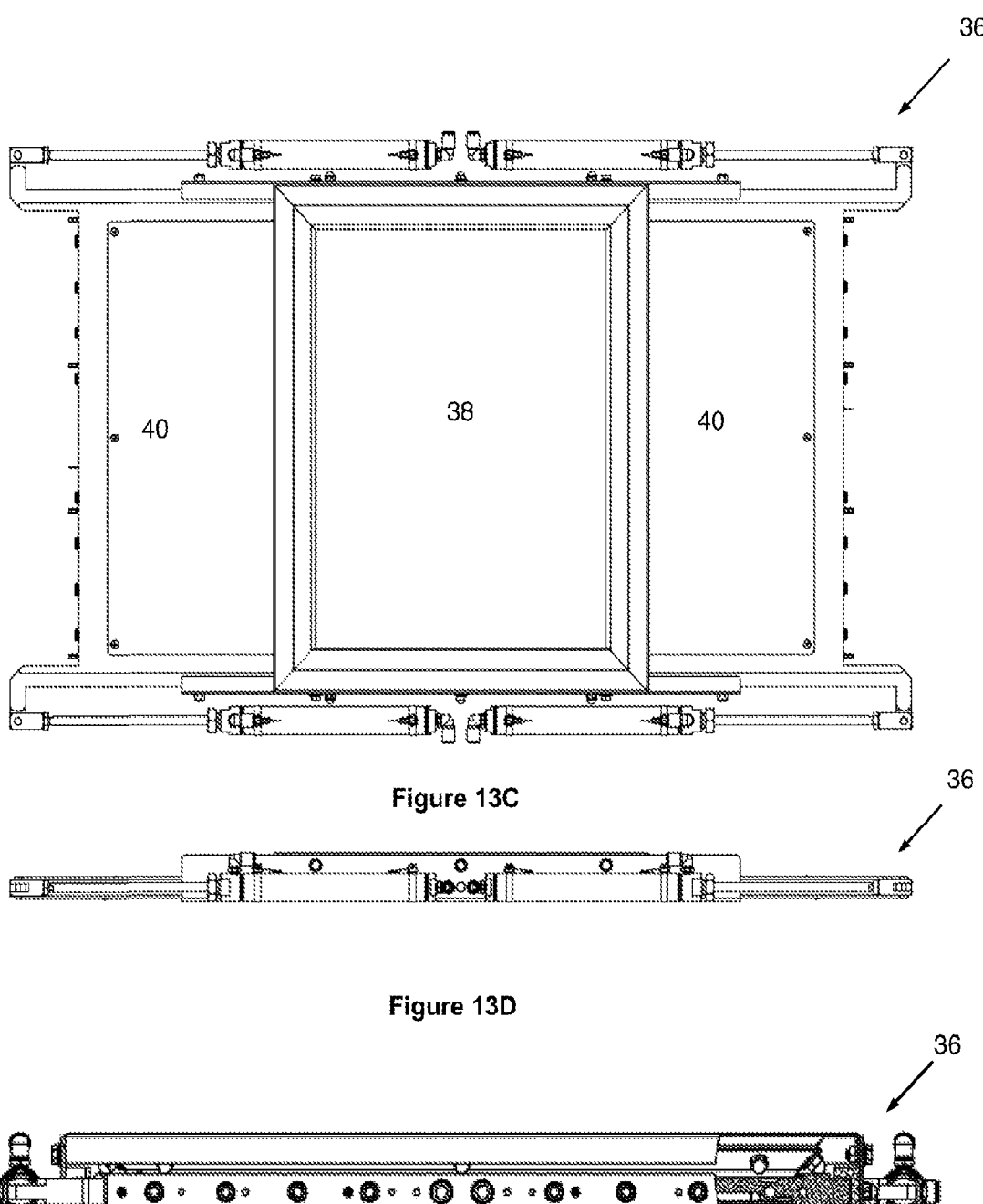
Figure 14A:
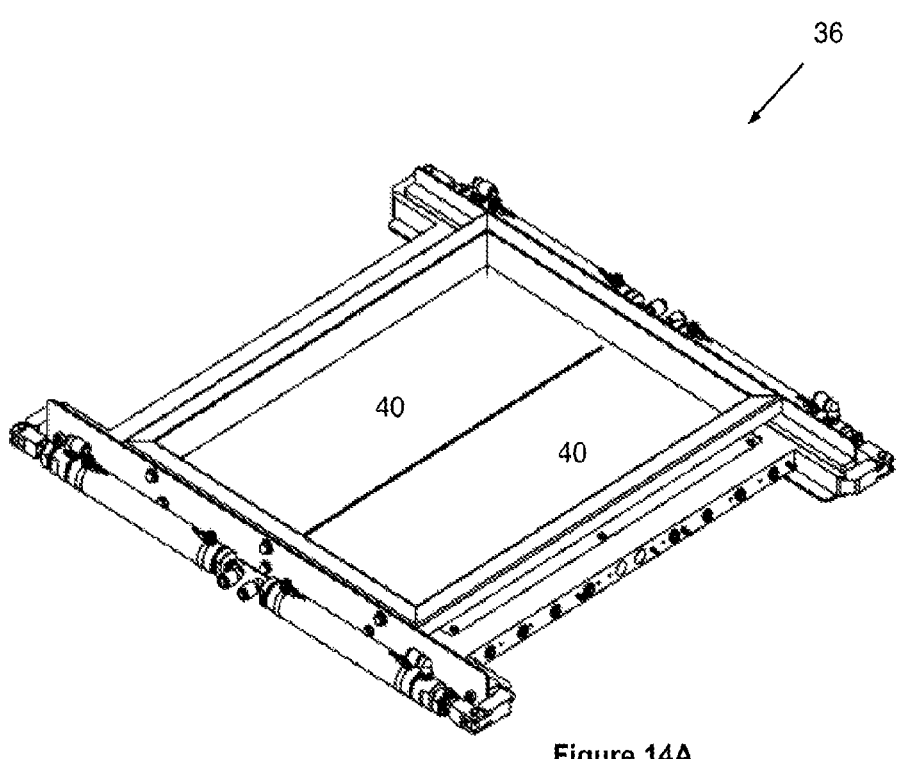
FIGS. 14A-14E are various views of the bottom door assembly of FIG. 13, showing the assembly in the closed position.
Figure 14B:
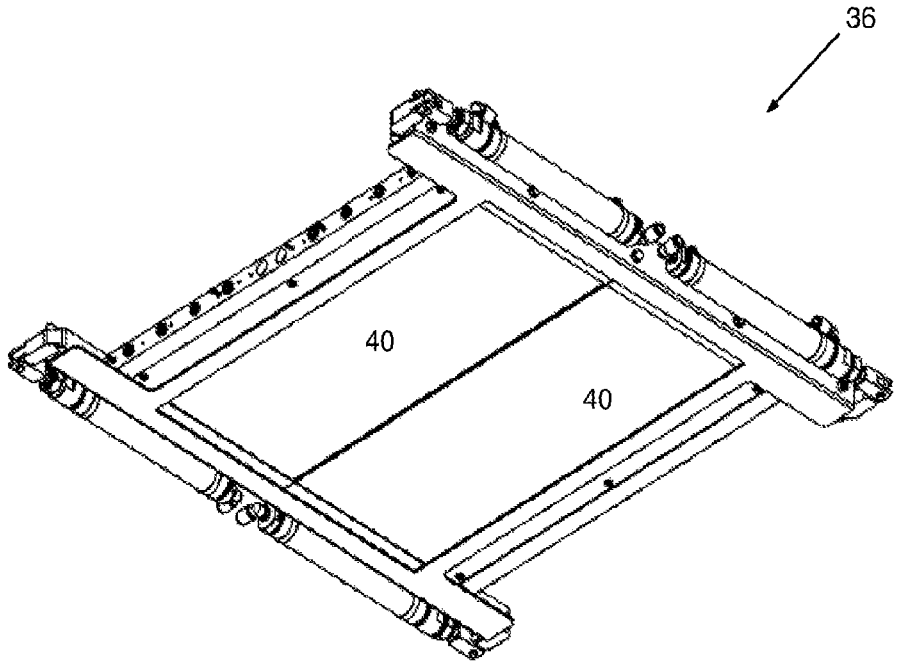
Figure 14C:
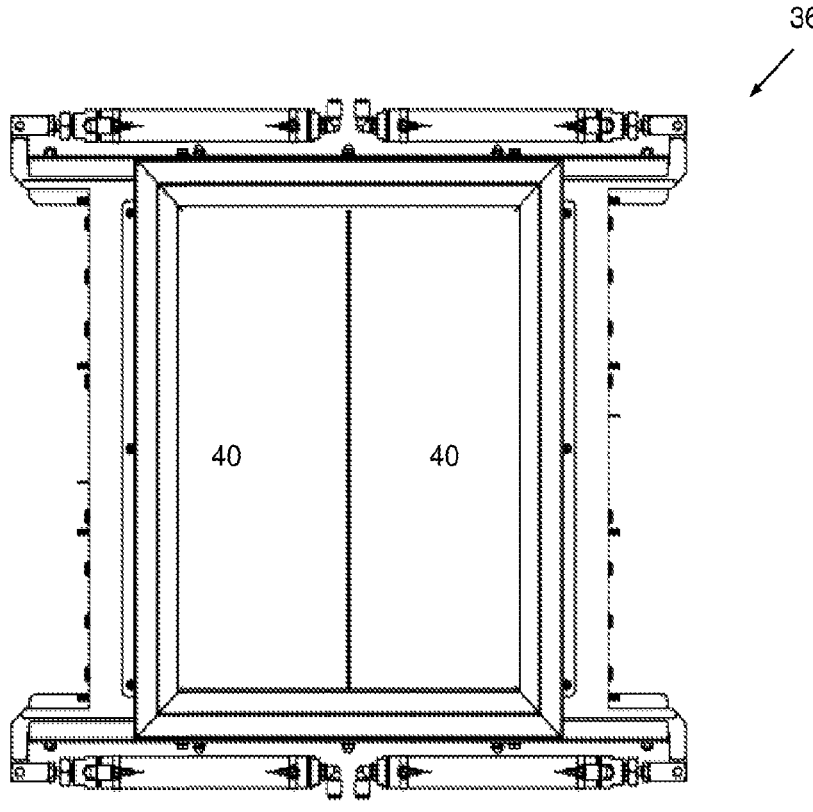
Figure 14D:
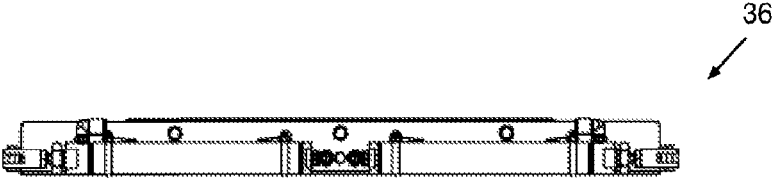
Figure 14E:
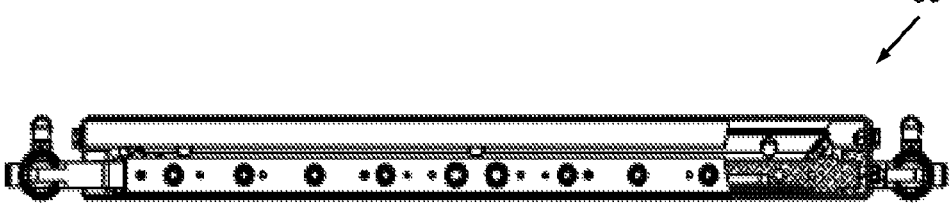

Referring to FIGS. 13 and 14, the unit can further include a bottom assembly 36 arranged downstream of the second chamber 22 or in a single chamber arrangement, arranged downstream of the single heating/cooling chamber. The bottom assembly 36, like the top and middle assemblies, includes an opening 38 and one or more doors or panels 40 that shift between a closed position, in which the second chamber 22 remains sealed at the second chamber 22 product outlet and can retain product within the second chamber 22, and an open position, in which the opening 38 is exposed and product can flow out of the pasteurization unit. This opening at the second chamber 22 will be referred to generally herein as a pasteurized product outlet 27. The bottom assembly 36 can include, for example, a heater 37 and inert gas inputs as an alternative or additional means of generating convection heating within the second chamber 22 for equilibrating the product to the safe handling temperature. The bottom assembly 36 can alternatively include only inert gas inputs to maintain a low or no oxygen environment within the second chamber 22. In embodiments of the pasteurization unit having a single chamber, the bottom assembly 36 can include inlets for cryogenic fluid for the cooling cycle.

Figures 17A, 17B, 17C, 17D:
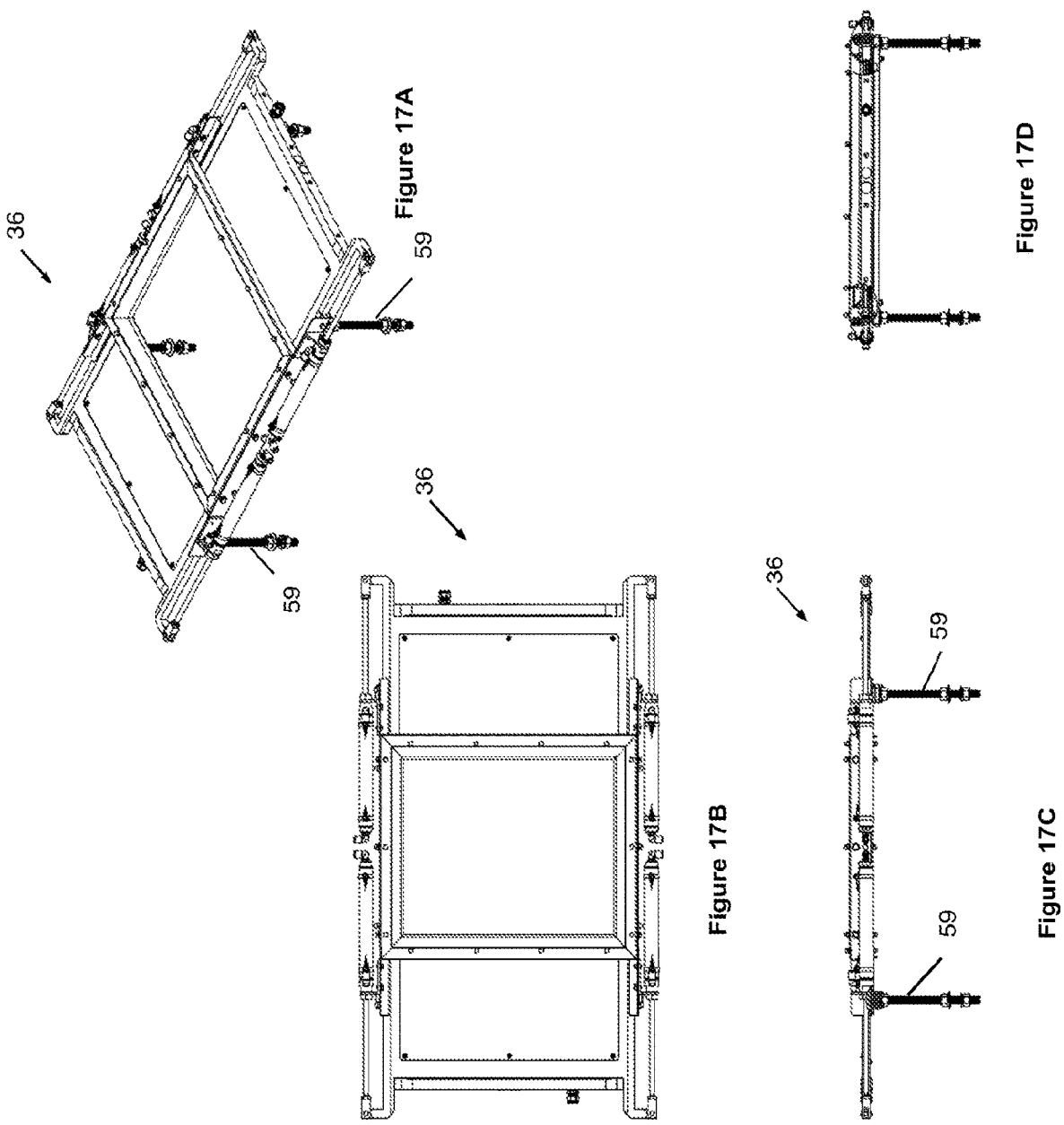
FIG. 17A-17F are various views of a bottom door assembly in accordance with the disclosure.
Figure 17E:
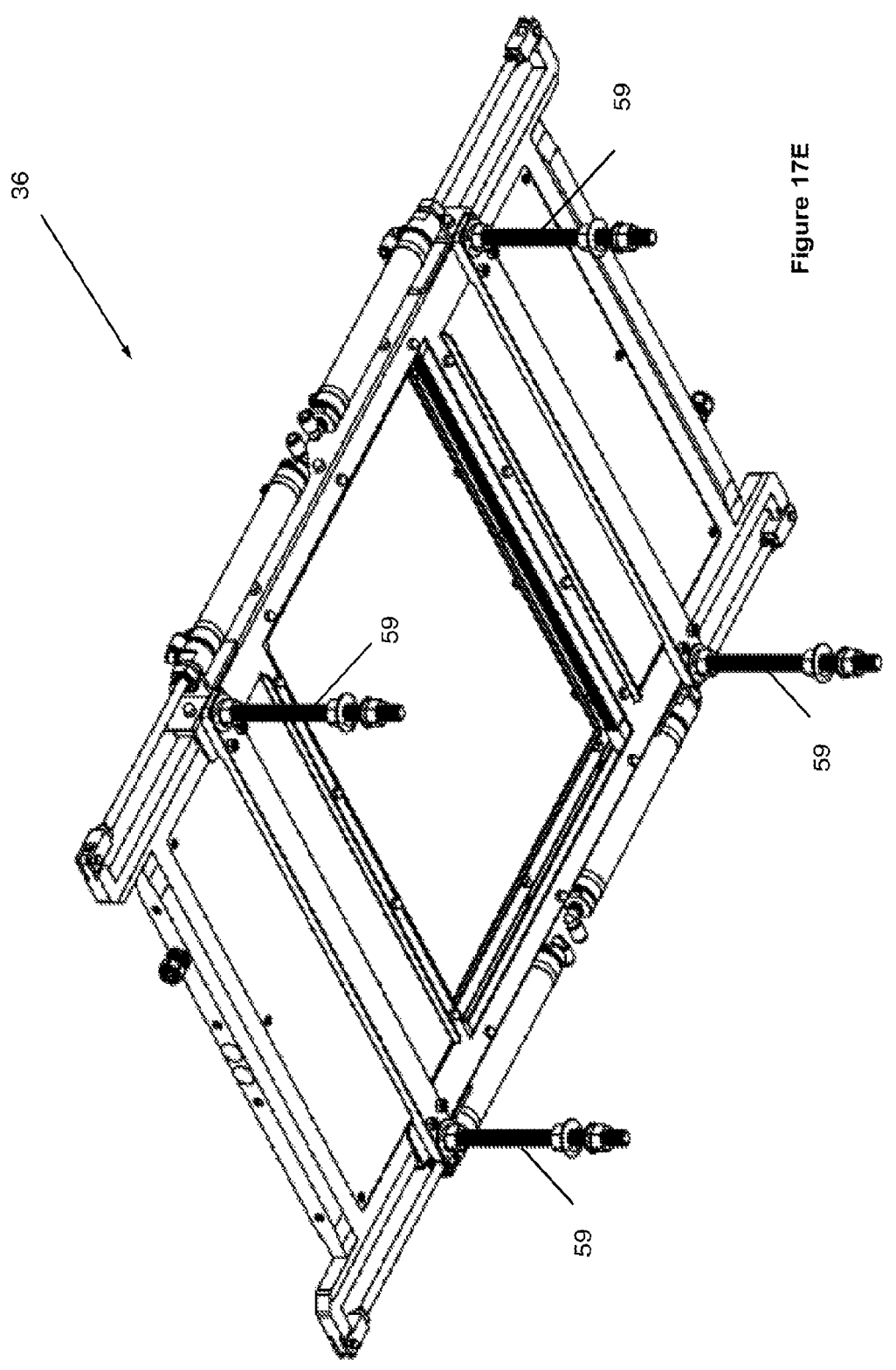
Figure 17F:
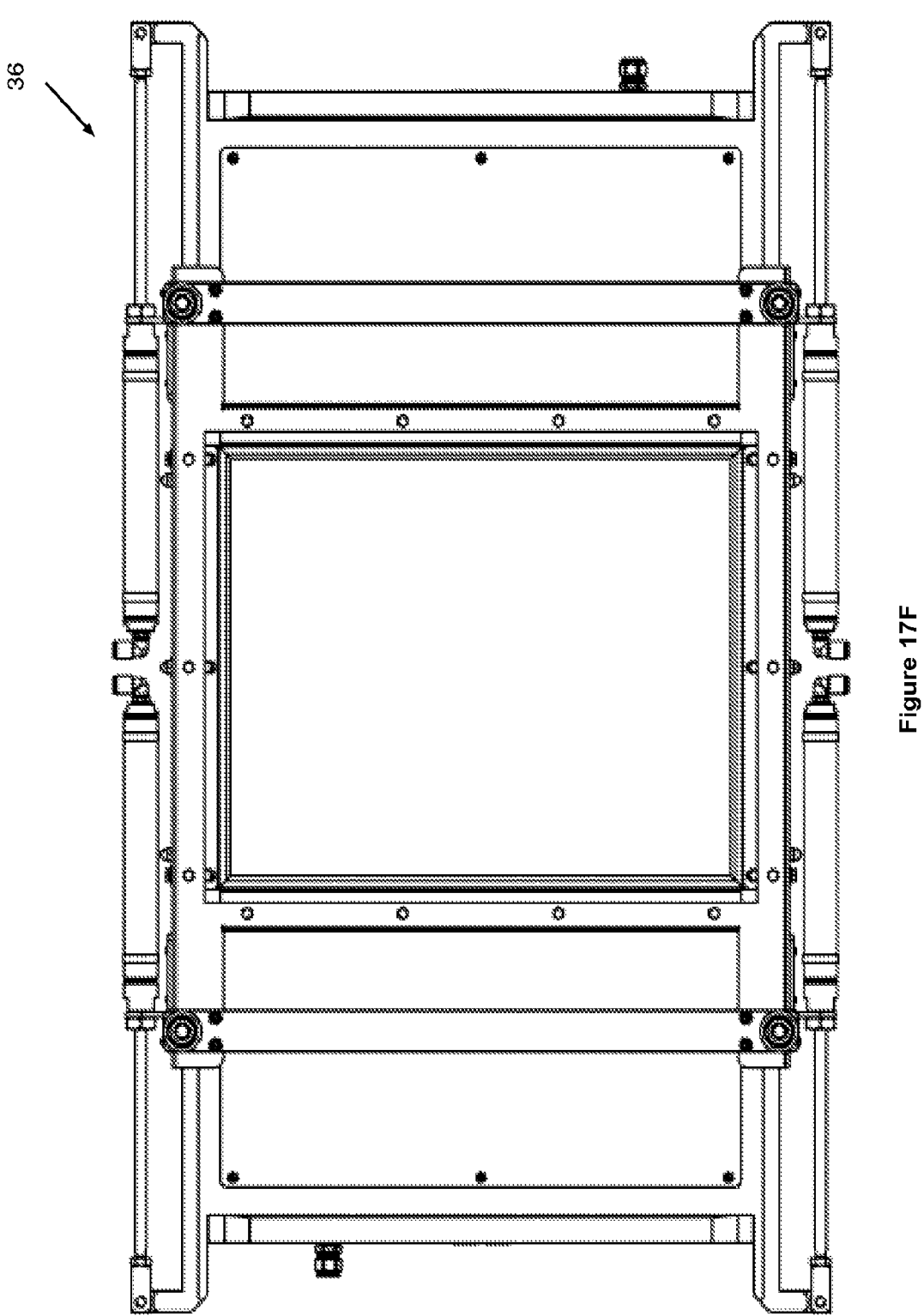

Referring to FIG. 17, the bottom door assembly can include legs 59 extending downwardly from the system. Such legs can be adapted to allow for use of the pasteurization system on a table top or cart, such as shown in FIG. 15, and provide a space beneath the bottom door assembly for a cartridge 12 or other receptacle for retrieving the pasteurized product from the chamber after the pasteurization process is complete. That is, a suitable receptacle can be provided beneath the bottom door assembly in the space created by the incorporation of the legs and the pasteurized product can pass through the bottom door assembly when opened and into the receptacle.

Other arrangements or connecting systems can be used in the pasteurization unit. For example, the pasteurization unit can be configured to be in-line with a packaging unit as shown in FIG. 1. The bottom door assembly can in embodiments include connectors for connecting or otherwise attaching the pasteurization unit onto a downstream system, such as a packaging unit so that the two units can be provided separately. This can facilitate mobile use of the units, allowing them to be moved separately and then combined on site for use.

In any of the units herein, equilibration of the product after rapid cooling could be done in a separate chamber or other structure, such as a hopper. In such case, the rapidly cooled product could be transferred to the further chamber or structure after the cooling time.

In any of the units herein, any one or more of the assemblies can be integral with the chamber to which it is associated. For example, the top and middle assemblies can be integral with the first chamber 20, and the bottom assembly 36 can be integral with the second chamber 22. In alternative arrangement, the top assembly 24 can be integral with the first chamber 20, and the middle and bottom assemblies can be integral with the second chamber 22. In still further alternatives and one of more of the assemblies can be separable from the respective chamber against which it is disposed. In single chamber units of the disclosure, the top and/or bottom assemblies can be integral with the chamber.

Once cooled and returned to a safe handling temperature, the product can be flowed out of the pasteurization unit into a sterile container, field package or other packaging, or downstream processing unit such as a packaging unit. The pasteurization unit and/or downstream processing unit can include one or more sampling devices or sampling access ports for obtaining samples of the cannabis at various stages of the process, such as post pasteurization, during downstream processing, and/or during packaging.

The pasteurization unit can include or be arranged in fluid communication with a hopper into which the pasteurized product is flowed. For example, the product outlet 18 can be in fluid communication with a packaging machine (not shown). For example, the product outlet can be in fluid communication with a feeder for feeding product to packaging equipment or other element of the packaging equipment such as a hopper, funnel, scale or the like. For example, a feeder can be arranged at the product outlet, which can be coupled to or otherwise facility flowing the product to another apparatus such as a packaging machine and/or scale. For example, the feeder can allow the product to be flowed into a bulk packaging apparatus. For example, the feeder can allow the product to be flowed to a hopper for weighing and separating into smaller packaging configurations. In embodiments in which the product outlet 18 flows product into an element of the packaging equipment, the pasteurization unit 10 can include a gassing unit that flows filter inert gas over the product as it enters into the packaging equipment to maintain pasteurization of the product and maintain low oxygen levels within the product to prevent recontamination. For example, the inert gas can be filtered nitrogen. For example, the inert gas can be HEPA filtered nitrogen.

For example, pasteurized product outlet 18 can be configured to release the product directly for field packaging. For example, the pasteurized product outlet 18 can be positioned to release the product to a slide or funnel that would direct the product into a package. For example, the field package can be a flexible package. Any package configuration, such as blow molded containers, jars, cans, and the like, can be used. In the cannabis industry, for example, the pasteurized cannabis product can be field packed and stored for later packaging in smaller retail packaging amounts. In embodiments, the gassing unit can be provided at the pasteurized product outlet to flow an inert gas over the pasteurized product outlet as the product is flowed into a package. The gassing unit can include a gassing element to flow the inert gas across the product outlet such that the product passes through the flow as it is released from the pasteurizing unit 10 into the package. The gassing unit can further include a gassing element directed to flow inert gas into the package to remove contaminants from the interior of the package and/or provide a modified atmosphere within the package as the product is released from the pasteurization unit into the package. The gassing unit provided to direct gas into the packaging can advantageously provide a modified atmosphere packaged product that resists growth of mold, yeast and/or bacteria while the product remains in the package. A gassing unit can be provided, for example, on the bottom assembly 36 on a surface facing opposite the internal volume of the second chamber 22.

In embodiments, a sealing apparatus can be positioned in close proximity to the pasteurization unit in such embodiments to allow for sealing of the package. The sealing apparatus can include gassing elements to provide a modified atmosphere within the package that maintained within the package during sealing. Any known sealing and/or modified atmosphere machines can be used. The sealing apparatus can be entirely separate from the pasteurization unit. The pasteurization unit, the packaging apparatus, such as the slide or funnel for field packaging, and the sealing apparatus can form a system for field packaging in embodiments.

Figure 19:
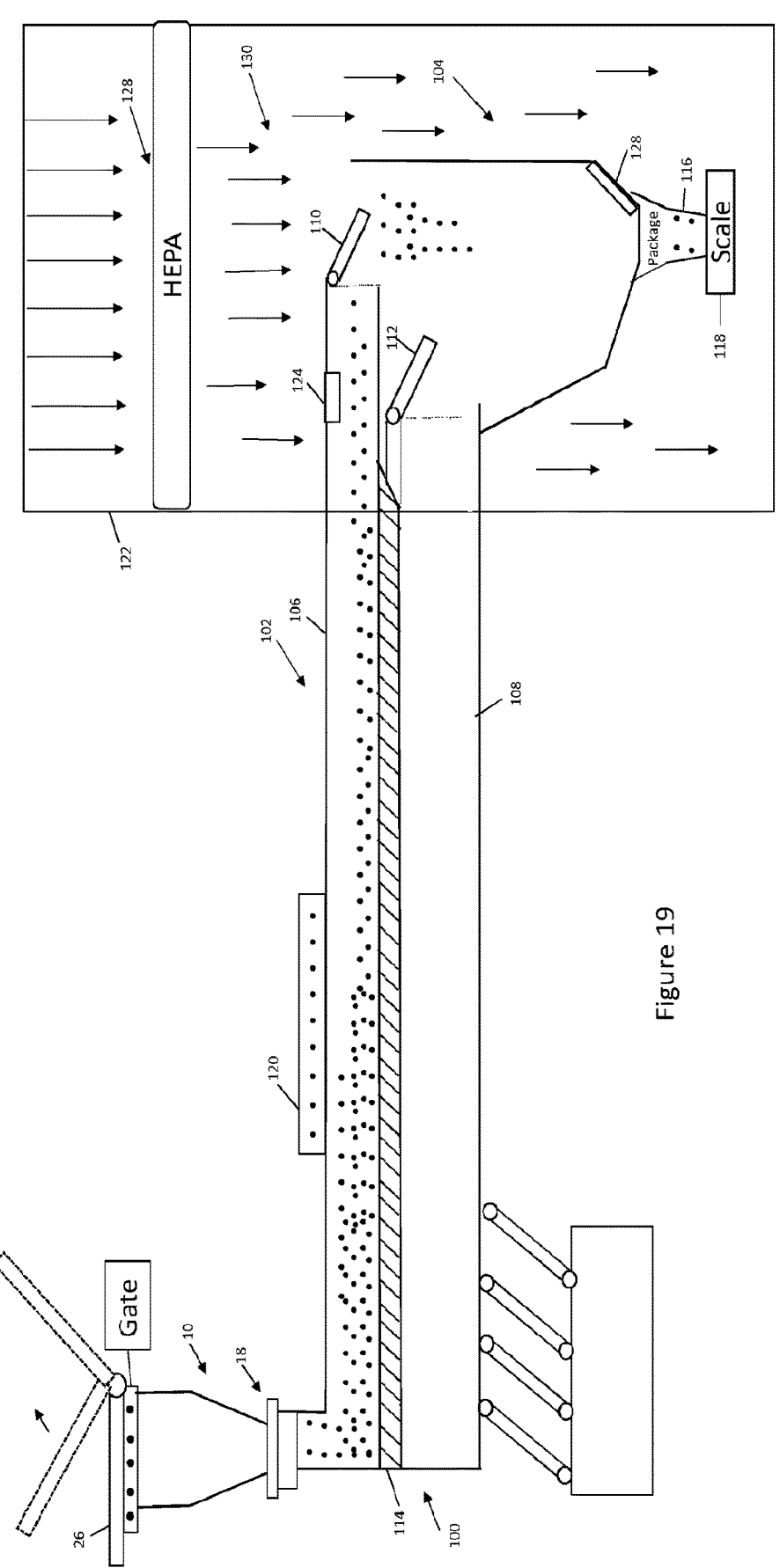
FIG. 19 is a schematic illustration of a vibratory feeding and bagging system.

Referring to FIG. 19, the product outlet 18 can be configured to release the product into a hopper, which is connected to a vibratory feeding and bagging system 100. In embodiments, the vibratory feeding and bagging system can be directly coupled or otherwise in fluid communication with the product outlet and the hopper can be eliminated. In embodiments, the product outlet 18 can include a gate for controllably releasing product from the pasteurization unit 10 into the vibratory feeding and bagging system 100. The vibratory feeding unit 102 can be sealed by a moveable sealing apparatus or door 110, 112 that can allow the product to pass from the vibratory feeding unit 102 into the bagging unit 104 when desired, but otherwise seal off the vibratory feeding unit 102. For example, the vibratory feeder unit 102 can have a bulk dribble system 110, 112 that can allow for flow of the product 14 to the bagging system 104 at multiple rates to aid in the efficient and accurate filling of the package to the desired weight. Bulk dribble systems can allow a first rate of product to flow out of the feeder by opening the sealing door 110, 112 to a fully open position until the package weight is close to being met, and then reducing the flow rate of the product by closing the sealing door a portion of the way closed to provide more precise control over the filling process. It should be understood that the vibratory feeding and bagging system described herein can be used in line with the pasteurization unit as shown in FIG. 1 or can be used as a standalone apparatus or in connection with other downstream packaging systems.

In any of the vibratory feeding and bagging systems 100 herein the moveable sealing apparatus 110, 112 can completely seal off the vibratory feeding unit 102 from the bagging unit 194. This can be useful, for example, in isolating the vibratory feeding unit 102, which can be sealed off from the pasteurization unit 10 by the product outlet door, so that the interior of the vibratory feeding unit 102 can be cleaned and/or sterilized when needed by passing filtered inert gas and/or sterilizing gas through the interior of the vibratory feeding unit 102. The interior of the vibratory feeding unit 102 can include one or more vents 124 providing an outlet through which the inert and/or sterilizing gas can be controllably removed and contained from the unit 102. The one or more vents 124 can be in fluid communication with a filter (not shown), such as a HEPA filter, to filter the gas as it exits the interior volume of the vibratory feeder either to recycle the gas into the system for subsequent use or safely remove the gas from the system. The vibratory feeding unit 102 can also include one or more gassing units 120 to maintain a flow of inert gas over the product 14 during the bagging operation. Other types of filters are also contemplated herein, such as activated carbon filters.

All or a portion of the vibratory feeder and bagging system can be contained in an enclosure 122 and a flow of filtered inert gas 130 can be circulated through the enclosure 122. For example, a portion of the vibratory feeding unit 102 having the moveable sealing apparatus 110, 112 and the bagging system 104 can be contained in the enclosure 122 and have flow of filtered inert gas blown over these systems during operation. The filtered inert gas can be, for example, HEPA filtered inert gas. The enclosure 122 can have a vent 126 at the downstream end of the flow of inert gas to vent the enclosure. The vent can be in communication with a filter, such as a HEPA filter to allow for the vented gas to be filtered and recirculated into the system. The gassing unit 128 of the enclosure 122 can also be adapted to flow sterilizing gas into the enclosure to allow for cleaning and/or pasteurization of the enclosure when needed.

The vibratory feeding and bagging system 100 can include, for example, a single vibratory feeder that directs the released sterilized product to a bagging unit 104 that is adapted to receive a desired weight of product and then release it into a package, such as a plastic bag.

As illustrated in FIG. 19, the vibratory feeder and bagging system 100 can alternatively include a vibratory feeding unit 102 that has two or more vibratory feeders 106, 108 that direct the released pasteurized product to the bagging unit 104. The vibratory feeder and bagging system 100 can include, for example, two vibratory feeders 106, 108 stacked one on top of the other. The pasteurized product can be released from the product outlet 18 to the first vibratory feeder 106. The first vibratory feeder 106 can include a bottom surface that is defined by a screen 114 adapted to allow product of a certain size to pass through the screen 114 and into the second vibratory feeder 108. Each vibratory feeder can be sealed by a movable sealing apparatus 110, 112, such as bulk dribble system that is in fluid communication with the bagging unit 104 to allow product from each vibratory feeding unit 102 to be delivered to the package, if desired, or to control release of the product from the vibratory feeders 106, 108 such that product of only a single size is packaged. Any suitable number of vibratory feeders can be included with screens provided as the bottom surfaces of the top and any intermediate feeders to allow for any number of size separations. This can advantageously provide control over the sizing of the final packaged product allowing more precise mixtures of sizes and/or exclusions of certain sizes.

For example, in the cannabis industry, a dual vibratory feeder system such as shown in FIG. 19 can advantageously allow for size separation of larger size buds from smaller buds and pieces, referred to in the industry as "popcorn and shake." The dual system can be used, for example to package a mixture of larger size buds and popcorn and shake, with specific control over the ratio of the differently sized buds. The dual system can be used to package larger size buds only. The dual system can be used to obtain precise package weights by allowing the popcorn or shake to top off to achieve finer tuning of the package weights with the smaller and lighter product.

In any of the vibratory feeding and bagging systems 100 herein, the bagging unit 104 can include a scale 126 upon which a package rests to measure the package weight as the package is being filled. Other scale systems can be used, for example, allowing a measured weight of product to be delivered to a scale system from the vibratory feeders before being passed to the package.

The bagging system can further include one or more gassing elements 128 to direct a flow of inert gas around the packaging and/or into the package if modified atmosphere packaging is desired.

The pasteurization unit 10 can be a single unit, integral with the vibratory feeding and bagging system 100 or other downstream packaging system. The pasteurization unit 10 alternatively can be separable from, but attachable to the vibratory feeding and bagging system 100 or other downstream packaging system. This can be make the overall system more mobile and to allow for set-up of the system in various sites, such as at cannabis grower facilities.

Any of the systems herein can be particularly advantageous in the cannabis industry for field packaging cannabis and/or hemp. Field packaging and even retail packaging can generally occur in this industry in an environment that can have high contents of airborne contaminants. Packages can be susceptible to growth of yeast, mold, and/or bacteria within the package as a result of this environment. The pasteurization unit and methods of the disclosure can advantageously provide a pasteurized product and a packaging environment that significantly reduces the content of airborne contaminants around the product outlet and within the package during loading of the cannabis and/or hemp from the pasteurization product into the package. Further, introduction of the inert gas, such as nitrogen into the package for modified atmosphere packaging can be further useful in resisting any growth of yeast, mold, and/or bacteria that may remain within the product after pasteurization while the product resides within the package. In any of the foregoing embodiments, the inert gas can be filtered. In embodiments, the inert gas can be HEPA filtered argon, HEPA filtered carbon dioxide, and/or HEPA filtered nitrogen. For example, the packages filled using the system of the disclosure can resist yeast, bacteria and/or mold growth for at least sufficient time for determination of a level of contamination if any remains in the product after the pasteurization cycle. For example, the filled packages can substantially or entirely resist any change in contamination level for 5 days or more, 7 days or more, 10 days or more from the time of packaging.

A system of the disclosure can include a pasteurization unit and a packaging unit, such as the vibratory feeding and bagging system. The system can be provided with an enclosure surrounding all or a portion of the system. For example, the enclosure can be provided at the product outlet of the pasteurization unit and enclose the product outlet and the feeding and/or bagging system. The enclosure can be provided with suitable inlets and outlets to maintain a flow of filtered inert gas through the enclosure. The filtered inert gas can be HEPA filtered inert gas. For example, the filtered inert gas can be HEPA filtered nitrogen.

Method of Pasteurization

FIG. 18 illustrates a process flow chart of an example method of the disclosure. A method of pasteurizing a product, such as cannabis and/or hemp, can include loading the product into a cartridge 12. The cartridge 12 can then be installed on the pasteurization unit (if detachable). Optionally, the product contained in the cartridge 12 can be preheated to a preheat temperature. The preheat temperature can be about 20° C. to about 32° C. The preheating of the product in the cartridge 12 can improve the pasteurization results as the product is brought to a uniform and known starting temperature.

The process further includes preheating the first chamber 20 or the heating/cooling chamber in a single chamber system. For ease of discussion, reference will be made herein to a first and second chamber 22, but it should be understood that such process steps can be accomplished in a single chamber. The first chamber 20 can be preheated while the cartridge 12 is being loaded and even prior to installation on the pasteurization unit (if detachable) and/or after the cartridge 12 is loaded on to the unit (if detachable) and/or while the cartridge 12 is being preheated. The first chamber 20 is preheated to a preheated temperature. For example, the chamber can be preheated to a temperature of about 65° C. to about 85° C. Preheating can include heating through one or more of convection, microwave and conduction heat sources. For example, the first chamber 20 can be preheated through convection and conduction heating. Preheating can be accomplished using a combination of vapor flow and conduction, convection, and/or microwave heating. When vapor flow is used in the preheating cycle, the chamber can be flushed with an inert gas after the preheating is complete to flush out the vapor. Inert gas can also be flowed in the first chamber 20 during preheating to reduce and/or eliminate oxygen in the first chamber 20. Preheating can allow for a more gentle process on the product because the product is not exposed to a heating ramp and the amount of time the product is exposed to heat can be reduced. It can also ensure more uniform heating of the product by providing a chamber and associated chamber walls that are at the pasteurization temperature thereby avoiding cold spots during the process.

In processes of the disclosure in which vapor is not used in the preheating cycle, the vapor injection unit can be initiated to begin vapor generation. Vapor and/or superheated steam can be used. Superheated steam generally has a temperature of greater than 100° C. The vapor of the pasteurization unit can have a temperature of about 100° to about 400° C. Initiation of the superheating of the steam can take place during a given time interval of the preheating of the first chamber 20. The duration needed for initiation of the steam can depend on the steam or vapor injector unit utilized and temperature set point thereof. This initiation time can be predetermined and the ramping of the temperature of the first chamber 20 during preheating can be predetermined, such that the initiation can be automatically triggered by a control unit once the preheating of the first chamber 20 reaches a given temperature such that the pasteurization temperature would be reached in the same or substantially the same amount of time as initiation time. This can be advantageous to avoid a delay between the first chamber 20 reaching the pasteurization temperature and the vapor injector being ready for injection of the vapor. Alternative set points and preheating times can also be used. For example, the vapor injector can be initiated after the first chamber 20 is preheated to the pasteurization temperature.

Once the first chamber 20 reaches the preheating temperature, the top assembly 24 can actuate to expose the opening and allow the product to flow from the cartridge 12 into the first chamber 20. If the cartridge 12 also includes a door or other actuatable panel and its own opening, the cartridge 12 opening can also be exposed at this time or prior to opening of the top assembly 24, for example during some time of the preheating stage.

The top assembly 24 will close the opening when the product is contained in the first chamber 20 to seal the first chamber 20. Vapor can then be injected into the first chamber 20, while the heating source(s) maintain the first chamber 20 at the preheating temperature. The preheated temperature can be the pasteurization temperature or can be higher than the pasteurization temperature. In embodiments in which the preheating temperature is higher than the pasteurization temperature and initial rapid heating cycle can be performed at the preheating temperature. For example, product can be introduced into the chamber and vapor flow can be initiated to maintain the chamber at the preheated temperature. The utilization of the vapor flow in this rapid heating cycle can allow for rapid heat transfer into the product quickly bringing the core of the product up to a temperature at which pasteurization can occur. The rapid heating cycle can be performed by holding the product at the preheated temperature for about 10 second to about 2 min, about 30 sec to about 90 second, about 60 second to about 90 second, about 80 second to about 100 second and any values or ranges there-between. It has been advantageously found that for sensitive product such as cannabis and hemp, the utilization of the rapid heating cycle with the vapor flow results in not only rapid heating of the buds, but also formation of a moisture layer on the buds which has been observed to be protective during the pasteurization process.

After the rapid heating cycle, the temperature of the chamber can be reduced, if desired, to the pasteurization temperature. The chamber temperature before introduction of the product can be up to 95° C. The pasteurization temperature can be about 65° C. to about 75° C. For example, the pasteurization temperature can be about 65, 66, 67, 68, 69, 70, 71, 72, 73, 74, or 75° C. The pasteurization temperature can depend on the sensitivity of the product to heat and should be selected to be below a temperature at which degradation in the product is observed. The temperature of the chamber can be reduced by reducing the convection, conduction and/or microwave heating; reducing the vapor flow; and/or increasing a flow of inert gas. The inert gas can be warmed but is at a temperature lower than the chamber temperature to allow for a cooling effect. Once the pasteurization temperature is reached, the pasteurization cycle can include holding the product at the pasteurization time for about 1 min to about 10 min, about 2 min to about 7 min, about 5 min to about 8 min, about 4 min to about 8 min. Where sterilization is desired as opposed to pasteurization longer heating times can be used. For example, a product can be sterilized in about 12 min.

In embodiments in which a rapid heating cycle is not performed and the preheated temperature is the pasteurization temperature, the product can be held at the pasteurization temperature to perform the pasteurization cycle as the initial process step. In such embodiments, the pasteurization time can be increased if necessary, for any suitable time needed to observe the desired reduction in pathogens (such as bacteria, yeast, mold, and spores thereof).

Vapor can be injected during an entire pasteurization cycle or a portion of the pasteurization cycle. For example, vapor can be injected at the start of the pasteurization cycle, but for a period of time less than the pasteurization time. Alternatively, the pasteurization cycle can be initiated with the convection and conduction heating and vapor can be injected as some point after the cycle begins. The vapor can be injected through the remainder of the pasteurization time or for only a portion of time such that the pasteurization cycle is completed without vapor being injected. The pasteurization temperature is maintained during the entire pasteurization cycle. The rate of vapor flow can also be adjusted throughout the process. For example, during preheating and/or rapid heating a valve controlling the rate of a vapor flow can be open about 100%. The valve can be partially closed, for example, to 75% flow or 50% flow, during the pasteurization cycle. This can reduce the amount of moisture present in the chamber to avoid undesirable moisture gain in the product as well as help to reduce the heat to the pasteurization temperature. During pasteurization the steam can be further adjusted to reduced flow if needed to maintain the pasteurization temperature and/or control the humidity within the chamber. Inert gas can be similarly adjusted to different flow levels throughout the process to aid controlling in temperature and/or humidity levels.

The product resides in the first chamber 20 for a pasteurization cycle. The amount of time require for the pasteurization cycle can vary depending on the product and the temperature set points and the use of the rapid heating cycle before pasteurization. Generally, the pasteurization cycle time can be about 30 sec to about 10 min. For cannabis and hemp, the pasteurization cycle can be about for a time sufficient to reach a core temperature of the buds of about 65° C. to 75° C. The internal temperature of the buds can be dependent upon the level of contaminant reduction required.

During the pasteurization cycle and optionally continuing from the preheating cycle, filtered inert gas can be flowed through the chamber. As detailed above, a circulation unit 46 can be provided to flow the inert gas across the chamber from an inlet and into an outlet with the inlet and outlet being in fluid communication outside of the chamber and a filter disposed there between to allow the gas collected at the outlet to be filtered and recirculated back into the first chamber 20. This recirculation can be utilized with or without continued injection of fresh inert gas. In alternative embodiments, a flow of fresh inert gas can be maintained and the circulation unit 46 can simply vent the outflow of inert gas from the first chamber 20 without recycling the inert gas.

The inert gas can be filtered, for example HEPA filtered. The inert gas can be nitrogen, argon, carbon dioxides, and mixtures thereof. Use of air or noble gasses also contemplated herein. In pasteurization cycles in which low or no oxygen levels are not needed, air may be used as the inert gas. For example, the inert gas can be filtered and/or HEPA filtered nitrogen. The flow of inert gas such as nitrogen can reduce or eliminate oxygen present in the first chamber 20, which can aid in more effective pasteurization and prevent or reduce growth or activation of spores that may be present on the product during pasteurization.

After the pasteurization cycle is complete, the middle assembly 30 actuates to expose the middle assembly 30 opening and the product is allowed to flow into the second chamber 22. The second chamber 22 can optionally be precooled and precooling can be done during the pasteurization cycle. Cryogenic fluid can be injected into the second chamber 22 while the product is being introduced into the chamber and/or once the product is fully within the second chamber and the second chamber 22 is closed. As detailed above, the middle assembly 30 can include an injection rail or series of rails that allows for injection of the liquid nitrogen into the second chamber 22 over the product. Other configurations, as described above including cooling structures or nozzles in the bottom assembly 36 and/or the second chamber 22 itself are also contemplated and described herein. The product can be cooled to sub-zero temperatures in various embodiments. The rapid cooling removes residual heat from the product, limiting the exposure time of the product to heat, which can be particularly advantageous for sensitive products such as cannabis and hemp. The cryogenic fluid can be injected for a time of about 0.25 seconds to about 20 seconds. After rapid cooling, the product can be brittle or otherwise susceptible to damage if handled immediately. In such cases, the product can reside in the second chamber 22 until it reaches a temperature for safe handling. The temperature for safe handling can vary by product. For example, the product can be allowed to reside in the second chamber 22 after super-cooling until it reaches a temperature of about 0° C. to about 25° C., about 10° C. to about 40° C., or about 20° C. to about 30° C. For cannabis and hemp, this temperature can refer to a core bud temperature. During equilibration of the product to a safe handling temperature, warmed inert gas can be flowed through the second chamber 22. The warmed inert gas can have a temperature of about 15° C. to about 32° C. for gentle warming without heating of the product.

In pasteurization units utilizing a single chamber, the rapid cooling can be performed within the same chamber as the heating. The pasteurization cycle can include an inert gas flush in the final seconds of the cycle to flush out the chamber and any residual vapor. An inert gas flush can alternatively be performed immediately after the pasteurization cycle instead of during an end portion thereof. Liquid nitrogen can be injected into the heating/cooling chamber through the chamber itself and/or one or both of the top and bottom assemblies for rapid cooling the product. Warmed inert gas can be flowed through the chamber thereafter to bring the temperature to room temperature without heating of the product. This flow of warmed inert gas can not only temper the product back to room temperature, but can also be useful in evaporating any free water vapor remaining on the product.

As with the first chamber 20, a flow of inert gas can be maintained in the second chamber 22 using a circulation unit 46 or other inert gas inputs. The flow of inert gas can be initiated during the entire cooling cycle or after the super-cooling is complete and the product is being allowed to equilibrate to a safe handling temperature. As noted above, the flow of inert gas post-rapid cooling can be warmed. As detailed above, a circulation unit 46 can be provided to flow the inert gas across the chamber from an inlet and into an outlet with the inlet and outlet being in fluid communication outside of the chamber and a filter disposed there between to allow the gas collected at the outlet to be filtered and recirculated back into the first chamber 20. This recirculation can be utilized with or without continued injection of fresh inert gas. In alternative embodiments, a flow of fresh inert gas can be maintained and the circulation unit 46 can simply vent the outflow of inert gas from the first chamber 20 without recycling the inert gas.

The inert gas can be filtered, for example HEPA filtered. The inert gas can be nitrogen, argon, carbon dioxides, and mixtures thereof. Use of air or noble gasses are also contemplated herein. For example, the inert gas can be filtered and/or HEPA filtered nitrogen. The flow of inert gas such as nitrogen can reduce or eliminate oxygen present in the first chamber 20, which can aid in maintain pasteurization performance by preventing spores that may remain on the product after pasteurization from activating and growing.

After the product reaches the safe handling temperature, the product outlet is exposed and the product is flowed out of the second chamber 22 and thereby out of the pasteurization unit. As discussed above, the product can be flowed into a sterile container, field pack or other packaging, or into a downstream unit such as the vibratory feeder and bagging system described above.

The methods of the disclosure can result in a sterilized product having a contaminant value of less than 10,000 cfu/gram. The contaminant can include any one of yeast, mold, bacteria, virus, and fungus, and particular yeast, mold, and bacteria. FIG. 22 illustrates thermal death curves for a pasteurization cycle at about 73.8° C. (165° F.) at different pasteurization times using a unit in accordance with the disclosure. In the example shown in FIG. 22, the product was held at the pasteurization temperature using steam, inert gas, and conduction heating of the chamber.

The methods of the disclosure can result in a field package product which can maintain a contaminant level of less than 10,000 cfu/gram for a storage time of at least 5 days, at least 7 days, at least 10 days, or more.

In any of the embodiments herein, when processing cannabis, hemp, or CBD, the method can further include adding terpenes or flavorings to the internal volume during the tempering of the product back to a safe handling temperature. The terpenes or flavorings can be added in a vaporized or aerosolized form for example with or without the flow of inert gas for a time sufficient to allow for penetration of the terpenes and flavorings into the product.

Post-pasteurization moisture levels can be controlled either in the second chamber 22 after cooling and/or after transport out of the second chamber 22. In any of the embodiments herein, moisture can be added to the product after pasteurization using sterile water or distilled water. Moisture levels can be reduced after pasteurization through the flow of inert gas, for example warmed inert gas. Use of air or noble gasses are also contemplated. Depending on the product being pasteurized and pasteurization conditions it may be advantageous to adjust the moisture levels in the pasteurization product to be the same as the pre-pasteurization level or otherwise modify the moisture level in the pasteurized product to be different (higher or lower) than the pre-pasteurized products.

The pasteurization units, systems, and methods of the disclosure can allow for faster cycle times as compared to conventional vacuum pasteurization methods, particularly for cannabis, hemp, and CBD products, can have higher kill rates at short cycle times, can be gentler on the product avoiding degradation of sensitive products, such as cannabis, hemp, and CBD, can avoid having potentially harmful chemicals present in product or need for off-gassing thereof, such as residual sterilizing gasses such as hydrogen peroxide or ozone.

The use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict embodiments for purposes of illustration only. One of ordinary skill in the art will readily recognize from the following discussion that alternative embodiments of the structures and methods illustrated herein may be employed without departing from the principles described herein.

Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed:

1. A pasteurization unit for pasteurizing a product, comprising:
a first chamber having an interior volume defined by a plurality of walls and having a product inlet for introduction of product into the interior volume and a product outlet for release of the product from the first chamber;
a vapor generator in fluid communication with the first chamber for introduction of vapor into the first chamber for pasteurization of the product; the product inlet and the product outlet being sealable during pasteurization;
a second chamber having an interior volume defined by a plurality of walls and comprising a product outlet and a product inlet, the second chamber being arranged to receive product from the first chamber for cooling the product;
cryogenic fluid inlets in fluid communication with a cryogenic fluid source, the cryogenic fluid inlets being arranged to direct cryogenic fluid into the interior volume of the second chamber to cool the product as it enters and/or once in the interior volume of the second chamber; a middle assembly arranged between the first and second chamber, the middle assembly having one or more actuatable doors configured to expose the product outlet of the first chamber and the product inlet of the second chamber when open and close over the product outlet of the first chamber and the product inlet of the second chamber when closed.

2. The pasteurization unit of claim 1, further comprising a circulation unit arranged in fluid communication with the vapor generator, the circulation unit comprising an inlet for receiving vapor from the vapor generator and an outlet in fluid communication with the first chamber for flowing vapor into the first chamber.

3. The pasteurization unit of claim 2, further comprising a heater arranged in the channel.

4. The pasteurization unit of claim 1, further comprising a bottom assembly arrange downstream of the second chamber, the bottom assembly comprising actuatable doors for opening and closing over the product outlet of the second chamber.

5. The pasteurization unit of claim 1, further comprising a cartridge for loading the product into the first chamber, the product adapted to be removably received upstream of the first chamber for introduction of the product from the chamber into the internal volume of the first chamber through the first chamber product inlet.

6. The pasteurization unit of claim 1, wherein the vapor generator is in fluid communication with an inert gas source and adapted to flow vapor and inert gas into the first chamber.

7. The pasteurization unit of claim 1, further comprising a circulation unit arranged in fluid communication with an inert gas source, the circulation unit comprising an inlet for receiving inert gas from the inert gas source and an outlet in fluid communication with the second chamber for flowing vapor into the second chamber.

8. The pasteurization unit of claim 7, wherein the circulation unit comprises a channel through which the inert gas flows.

9. The pasteurization unit of claim 8, further comprising a blower arranged within the channel.

10. A process for pasteurizing cannabis using the pasteurization unit of claim 1, comprising:
introducing the product into the first chamber;
flowing vapor from the vapor generator into the first chamber at a rate to maintain a pasteurization temperature for a pasteurization time;
releasing the product from the first chamber through the first chamber product outlet and introducing the product into the second chamber through the second chamber product inlet;
flowing cryogenic fluid into the second chamber to cool the product;
holding the product in the second chamber for a hold time after cooling to bring the product to room temperature; and
releasing the product from the second chamber through the second chamber product outlet.

11. The process of claim 10, wherein the pasteurization temperature is about 65° C. to about 75° C.

12. The process of claim 10, wherein the pasteurization time is about 1 min to about 10 min.

13. The process of claim 10, further comprising preheating the first chamber before introducing the product into the first chamber.

14. The process of claim 10, wherein flowing vapor from the vapor generator comprises flowing a mixture of vapor and inert gas.

15. The process of claim 10, wherein the pasteurization temperature is a temperature at which the first chamber is preheated wherein the temperature at which the first chamber is preheated is up to 95° C.

* * * * *